(12) United States Patent
Des Combes et al.

(10) Patent No.: US 8,791,119 B2
(45) Date of Patent: Jul. 29, 2014

(54) 3,4-DIHYDROPYRROLO[1,2-A]PYRAZINE-2,8(1H)-DICARBOXAMIDE DERIVATIVES, PREPARATION THEREOF AND THERAPEUTIC USE THEREOF FOR DISEASES INVOLVING CASEIN KINASE 1 EPSILON AND/OR CASEIN KINASE 1 DELTA

(71) Applicant: Sanofi, Paris (FR)

(72) Inventors: Sylvain Cote Des Combes, Paris (FR); Jacques Froissant, Paris (FR); Jean-Francois Gibert, Paris (FR); Frank Marguet, Paris (FR); Christophe Pacaud, Paris (FR); Frédéric Puech, Paris (FR); Antoine Ravet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/688,916

(22) Filed: Nov. 29, 2012

(65) Prior Publication Data
US 2013/0090340 A1    Apr. 11, 2013

Related U.S. Application Data

(63) Continuation of application No. PCT/IB2011/001594, filed on Jun. 1, 2011.

(30) Foreign Application Priority Data

Jun. 3, 2010    (FR) ...................................... 10 54372

(51) Int. Cl.
*A61K 31/495*    (2006.01)
*C07D 241/38*    (2006.01)

(52) U.S. Cl.
USPC ........ 514/249; 544/116; 544/349; 548/364.7; 548/518; 549/14; 549/356; 549/429; 549/510

(58) Field of Classification Search
CPC ............................ A61K 31/495; C07D 241/38
USPC ........ 514/249; 544/116, 349; 548/364.7, 518; 549/14, 356, 429, 510
See application file for complete search history.

(56) References Cited

U.S. PATENT DOCUMENTS

| | | |
|---|---|---|
| 2005/0131012 A1 | 6/2005 | Metz et al. |
| 2009/0192147 A1 | 7/2009 | Ayral-Kaloustian et al. |
| 2010/0197668 A1 | 8/2010 | Baudoin et al. |

FOREIGN PATENT DOCUMENTS

| | | |
|---|---|---|
| WO | WO 03/024967 | 3/2003 |
| WO | WO 03/064423 | 8/2003 |
| WO | WO 2008/147713 | 12/2008 |
| WO | WO 2009/044007 | 4/2009 |

OTHER PUBLICATIONS international Search Report for WO2011/161537 dated Dec. 29, 2011.

*Primary Examiner* — Douglas M Willis
(74) *Attorney, Agent, or Firm* — Kelly L. Bender

(57) ABSTRACT

Compounds corresponding to the general formula (I)

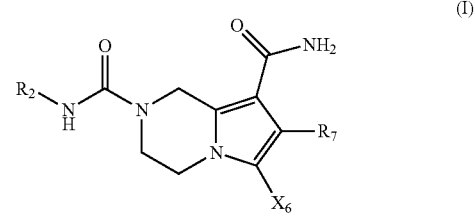

wherein $R_2$ represents a group $C_{1-10}$-alkyl, $C_{3-10}$-cycloalkyl, $C_{3-7}$-cycloalkyl-$C_{1-6}$-alkyl, $C_{1-6}$-alkyl-$C_{3-7}$-cycloalkyl, $C_{3-7}$-cycloalkyl-$C_{3-7}$-cycloalkyl, $C_{1-6}$-alkylthio-$C_{1-10}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, hydroxy-$C_{3-10}$-cycloalkyl, $C_{1-10}$-fluoroalkyl or $C_{3-10}$-fluorocycloalkyl; an optionally substituted heterocyclic group; a group $C_{1-10}$-alkyl substituted with an optionally substituted heterocyclic group; $X_6$ represents a group chosen from hydrogen, fluorine, chlorine and bromine atoms or a group $C_{1-6}$-alkyl, $C_{3-7}$-cycloalkyl, $C_{3-7}$-cycloalkyl-$C_{1-6}$-alkyl, $C_{1-6}$-fluoroalkyl or cyano; and $R_7$ represents an aryl group such as phenyl or naphthyl, optionally substituted with one or more substituents,
in the form of the base or of an acid-addition salt, and the therapeutic use thereof.

8 Claims, No Drawings

3,4-DIHYDROPYRROLO[1,2-A]PYRAZINE-2,8(1H)-DICARBOXAMIDE DERIVATIVES, PREPARATION THEREOF AND THERAPEUTIC USE THEREOF FOR DISEASES INVOLVING CASEIN KINASE 1 EPSILON AND/OR CASEIN KINASE 1 DELTA

This application is a continuation of International application No. PCT/IB2011/001594, filed Jun. 1, 2011, which is incorporated herein by reference in its entirety; which claims the benefit of priority of French Patent Application No. 1054372, filed Jun. 3, 2010.

The present invention relates to 3,4-dihydropyrrolo[1,2-a]pyrazine-2,8(1H)-dicarboxamide derivatives, to a process for preparing them and to their therapeutic use, in the treatment or prevention of diseases involving casein kinase 1 epsilon and/or casein kinase 1 delta.

The technical problem according to the present invention is that of obtaining novel compounds that inhibit the enzymes CK1epsilon and/or CK1delta, so as to modify the circadian rhythm, and which may be useful for treating disorders linked to the circadian rhythm.

One subject of the present invention is compounds corresponding to the general formula (I):

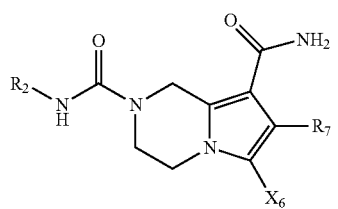

in which
$R_2$ represents:
a group $C_{1-10}$-alkyl, $C_{3-7}$-cycloalkyl-$C_{1-6}$-alkyl, $C_{1-6}$-alkylthio-$C_{1-10}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, $C_{1-10}$-fluoroalkyl, $C_{1-10}$-alkyl-oxyimino-$C_{1-10}$-alkyl,
a group $C_{3-10}$-cycloalkyl, $C_{3-10}$-fluorocycloalkyl, hydroxy-$C_{3-10}$-cycloalkyl,
a group $C_{3-7}$-cycloalkyl which may be substituted with one or two groups independently chosen from $C_{1-6}$-alkyl, $C_{3-7}$-cycloalkyl, hydroxyl, $C_{1-10}$-fluoroalkyl and $C_{1-10}$-alkyl-oxyimino,
a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl, $C_{1-6}$-fluoroalkyl,
a group $C_{1-10}$-alkyl substituted with a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl, $C_{1-6}$-fluoroalkyl;
$X_6$ represents a hydrogen, fluorine, chlorine or bromine atom or a group $C_{1-6}$-alkyl, $C_{3-7}$-cycloalkyl, $C_{3-7}$-cycloalkyl-$C_{1-6}$-alkyl, $C_{1-6}$-fluoroalkyl or cyano;

$R_7$ represents a phenyl group or a naphthyl group, optionally substituted with one or more substituents $X_7$, which may be identical or different, chosen independently;
$X_7$ represents:
a halogen atom chosen from fluorine, chlorine and bromine atoms,
or a group chosen from:
hydroxyl,
$C_{1-6}$-alkyl, $C_{3-7}$-cycloalkyl, $C_{3-7}$-cycloalkyl-$C_{1-6}$-alkyl, hydroxy-$C_{1-6}$-alkyl, hydroxy-$C_{3-7}$-cycloalkyl, hydroxy-$C_{3-7}$-cycloalkyl-$C_{1-6}$-alkyl,
$C_{1-6}$-alkoxy, $C_{3-7}$-cycloalkoxy, $C_{3-7}$-cycloalkyl-$C_{1-6}$-alkoxy,
$C_{1-6}$-alkylthio, $C_{3-7}$-cycloalkylthio, $C_{3-7}$-cycloalkyl-$C_{1-6}$-alkylthio,
aryl, aryl-$C_{1-6}$-alkyl,
aryloxy, aryl-$C_{1-6}$-alkoxyl,
$C_{1-6}$-fluoroalkyl, $C_{3-7}$-fluorocycloalkyl, $C_{3-7}$-fluorocycloalkyl-$C_{1-6}$-alkyl,
$C_{1-6}$-fluoroalkoxy, $C_{3-7}$-fluorocycloalkoxy, $C_{3-7}$-fluorocycloalkyl-$C_{1-6}$-alkoxy,
cyano, cyano-$C_{1-6}$-alkyl, cyano-$C_{1-6}$-alkoxyl,
$NR_aR_b$, $NR_cCOR_d$, $NR_cSO_2R_d$, $NR_cSO_2NR_aR_b$, $CONR_aR_b$, $CON(OR_c)R_d$,
a heteroaryl group,
the aryl or heteroaryl groups being optionally substituted with one or more substituents chosen from fluorine, chlorine and bromine atoms or a group $C_{1-6}$-alkyl, $C_{3-7}$-cycloalkyl, $C_{1-6}$-alkoxy, $C_{1-6}$-fluoroalkyl, $C_{1-6}$-fluoroalkoxy or cyano,
$R_a$ and $R_b$ represent, independently of each other, a hydrogen atom or a group $C_{1-6}$-alkyl, $C_{3-7}$-cycloalkyl or $C_{3-7}$-cycloalkyl-$C_{1-6}$-alkyl, or alternatively they form with the atom that bears them a ring chosen from azetidine, pyrrolidine, piperidine, morpholine, thiomorpholine, azepine and piperazine, this ring being optionally substituted with one or more groups $C_{1-6}$-alkyl,
$R_c$ and $R_d$ represent, independently of each other, a hydrogen atom or a group $C_{1-6}$-alkyl, $C_{3-7}$-cycloalkyl or $C_{3-7}$-cycloalkyl-$C_{1-6}$-alkyl.

Among the compounds of general formula (I), a first subgroup of compounds is formed by the compounds of general formula (I) for which:
$R_2$ represents:
a group $C_{1-10}$-alkyl, $C_{3-10}$-cycloalkyl, $C_{3-7}$-cycloalkyl-$C_{1-6}$-alkyl, $C_{1-6}$-alkyl-$C_{3-7}$-cycloalkyl, $C_{3-7}$-cycloalkyl-$C_{3-7}$-cycloalkyl, $C_{1-6}$-alkylthio-$C_{1-10}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, hydroxy-$C_{3-10}$-cycloalkyl, $C_{1-10}$-fluoroalkyl, $C_{3-10}$-fluorocycloalkyl,
a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl, $C_{1-6}$-fluoroalkyl,
a group $C_{1-10}$-alkyl substituted with a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl, $C_{1-6}$-fluoroalkyl;
$X_6$ represents a hydrogen, fluorine, chlorine or bromine atom or a group $C_{1-6}$-alkyl, $C_{3-7}$-cycloalkyl, $C_{3-7}$-cycloalkyl-$C_{1-6}$-alkyl, $C_{1-6}$-fluoroalkyl or cyano;

$R_7$ represents a phenyl group or a naphthyl group, optionally substituted with one or more substituents $X_7$, which may be identical or different, chosen independently;

$X_7$ represents:
  a halogen atom chosen from fluorine, chlorine and bromine atoms,
  or a group chosen from:
  hydroxyl,
  $C_{1-6}$-alkyl, $C_{3-7}$-cycloalkyl, $C_{3-7}$-cycloalkyl-$C_{1-6}$-alkyl, hydroxy-$C_{1-6}$-alkyl, hydroxy-$C_{3-7}$-cycloalkyl, hydroxy-$C_{3-7}$-cycloalkyl-$C_{1-6}$-alkyl,
  $C_{1-6}$-alkoxy, $C_{3-7}$-cycloalkoxy, $C_{3-7}$-cycloalkyl-$C_{1-6}$-alkoxy,
  $C_{1-6}$-alkylthio, $C_{3-7}$-cycloalkylthio, $C_{3-7}$-cycloalkyl-$C_{1-6}$-alkylthio,
  aryl, aryl-$C_{1-6}$-alkyl,
  aryloxy, aryl-$C_{1-6}$-alkoxy,
  $C_{1-6}$-fluoroalkyl, $C_{3-7}$-fluorocycloalkyl, $C_{3-7}$-fluorocycloalkyl-$C_{1-6}$-alkyl,
  $C_{1-6}$-fluoroalkoxy, $C_{3-7}$-fluorocycloalkoxy, $C_{3-7}$-fluorocycloalkyl-$C_{1-6}$-alkoxy,
  cyano, cyano-$C_{1-6}$-alkyl, cyano-$C_{1-6}$-alkoxy,
  $NR_aR_b$, $NR_cCOR_d$, $NR_cSO_2R_d$, $NR_cSO_2NR_aR_b$, $CONR_aR_b$, $CON(OR_c)R_d$,
  a heteroaryl group,
  the aryl or heteroaryl groups being optionally substituted with one or more substituents chosen from fluorine, chlorine and bromine atoms or a group $C_{1-6}$-alkyl, $C_{3-7}$-cycloalkyl, $C_{1-6}$-alkoxy, $C_{1-6}$-fluoroalkyl, $C_{1-6}$-fluoroalkoxy or cyano, $R_a$ and $R_b$ represent, independently of each other, a hydrogen atom or a group $C_{1-6}$-alkyl, $C_{3-7}$-cycloalkyl or $C_{3-7}$-cycloalkyl-$C_{1-6}$-alkyl, or alternatively they form with the atom that bears them a ring chosen from azetidine, pyrrolidine, piperidine, morpholine, thiomorpholine, azepine and piperazine, this ring being optionally substituted with one or more groups $C_{1-6}$-alkyl, $R_c$ and $R_d$ represent, independently of each other, a hydrogen atom or a group $C_{1-6}$-alkyl, $C_{3-7}$-cycloalkyl or $C_{3-7}$-cycloalkyl-$C_{1-6}$-alkyl.

Among the compounds of general formula (I), a second subgroup of compounds is formed by compounds for which $R_2$ represents:
  a group $C_{1-10}$-alkyl, $C_{3-7}$-cycloalkyl-$C_{1-6}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, $C_{1-10}$-fluoroalkyl,
  a group $C_{3-10}$-cycloalkyl, $C_{3-10}$-fluorocycloalkyl, hydroxy-$C_{3-10}$-cycloalkyl,
  a group $C_{3-7}$-cycloalkyl which may be substituted with one or two groups independently chosen from $C_{1-6}$-alkyl, $C_{3-7}$-cycloalkyl, hydroxyl, $C_{1-10}$-fluoroalkyl and $C_{1-10}$-alkyl-oxyimino,
  a heterocyclic group comprising from 3 to 8 carbon atoms and at least one heteroatom chosen from oxygen or a sulfur atom in dioxide form, this heterocyclic group possibly being substituted with one or more groups $C_{1-6}$-alkyl,
  a group $C_{1-10}$-alkyl substituted with a heterocyclic group comprising from 3 to 8 carbon atoms and at least one oxygen heteroatom, this heterocyclic group possibly being substituted with one or more groups $C_{1-6}$-alkyl;
and $X_6$ and $R_7$ are as defined in the general formula (I).

Among the compounds of general formula (I), a third subgroup of compounds is formed by compounds for which $R_2$ represents:
  a group $C_{1-10}$-alkyl, $C_{3-10}$-cycloalkyl, $C_{3-7}$-cycloalkyl-$C_{1-6}$-alkyl, $C_{3-7}$-cycloalkyl-$C_{3-7}$-cycloalkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, hydroxy-$C_{3-10}$-cycloalkyl, $C_{1-10}$-fluoroalkyl, $C_{3-10}$-fluorocycloalkyl,
  a heterocyclic group comprising from 3 to 8 carbon atoms and at least one heteroatom chosen from an oxygen atom or a sulfur atom in dioxide form;
and $X_6$ and $R_7$ are as defined in the general formula (I).

Among the compounds of general formula (I), a fourth subgroup of compounds is formed by compounds for which $R_2$ represents:
  a group $C_{1-10}$-alkyl, $C_{3-10}$-cycloalkyl, $C_{3-7}$-cycloalkyl-$C_{1-6}$-alkyl, $C_{3-7}$-cycloalkyl-$C_{3-7}$-cycloalkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, hydroxy-$C_{3-10}$-cycloalkyl, $C_{1-10}$-fluoroalkyl, $C_{3-10}$-fluorocycloalkyl;
and $X_6$ and $R_7$ are as defined in the general formula (I).

Among the compounds of general formula (I), a fifth subgroup of compounds is formed by compounds for which $R_2$ represents:
  a heterocyclic group comprising from 3 to 8 carbon atoms and at least one heteroatom chosen from an oxygen atom or a sulfur atom in dioxide form;
and $X_6$ and $R_7$ are as defined in the general formula (I).

Among the compounds of general formula (I), a sixth subgroup of compounds is formed by compounds for which $R_2$ represents a group chosen from:
cyclo-propyl
iso-propyl
iso-butyl
tert-butyl
cyclo-propylmethyl
3-methyl-butyl
2,2-dimethyl-propyl
2-ethyl-butyl
3,3-dimethyl-butyl
cyclo-hexyl
cyclo-hexylmethyl
1,1'-bi(cyclo-propyl)-1-yl
2,4,4-trimethylpentan-2-yl
bicyclo[2.2.1]hept-2-yl
hexahydro-2,5-methanopentalen-3a(1H)-yl or tricyclo[3.3.1.0$^{3.7}$]non-3-yl
adamantan-1-yl or tricyclo[3.3.1.1$^{3.7}$]dec-1-yl
2,2,2-trifluoro-ethyl
(2S)-1,1,1-trifluoropropan-2-yl
(S)-2,2,2-trifluoro-1-methyl-ethyl
3,3,3-trifluoro-propyl
1,1,1-trifluoro-2-methylpropan-2-yl
2,2,2-trifluoro-1,1-dimethyl-ethyl
4,4,4-trifluoro-butyl
4,4-difluoro-cyclo-hexyl
4-hydroxy-cyclo-hexyl
4-tert-butoxyimino-cyclohexyl
4-methoxyimino-cyclohexyl
4-hydroxy-4-methyl-cyclohexyl
4-hydroxy-4-trifluoromethyl-cyclohexyl
3-hydroxy-2,2-dimethyl-propyl
[1-(hydroxymethyl)cyclo-propyl]methyl
1-methoxy-2-methylpropan-2-yl
tetrahydro-2H-pyran-4-yl
2,2-dimethyl-tetrahydro-2H-pyran-4-yl
2,6-dimethyl-tetrahydro-2H-pyran-4-yl
oxetan-3-yl
3-methyl-oxetan-3-ylmethyl tetrahydro-furan-3-yl
1,1-dioxydotetrahydrothiophen-3-yl
1,1-dioxydotetrahydro-2H-thiopyran-4-yl,
and $X_6$ and $R_7$ are as defined in the general formula (I).

Among the compounds of general formula (I), a seventh subgroup of compounds is formed by compounds for which $R_2$ represents a group chosen from:
cyclo-propyl
iso-propyl
iso-butyl
tert-butyl
cyclo-propylmethyl
3-methyl-butyl
2,2-dimethyl-propyl
2-ethyl-butyl
3,3-dimethyl-butyl
cyclo-hexyl
cyclo-hexylmethyl
1,1'-bi(cyclo-propyl)-1-yl
2,4,4-trimethylpentan-2-yl
bicyclo[2.2.1]hept-2-yl
hexahydro-2,5-methanopentalen-3a(1H)-yl or
tricyclo[3.3.1.0$^{3.7}$]non-3-yl
adamantan-1-yl or
tricyclo[3.3.1.1$^{3.7}$]dec-1-yl
2,2,2-trifluoro-ethyl
(2S)-1,1,1-trifluoropropan-2-yl
3,3,3-trifluoro-propyl
1,1,1-trifluoro-2-methylpropan-2-yl
4,4,4-trifluoro-butyl
4,4-difluoro-cyclo-hexyl
4-hydroxy-cyclo-hexyl
3-hydroxy-2,2-dimethyl-propyl
[1-(hydroxymethyl)cyclo-propyl]methyl
1-methoxy-2-methylpropan-2-yl
tetrahydro-2H-pyran-4-yl
oxetan-3-yl
tetrahydro-furan-3-yl
1,1-dioxydotetrahydrothiophen-3-yl
1,1-dioxydotetrahydro-2H-thiopyran-4-yl,
and $X_6$ and $R_7$ are as defined in the general formula (I).

Among the compounds of general formula (I), an eighth subgroup of compounds is formed by compounds for which $X_6$ represents a hydrogen, fluorine, chlorine or bromine atom or a group $C_{1-6}$-alkyl, $C_{3-7}$-cycloalkyl or cyano; and $R_2$ and $R_7$ are as defined in the general formula (I).

Among the compounds of general formula (I), a ninth subgroup of compounds is formed by compounds for which $X_6$ represents a hydrogen, fluorine, chlorine or bromine atom or the cyano group; and $R_2$ and $R_7$ are as defined in the general formula (I).

Among the compounds of general formula (I), a tenth subgroup of compounds is formed by compounds for which $X_6$ represents a hydrogen atom or a group $C_{1-6}$-alkyl or $C_{3-7}$-cycloalkyl; and $R_2$ and $R_7$ are as defined in the general formula (I). Among the compounds of general formula (I), an eleventh subgroup of compounds is formed by compounds for which $X_6$ represents a fluorine, chlorine or bromine atom or a methyl, cyclopropyl or cyano group; and $R_2$ and $R_7$ are as defined in the general formula (I).

Among the compounds of general formula (I), a twelfth subgroup of compounds is formed by compounds for which $R_7$ represents a phenyl group optionally substituted with one or more substituents $X_7$, which may be identical or different, chosen independently from:
  a fluorine or chlorine atom or a group chosen from $C_{1-6}$-alkyl, $C_{3-7}$-cycloalkyl,
  $C_{1-6}$-alkoxy, $C_{3-7}$-cycloalkyl-$C_{1-6}$-alkoxy,
  $C_{1-6}$-alkylthio,
  aryl,
  aryloxy, aryl-$C_{1-6}$-alkoxy,
  $C_{2-6}$ fluoroalkyl,
  $C_{2-6}$ fluoroalkoxy,
  cyano, cyano-$C_{1-6}$-alkoxy,
  $NR_aR_b$, $NR_cSO_2R_d$, $NR_cSO_2NR_aR_b$, $CONR_aR_b$, $CON(OR_c)R_d$,
  heteroaryl chosen from oxadiazolyl and pyrazolyl groups, optionally substituted with a group $C_{1-6}$-alkyl, the aryl group being optionally substituted with a fluorine atom,
$R_a$ and $R_b$ represent, independently of each other, a hydrogen atom or a group $C_{1-6}$-alkyl, $C_{3-7}$-cycloalkyl, or alternatively they form with the atom that bears them a ring chosen from pyrrolidine and morpholine,
$R_c$ and $R_d$ represent, independently of each other, a hydrogen atom or a group $C_{1-6}$-alkyl;
and $R_2$ and $X_6$ are as defined in the general formula (I).

Among the compounds of general formula (I), a thirteenth subgroup of compounds is formed by compounds for which $R_7$ represents a phenyl group optionally substituted with one or more substituents $X_7$, which may be identical or different, chosen independently from:
  a fluorine or chlorine atom,
  methyl or isopropyl, cyclo-hexyl,
  methoxy, butoxy, cyclo-propylmethoxy,
  methylsulfanyl,
  phenyl,
  phenoxy,
  benzyloxy, 4-fluorobenzyloxy,
  trifluoromethyl,
  trifluoromethoxy,
  cyano, cyanomethoxy,
  4-dimethylamino, morpholin-4-yl, methanesulfonylamino, (dimethylsulfamoyl)amino, dimethylcarbamoyl, cyclo-propylcarbamoyl, pyrrolidine-1-carbonyl, methoxy-methyl-carbamoyl, and
  5-methyl-[1.3.4]oxadiazol-2-yl, pyrazol-1-yl;
and $R_2$ and $X_6$ are as defined in the general formula (I).

Among the compounds of general formula (I), a fourteenth subgroup of compounds is formed by compounds for which $R_7$ represents a naphthyl group optionally substituted with one or more substituents $X_7$, which may be identical or different, independently chosen as described above for the compounds of general formula (I), and $R_2$ and $X_6$ are as defined in the general formula (I).

Among the compounds of general formula (I), a fifteenth subgroup of compounds is formed by compounds for which $R_7$ represents an unsubstituted naphthyl group, and $R_2$ and $X_6$ are as defined in the general formula (I).

Among the compounds of general formula (I), a sixteenth subgroup of compounds is formed by the compounds of general formula (I) in which both $R_2$ and/or $R_7$ and/or $X_6$ and/or $X_7$ are as defined in the above subgroups.

Among the compounds of general formula (I), a seventeenth subgroup of compounds is formed by the compounds of general formula (I) for which:
$R_2$ represents:
  a group $C_{1-10}$-alkyl, $C_{3-7}$-cycloalkyl-$C_{1-6}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, $C_{1-10}$-fluoroalkyl,
  a group $C_{3-10}$-cycloalkyl, $C_{3-10}$-fluorocycloalkyl, hydroxy-$C_{3-10}$-cycloalkyl, a group $C_{3-7}$-cycloalkyl which may be substituted with one or two groups independently chosen from $C_{1-6}$-alkyl, $C_{3-7}$-cycloalkyl, hydroxyl, $C_{1-10}$-fluoroalkyl and $C_{1-10}$-alkyl-oxyimino, a heterocyclic group comprising from 3 to 8 carbon atoms and at least one heteroatom chosen from oxygen or a sulfur atom in dioxide form, this heterocyclic group possibly being substituted with one or more groups $C_{1-6}$-alkyl, a group $C_{1-10}$-alkyl substituted with a heterocyclic group comprising from 3 to 8 carbon atoms and at least one oxygen heteroatom, this heterocyclic group possibly being substituted with one or more groups $C_{1-6}$-alkyl, $R_7$ represents a phenyl group optionally substituted with one or more substituents $X_7$, which may be identical or different, chosen independently from:

a fluorine or chlorine atom or a group chosen from
$C_{1-6}$-alkyl, $C_{3-7}$-cycloalkyl,
$C_{1-6}$-alkoxy, $C_{3-7}$-cycloalkyl-$C_{1-6}$-alkoxy,
$C_{1-6}$-alkylthio,
aryl,
aryloxy, aryl-$C_{1-6}$-alkoxy,
$C_{2-6}$ fluoroalkyl,
$C_{2-6}$ fluoroalkoxy,
cyano, cyano-$C_{1-6}$-alkoxy,
$NR_aR_b$, $NR_cSO_2R_d$, $NR_cSO_2NR_aR_b$, $CONR_aR_b$, $CON(OR_c)R_d$,
heteroaryl chosen from oxadiazolyl and pyrazolyl groups, optionally substituted with a group $C_{1-6}$-alkyl, the aryl group being optionally substituted with a fluorine atom, $R_a$ and $R_b$ represent, independently of each other, a hydrogen atom or a group $C_{1-6}$-alkyl, $C_{3-7}$-cycloalkyl, or alternatively they form with the atom that bears them a ring chosen from pyrrolidine and morpholine, $R_c$ and $R_d$ represent, independently of each other, a hydrogen atom or a group $C_{1-6}$-alkyl.

Among the compounds of general formula (I), an eighteenth subgroup of compounds is formed by the compounds of general formula (I) for which:

$R_2$ represents:
a group $C_{1-10}$-alkyl, $C_{3-10}$-cycloalkyl, $C_{3-7}$-cycloalkyl-$C_{1-6}$-alkyl, $C_{3-7}$-cycloalkyl-$C_{3-7}$-cycloalkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, hydroxy-$C_{3-10}$-cycloalkyl, $C_{1-10}$-fluoroalkyl, $C_{3-10}$-fluorocycloalkyl, a heterocyclic group comprising from 3 to 8 carbon atoms and at least one heteroatom chosen from an oxygen atom or a sulfur atom in dioxide form;

$X_6$ represents a hydrogen, fluorine, chlorine or bromine atom or a group $C_{1-6}$-alkyl, $C_{3-7}$-cycloalkyl or cyano;

$R_7$ represents a phenyl group optionally substituted with one or more substituents $X_7$, which may be identical or different, chosen independently from:

a fluorine or chlorine atom or a group chosen from
$C_{1-6}$-alkyl, $C_{3-7}$-cycloalkyl,
$C_{1-6}$-alkoxy, $C_{3-7}$-cycloalkyl-$C_{1-6}$-alkoxy,
$C_{1-6}$-alkylthio,
aryl,
aryloxy, aryl-$C_{1-6}$-alkoxy,
$C_{1-6}$ fluoroalkyl,
$C_{1-6}$ fluoroalkoxy,
cyano, cyano-$C_{1-6}$-alkoxy,
$NR_aR_b$, $NR_cSO_2R_d$, $NR_cSO_2NR_aR_b$, $CONR_aR_b$, $CON(OR_c)R_d$,
heteroaryl chosen from oxadiazolyl and pyrazolyl groups, optionally substituted with a group $C_{1-6}$-alkyl, the aryl group being optionally substituted with a fluorine atom, $R_a$ and $R_b$ represent, independently of each other, a hydrogen atom or a group $C_{1-6}$-alkyl, $C_{3-7}$-cycloalkyl, or alternatively they form with the atom that bears them a ring chosen from pyrrolidine and morpholine, $R_c$ and $R_d$ represent, independently of each other, a hydrogen atom or a group $C_{1-6}$-alkyl.

Among the compounds of general formula (I), a nineteenth subgroup of compounds is formed by the compounds of general formula (I) for which:

$R_2$ represents:
a group $C_{1-10}$-alkyl, $C_{3-7}$-cycloalkyl-$C_{1-6}$-alkyl, $C_{1-6}$-alkylthio-C-$_{1-10}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, $C_{1-10}$-fluoroalkyl, $C_{1-10}$-alkyl-oxyimino-$C_{1-10}$-alkyl, a group $C_{3-10}$-cycloalkyl, $C_{3-10}$-fluorocycloalkyl, hydroxy-$C_{3-10}$-cycloalkyl, a group $C_{3-7}$-cycloalkyl which may be substituted with one or two groups independently chosen from $C_{1-6}$-alkyl, $C_{3-7}$-cycloalkyl, hydroxyl, $C_{1-10}$-fluoroalkyl and $C_{1-10}$-alkyl-oxyimino, a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl and $C_{1-6}$-fluoroalkyl, this heterocyclic group being chosen from oxetanyl, tetrahydrofuryl, tetrahydro-2H-pyranyl, oxepanyl, thietanyl, tetrahydrothiophenyl, tetrahydro-2H-thiopyranyl, thiepanyl, 1,1-dioxydothietanyl, 1,1-dioxydotetrahydrothiophenyl, 1,1-dioxydotetrahydro-2H-thiopyranyl and 1,1-dioxydothiepanyl;

a group $C_{1-10}$-alkyl substituted with a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups from among hydroxyl, $C_{1-6}$-alkyl, hydroxy-$C_{1-6}$-alkyl, $C_{1-6}$-fluoroalkyl, this heterocyclic group being chosen from oxetanyl, tetrahydrofuryl, tetrahydro-2H-pyranyl, oxepanyl, thietanyl, tetrahydrothiophenyl, tetrahydro-2H-thiopyranyl, thiepanyl, 1,1-dioxydothietanyl, 1,1-dioxydotetrahydrothiophenyl, 1,1-dioxydotetrahydro-2H-thiopyranyl and 1,1-dioxydothiepanyl;

$X_6$ represents a hydrogen, fluorine, chlorine or bromine atom or a group $C_{1-6}$-alkyl, $C_{3-7}$-cycloalkyl, $C_{3-7}$-cycloalkyl-$C_{1-6}$-alkyl, $C_{1-6}$-fluoroalkyl or cyano;

$R_7$ represents a phenyl group or a naphthyl group, optionally substituted with one or more substituents $X_7$, which may be identical or different, chosen independently;

$X_7$ represents:
a halogen atom chosen from fluorine, chlorine and bromine atoms,
or a group chosen from:
hydroxyl,
$C_{1-6}$-alkyl, $C_{3-7}$-cycloalkyl, $C_{3-7}$-cycloalkyl-$C_{1-6}$-alkyl,
hydroxy-$C_{1-6}$-alkyl, hydroxy-$C_{3-7}$-cycloalkyl, hydroxy-$C_{3-7}$-cycloalkyl-$C_{1-6}$-alkyl,
$C_{1-6}$-alkoxy, $C_{3-7}$-cycloalkoxy, $C_{3-7}$-cycloalkyl-$C_{1-6}$-alkoxy,
$C_{1-6}$-alkylthio, $C_{3-7}$-cycloalkylthio, $C_{3-7}$-cycloalkyl-$C_{1-6}$-alkylthio,
aryl, aryl-$C_{1-6}$-alkyl,
aryloxy, aryl-$C_{1-6}$-alkoxy, $C_{1-6}$-fluoroalkyl, $C_{3-7}$-fluorocycloalkyl, $C_{3-7}$-fluorocycloalkyl-$C_{1-6}$-alkyl, $C_{1-6}$-fluoroalkoxy, $C_{3-7}$-fluorocycloalkoxy, $C_{3-7}$-fluorocycloalkyl-$C_{1-6}$-alkoxy, cyano, cyano-$C_{1-6}$-alkyl, cyano-$C_{1-6}$-alkoxy, $NR_aR_b$, $NR_cCOR_d$, $NR_cSO_2R_d$, $NR_cSO_2NR_aR_b$, $CONR_aR_b$, $CON(OR_c)R_d$, a heteroaryl group, the aryl or heteroaryl groups being optionally substituted with one or more substituents chosen from fluorine, chlorine and bromine atoms or a group $C_{1-6}$-alkyl, $C_{3-7}$-cycloalkyl, $C_{1-6}$-alkoxy, $C_{1-6}$-fluoroalkyl, $C_{1-6}$-fluoroalkoxy or cyano, the aryl group being chosen from phenyl and naphthyl, and the heteroaryl group being chosen from pyridyl, pyrimidinyl, pyridazinyl, pyrazinyl, triazinyl, pyrrolyl, furyl, thienyl, imidazolyl, oxazolyl, triazolyl, pyrazolyl, isoxazolyl, isothiazolyl, oxadiazolyl, thiadiazolyl, triazolyl, tetrazolyl;

$R_a$ and $R_b$ represent, independently of each other, a hydrogen atom or a group $C_{1-6}$-alkyl, $C_{3-7}$-cycloalkyl or $C_{3-7}$-cycloalkyl-$C_{1-6}$-alkyl, or alternatively they form with the atom that bears them a ring chosen from azetidine, pyrrolidine, piperidine, morpholine, thiomorpholine, azepine and piperazine, this ring being optionally substituted with one or more groups $C_{1-6}$-alkyl, $R_c$ and $R_d$ represent, independently of each other, a hydrogen atom or a group $C_{1-6}$-alkyl, $C_{3-7}$-cycloalkyl or $C_{3-7}$-cycloalkyl-$C_{1-6}$-alkyl.

Among the compounds of general formula (I), the following compounds may be mentioned (IUPAC nomenclature generated with the ACD Name software):

1. $N^2$-tert-butyl-7-phenyl-3,4-dihydropyrrolo[1,2-a]pyrazine-2,8(1H)-dicarboxamide,
2. $N^2$-tert-butyl-7-(4-methoxyphenyl)-3,4-dihydropyrrolo[1,2-a]pyrazine-2,8(1H)-dicarboxamide,
3. $N^2$-tert-butyl-6-methyl-7-phenyl-3,4-dihydropyrrolo[1,2-a]pyrazine-2,8(1H)-dicarboxamide
4. $N^2$-tert-butyl-7-(4-methoxyphenyl)-6-methyl-3,4-dihydropyrrolo[1,2-a]pyrazine-2,8(1H)-dicarboxamide,
5. $N^2$-tert-butyl-6-methyl-7-(4-phenoxyphenyl)-3,4-dihydropyrrolo[1,2-a]pyrazine-2,8(1H)-dicarboxamide,
6. $N^2$-6-di-cyclo-propyl-7-(4-methoxyphenyl)-3,4-dihydropyrrolo[1,2-a]pyrazine-2,8(1H)-dicarboxamide,
7. 6-cyclo-propyl-7-phenyl-$N^2$-(iso-propyl)-3,4-dihydropyrrolo[1,2-a]pyrazine-2,8(1H)-dicarboxamide,
8. 6-cyclo-propyl-7-(4-methoxyphenyl)-$N^2$-(iso-propyl)-3,4-dihydropyrrolo[1,2-a]pyrazine-2,8(1H)-dicarboxamide,
9. 6-cyclo-propyl-7-phenyl-$N^2$-(iso-butyl)-3,4-dihydropyrrolo[1,2-a]pyrazine-2,8(1H)-dicarboxamide,
10. $N^2$-tert-butyl-6-cyclo-propyl-7-phenyl-3,4-dihydropyrrolo[1,2-a]pyrazine-2,8(1H)-dicarboxamide,
11. $N^2$-tert-butyl-6-cyclo-propyl-7-(3-methylphenyl)-3,4-dihydropyrrolo[1,2-a]pyrazine-2,8(1H)-dicarboxamide,
12. $N^2$-tert-butyl-6-cyclo-propyl-7-(4-methylphenyl)-3,4-dihydropyrrolo[1,2-a]pyrazine-2,8(1H)-dicarboxamide,
13. $N^2$-tert-butyl-6-cyclo-propyl-7-[4-(iso-propyl)phenyl]-3,4-dihydropyrrolo[1,2-a]pyrazine-2,8(1H)-dicarboxamide,
14. $N^2$-tert-butyl-7-(4-cyclo-hexylphenyl)-6-cyclo-propyl-3,4-dihydropyrrolo[1,2-a]pyrazine-2,8(1H)-dicarboxamide,
15. 7-(biphenyl-4-yl)-$N^2$-tert-butyl-6-cyclo-propyl-3,4-dihydropyrrolo[1,2-a]pyrazine-2,8(1H)-dicarboxamide,
16. $N^2$-tert-butyl-6-cyclo-propyl-7-[3-(trifluoromethyl)phenyl]-3,4-dihydropyrrolo[1,2-a]pyrazine-2,8(1H)-dicarboxamide,
17. $N^2$-tert-butyl-6-cyclo-propyl-7-[3-(dimethylcarbamoyl)phenyl]-3,4-dihydropyrrolo[1,2-a]pyrazine-2,8(1H)-dicarboxamide,
18. $N^2$-tert-butyl-6-cyclo-propyl-7-[4-(cyclo-propylcarbamoyl)phenyl]-3,4-dihydropyrrolo[1,2-a]pyrazine-2,8(1H)-dicarboxamide,
19. $N^2$-tert-butyl-6-cyclo-propyl-7-[4-(pyrrolidin-1-ylcarbonyl)phenyl]-3,4-dihydropyrrolo[1,2-a]pyrazine-2,8(1H)-dicarboxamide,
20. $N^2$-tert-butyl-6-cyclo-propyl-7-{4-[methoxy(methyl)carbamoyl]phenyl}-3,4-dihydropyrrolo[1,2-a]pyrazine-2,8(1H)-dicarboxamide,
21. $N^2$-tert-butyl-7-(3-cyanophenyl)-6-cyclo-propyl-3,4-dihydropyrrolo[1,2-a]pyrazine-2,8(1H)-dicarboxamide,
22. $N^2$-tert-butyl-7-(4-cyanophenyl)-6-cyclo-propyl-3,4-dihydropyrrolo[1,2-a]pyrazine-2,8(1H)-dicarboxamide,
23. $N^2$-tert-butyl-6-cyclo-propyl-7-[4-(5-methyl-1,3,4-oxadiazol-2-yl)phenyl]-3,4-dihydropyrrolo[1,2-a]pyrazine-2,8(1H)-dicarboxamide,
24. $N^2$-tert-butyl-6-cyclo-propyl-7-[4-(trifluoromethyl)phenyl]-3,4-dihydropyrrolo[1,2-a]pyrazine-2,8(1H)-dicarboxamide,
25. $N^2$-tert-butyl-6-cyclo-propyl-7-(naphthalen-2-yl)-3,4-dihydropyrrolo[1,2-a]pyrazine-2,8(1H)-dicarboxamide,
26. $N^2$-tert-butyl-6-cyclo-propyl-7-{3-[(dimethylsulfamoyl)amino]phenyl}-3,4-dihydropyrrolo[1,2-a]pyrazine-2,8(1H)-dicarboxamide,
27. $N^2$-tert-butyl-6-cyclo-propyl-7-[3-(1H-pyrazol-1-yl)phenyl]-3,4-dihydropyrrolo[1,2-a]pyrazine-2,8(1H)-dicarboxamide,
28. $N^2$-tert-butyl-6-cyclo-propyl-7-[4-(dimethylamino)phenyl]-3,4-dihydropyrrolo[1,2-a]pyrazine-2,8(1H)-dicarboxamide,
29. $N^2$-tert-butyl-6-cyclo-propyl-7-{4-[(methylsulfonyl)amino]phenyl}-3,4-dihydropyrrolo[1,2-a]pyrazine-2,8(1H)-dicarboxamide,
30. $N^2$-tert-butyl-6-cyclo-propyl-7-[4-(morpholin-4-yl)phenyl]-3,4-dihydropyrrolo[1,2-a]pyrazine-2,8(1H)-dicarboxamide,
31. $N^2$-tert-butyl-6-cyclo-propyl-7-[4-(1H-pyrazol-1-yl)phenyl]-3,4-dihydropyrrolo[1,2-a]pyrazine-2,8(1H)-dicarboxamide,
32. $N^2$-tert-butyl-6-cyclo-propyl-7-(3-methoxyphenyl)-3,4-dihydropyrrolo[1,2-a]pyrazine-2,8(1H)-dicarboxamide,
33. $N^2$-tert-butyl-6-cyclo-propyl-7-[3-(cyclo-propylmethoxy)phenyl]-3,4-dihydropyrrolo[1,2-a]pyrazine-2,8(1H)-dicarboxamide,
34. 7-[3-(benzyloxy)phenyl]-$N^2$-tert-butyl-6-cyclo-propyl-3,4-dihydropyrrolo[1,2-a]pyrazine-2,8(1H)-dicarboxamide,
35. $N^2$-tert-butyl-6-cyclo-propyl-7-[3-(trifluoromethoxy)phenyl]-3,4-dihydropyrrolo[1,2-a]pyrazine-2,8(1H)-dicarboxamide,
36. $N^2$-tert-butyl-6-cyclo-propyl-7-[4-(methoxy)phenyl]-3,4-dihydropyrrolo[1,2-a]pyrazine-2,8(1H)-dicarboxamide,
37. $N^2$-tert-butyl-6-cyclo-propyl-7-[4-(cyclo-propylmethoxy)phenyl]-3,4-dihydropyrrolo[1,2-a]pyrazine-2,8(1H)-dicarboxamide,
38. 7-(4-butoxyphenyl)-$N^2$-tert-butyl-6-cyclo-propyl-3,4-dihydropyrrolo[1,2-a]pyrazine-2,8(1H)-dicarboxamide,
39. $N^2$-tert-butyl-6-cyclo-propyl-7-(4-phenoxyphenyl)-3,4-dihydropyrrolo[1,2-a]pyrazine-2,8(1H)-dicarboxamide,
40. 7-[4-(benzyloxy)phenyl]-$N^2$-tert-butyl-6-cyclo-propyl-3,4-dihydropyrrolo[1,2-a]pyrazine-2,8(1H)-dicarboxamide, 41. $N^2$-tert-butyl-6-cyclo-propyl-7-{4-[(4-fluorobenzyl)oxy]phenyl}-3,4-dihydropyrrolo[1,2-a]pyrazine-2,8(1H)-dicarboxamide,
42. $N^2$-tert-butyl-7-{3-chloro-4-[(4-fluorobenzyl)oxy]phenyl}-6-cyclo-propyl-3,4-dihydropyrrolo[1,2-a]pyrazine-2,8(1H)-dicarboxamide,
43. $N^2$-tert-butyl-7-[4-(cyanomethoxy)phenyl]-6-cyclo-propyl-3,4-dihydropyrrolo[1,2-a]pyrazine-2,8(1H)-dicarboxamide,
44. $N^2$-tert-butyl-6-cyclo-propyl-7-[4-(trifluoromethoxy)phenyl]-3,4-dihydropyrrolo[1,2-a]pyrazine-2,8(1H)-dicarboxamide,
45. $N^2$-tert-butyl-6-cyclo-propyl-7-(2-fluorophenyl)-3,4-dihydropyrrolo[1,2-a]pyrazine-2,8(1H)-dicarboxamide,
46. $N^2$-tert-butyl-6-cyclo-propyl-7-(3-fluorophenyl)-3,4-dihydropyrrolo[1,2-a]pyrazine-2,8(1H)-dicarboxamide,
47. $N^2$-tert-butyl-6-cyclo-propyl-7-(4-fluorophenyl)-3,4-dihydropyrrolo[1,2-a]pyrazine-2,8(1H)-dicarboxamide,
48. $N^2$-tert-butyl-6-cyclo-propyl-7-[4-(methylsulfanyl)phenyl]-3,4-dihydropyrrolo[1,2-a]pyrazine-2,8(1H)-dicarboxamide,
49. $N^2$-cyclo-hexyl-6-cyclo-propyl-7-phenyl-3,4-dihydropyrrolo[1,2-a]pyrazine-2,8(1H)-dicarboxamide,
50. $N^2$-(cyclo-hexylmethyl)-6-cyclo-propyl-7-phenyl-3,4-dihydropyrrolo[1,2-a]pyrazine-2,8(1H)-dicarboxamide,
51. $N^2$-[1,1'-bi(cyclo-propyl)-1-yl]-6-cyclo-propyl-7-(4-methoxyphenyl)-3,4-dihydropyrrolo[1,2-a]pyrazine-2,8(1H)-dicarboxamide,
52. 6-cyclo-propyl-7-phenyl-$N^2$-(2,4,4-trimethylpentan-2-yl)-3,4-dihydropyrrolo[1,2-a]pyrazine-2,8(1H)-dicarboxamide,
53. 6-cyclo-propyl-$N^2$-(hexahydro-2,5-methanopentalen-3a(1H)-yl)-7-(4-methoxyphenyl)-3,4-dihydropyrrolo[1,2-a]pyrazine-2,8(1H)-dicarboxamide,
54. $N^2$-(adamantan-1-yl)-6-cyclo-propyl-7-phenyl-3,4-dihydropyrrolo[1,2-a]pyrazine-2,8(1H)-dicarboxamide,
55. $N^2$-(adamantan-1-yl)-6-cyclo-propyl-7-(4-methoxyphenyl)-3,4-dihydropyrrolo[1,2-a]pyrazine-2,8(1H)-dicarboxamide,
56. 6-cyclo-propyl-7-(4-methoxyphenyl)-$N^2$-(tetrahydro-2H-pyran-4-yl)-3,4-dihydropyrrolo[1,2-a]pyrazine-2,8(1H)-dicarboxamide,
57. 6-cyclo-propyl-$N^2$-(1-methoxy-2-methylpropan-2-yl)-7-(4-methoxyphenyl)-3,4-dihydropyrrolo[1,2-a]pyrazine-2,8(1H)-dicarboxamide,
58. $N^2$-tert-butyl-6-fluoro-7-phenyl-3,4-dihydropyrrolo[1,2-a]pyrazine-2,8(1H)-dicarboxamide,
59. 6-chloro-$N^2$-iso-butyl-7-phenyl-3,4-dihydropyrrolo[1,2-a]pyrazine-2,8(1H)-dicarboxamide,
60. $N^2$-tert-butyl-6-chloro-7-phenyl-3,4-dihydropyrrolo[1,2-a]pyrazine-2,8(1H)-dicarboxamide,
61. $N^2$-tert-butyl-6-chloro-7-(3-methylphenyl)-3,4-dihydropyrrolo[1,2-a]pyrazine-2,8(1H)-dicarboxamide,
62. $N^2$-tert-butyl-6-chloro-7-(3-methoxyphenyl)-3,4-dihydropyrrolo[1,2-a]pyrazine-2,8(1H)-dicarboxamide,
63. $N^2$-tert-butyl-6-chloro-7-[3-(trifluoromethoxy)phenyl]-3,4-dihydropyrrolo[1,2-a]pyrazine-2,8(1H)-dicarboxamide,
64. $N^2$-tert-butyl-6-chloro-7-(4-methoxyphenyl)-3,4-dihydropyrrolo[1,2-a]pyrazine-2,8(1H)-dicarboxamide,
65. $N^2$-tert-butyl-6-chloro-7-(3-cyanophenyl)-3,4-dihydropyrrolo[1,2-a]pyrazine-2,8(1H)-dicarboxamide,
66. $N^2$-tert-butyl-6-chloro-7-[3-(trifluoromethyl)phenyl]-3,4-dihydropyrrolo[1,2-a]pyrazine-2,8(1H)-dicarboxamide,
67. $N^2$-tert-butyl-6-chloro-7-(3-fluorophenyl)-3,4-dihydropyrrolo[1,2-a]pyrazine-2,8(1H)-dicarboxamide,
68. 6-chloro-$N^2$-(cyclo-propylmethyl)-7-phenyl-3,4-dihydropyrrolo[1,2-a]pyrazine-2,8(1H)-dicarboxamide,
69. 6-chloro-$N^2$-(3-methylbutyl)-7-phenyl-3,4-dihydropyrrolo[1,2-a]pyrazine-2,8(1H)-dicarboxamide,
70. 6-chloro-$N^2$-(2,2-dimethylpropyl)-7-phenyl-3,4-dihydropyrrolo[1,2-a]pyrazine-2,8(1H)-dicarboxamide,
71. 6-chloro-$N^2$-(2-ethylbutyl)-7-phenyl-3,4-dihydropyrrolo[1,2-a]pyrazine-2,8(1H)-dicarboxamide,
72. 6-chloro-$N^2$-(3,3-dimethylbutyl)-7-phenyl-3,4-dihydropyrrolo[1,2-a]pyrazine-2,8(1H)-dicarboxamide,
73. 6-chloro-7-(3-fluorophenyl)-$N^2$-(3-hydroxy-2,2-dimethylpropyl)-3,4-dihydropyrrolo[1,2-a]pyrazine-2,8(1H)-dicarboxamide,
74. 6-chloro-$N^2$-(3-hydroxy-2,2-dimethylpropyl)-7-(3-trifluoromethyl-phenyl)-3,4-dihydropyrrolo[1,2-a]pyrazine-2,8(1H)-dicarboxamide,
75. 6-chloro-7-(3-fluorophenyl)-$N^2$-{[1-(hydroxymethyl)cyclo-propyl]methyl}-3,4-dihydropyrrolo[1,2-a]pyrazine-2,8(1H)-dicarboxamide,
76. 6-chloro-7-phenyl-$N^2$-(2,2,2-trifluoroethyl)-3,4-dihydropyrrolo[1,2-a]pyrazine-2,8(1H)-dicarboxamide,
77. 6-chloro-7-(3-fluorophenyl)-$N^2$-(2,2,2-trifluoroethyl)-3,4-dihydropyrrolo[1,2-a]pyrazine-2,8(1H)-dicarboxamide,
78. 6-chloro-7-(3-fluorophenyl)-$N^2$-[(2S)-1,1,1-trifluoropropan-2-yl]-3,4-dihydropyrrolo[1,2-a]pyrazine-2,8(1H)-dicarboxamide,
79. 6-chloro-7-(3-fluorophenyl)-$N^2$-(1,1,1-trifluoro-2-methylpropan-2-yl)-3,4-dihydropyrrolo[1,2-a]pyrazine-2,8(1H)-dicarboxamide,
80. 6-chloro-7-(3-fluorophenyl)-$N^2$-(3,3,3-trifluoropropyl)-3,4-dihydropyrrolo[1,2-a]pyrazine-2,8(1H)-dicarboxamide,
81. 6-chloro-7-(3-fluorophenyl)-$N^2$-(4,4,4-trifluorobutyl)-3,4-dihydropyrrolo[1,2-a]pyrazine-2,8(1H)-dicarboxamide,
82. 6-chloro-$N^2$-cyclo-hexyl-7-phenyl-3,4-dihydropyrrolo[1,2-a]pyrazine-2,8(1H)-dicarboxamide,
83. trans-6-chloro-7-(3-fluorophenyl)-$N^2$-(4-hydroxy-cyclo-hexyl)-3,4-dihydropyrrolo[1,2-a]pyrazine-2,8(1H)-dicarboxamide,
84. trans-6-chloro-7-(3-fluorophenyl)-$N^2$-(4-hydroxy-4-methyl-cyclo-hexyl)-3,4-dihydropyrrolo[1,2-a]pyrazine-2,8(1H)-dicarboxamide,
85. trans-6-chloro-7-(3-fluorophenyl)-$N^2$-(4-hydroxy-4-trifluoromethyl-cyclo-hexyl)-3,4-dihydropyrrolo[1,2-a]pyrazine-2,8(1H)-dicarboxamide,
86. trans-6-chloro-7-(3-fluorophenyl)-$N^2$-(4-methoxyiminocyclohexyl)-3,4-dihydropyrrolo[1,2-a]pyrazine-2,8(1H)-dicarboxamide,
87. trans-6-chloro-7-(3-fluorophenyl)-$N^2$-(4-tert-butyloxyimino-cyclohexyl)-3,4-dihydropyrrolo[1,2-a]pyrazine-2,8(1H)-dicarboxamide,
88. $N^2$-(bicyclo[2.2.1]hept-2-yl)-6-chloro-7-phenyl-3,4-dihydropyrrolo[1,2-a]pyrazine-2,8(1H)-dicarboxamide,
89. 6-chloro-$N^2$-(4,4-difluoro-cyclo-hexyl)-7-(3-fluorophenyl)-3,4-dihydropyrrolo[1,2-a]pyrazine-2,8(1H)-dicarboxamide,
90. 6-chloro-7-(3-fluorophenyl)-$N^2$-(oxetan-3-yl)-3,4-dihydropyrrolo[1,2-a]pyrazine-2,8(1H)-dicarboxamide,
91. 6-chloro-7-(3-fluorophenyl)-$N^2$-(3-methyl-oxetan-3-ylmethyl)-3,4-dihydropyrrolo[1,2-a]pyrazine-2,8(1H)-dicarboxamide,
92. 6-chloro-7-phenyl-$N^2$-(tetrahydrofuran-3-yl)-3,4-dihydropyrrolo[1,2-a]pyrazine-2,8(1H)-dicarboxamide,
93. 6-chloro-7-phenyl-$N^2$-(tetrahydro-2H-pyran-4-yl)-3,4-dihydropyrrolo[1,2-a]pyrazine-2,8(1H)-dicarboxamide, 94. 6-chloro-7-(3-methylphenyl)-N²-(tetrahydro-2H-pyran-4-yl)-3,4-dihydropyrrolo[1,2-a]pyrazine-2,8(1H)-dicarboxamide,
95. 6-chloro-7-(3-cyanophenyl)-N²-(tetrahydro-2H-pyran-4-yl)-3,4-dihydropyrrolo[1,2-a]pyrazine-2,8(1H)-dicarboxamide,
96. 6-chloro-N²-(tetrahydro-2H-pyran-4-yl)-7-[3-(trifluoromethyl)phenyl]-3,4-dihydropyrrolo[1,2-a]pyrazine-2,8(1H)-dicarboxamide,
97. 6-chloro-N²-(tetrahydro-2H-pyran-4-yl)-7-[3-(trifluoromethoxy)phenyl]-3,4-dihydropyrrolo[1,2-a]pyrazine-2,8(1H)-dicarboxamide,
98. 6-chloro-7-(3-fluorophenyl)-N²-(tetrahydro-2H-pyran-4-yl)-3,4-dihydropyrrolo[1,2-a]pyrazine-2,8(1H)-dicarboxamide,
99. 6-chloro-7-(3-fluorophenyl)-N²-(2,2-dimethyl-tetrahydro-2H-pyran-4-yl)-3,4-dihydropyrrolo[1,2-a]pyrazine-2,8(1H)-dicarboxamide,
100. cis-6-chloro-N²-(2,6-dimethyl-tetrahydro-2H-pyran-4-yl)-7-(3-fluorophenyl)-3,4-dihydropyrrolo[1,2-a]pyrazine-2,8(1H)-dicarboxamide,
101. 6-chloro-N²-(1,1-dioxydotetrahydrothiophen-3-yl)-7-phenyl-3,4-dihydropyrrolo[1,2-a]pyrazine-2,8(1H)-dicarboxamide,
102. 6-chloro-N²-(1,1-dioxydotetrahydrothiophen-3-yl)-7-(3-fluorophenyl)-3,4-dihydropyrrolo[1,2-a]pyrazine-2,8(1H)-dicarboxamide,
103. 6-chloro-N²-(1,1-dioxydotetrahydro-2H-thiopyran-4-yl)-7-(3-fluorophenyl)-3,4-dihydropyrrolo[1,2-a]pyrazine-2,8(1H)-dicarboxamide,
104. 6-bromo-7-(3-fluorophenyl)-N²-tert-butyl-3,4-dihydropyrrolo[1,2-a]pyrazine-2,8(1H)-dicarboxamide,
105. 6-cyano-7-(3-fluorophenyl)-N²-(tert-butyl)-3,4-dihydropyrrolo[1,2-a]pyrazine-2,8(1H)-dicarboxamide,
106. 6-cyano-7-(3-fluorophenyl)-N²-((2S)-1,1,1-trifluoropropan-2-yl)-3,4-dihydropyrrolo[1,2-a]pyrazine-2,8(1H)-dicarboxamide,
107. 6-cyano-7-(3-fluorophenyl)-N²-(1,1,1-trifluoro-2-methylpropan-2-yl)-3,4-dihydropyrrolo[1,2-a]pyrazine-2,8(1H)-dicarboxamide,
108. 6-cyano-7-(3-fluorophenyl)-N²-(4,4,4-trifluoro-butyl)-3,4-dihydropyrrolo[1,2-a]pyrazine-2,8(1H)-dicarboxamide,
109. 6-cyano-7-(3-fluorophenyl)-N²-(tetrahydro-2H-pyran-4-yl)-3,4-dihydropyrrolo[1,2-a]pyrazine-2,8(1H)-dicarboxamide,
110. 6-cyano-N²-(4,4-difluoro-cyclohexyl)-7-(3-fluorophenyl)-3,4-dihydropyrrolo[1,2-a]pyrazine-2,8(1H)-dicarboxamide.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

Some of the compounds of formula (I) may exist in the form of bases or of acid-addition salts. Such addition salts form part of the invention. These salts are advantageously prepared with pharmaceutically acceptable acids, but the salts of other acids that are useful, for example, for purification or isolation of the compounds of formula (I) also form part of the invention.

In the context of the invention, the following definitions apply:
$C_{t-z}$ where t and z may take values from 1 to 7, carbon-based chain possibly containing from t to z carbon atoms, for example $C_{1-7}$ a carbon-based chain which may contain from 1 to 7 carbon atoms;

alkyl, a linear or branched saturated aliphatic group; for example a group $C_{1-6}$-alkyl represents a linear or branched carbon-based chain of 1 to 6 carbon atoms, for example a methyl, ethyl, propyl, isopropyl, butyl, isobutyl, tert-butyl, pentyl or hexyl;

cycloalkyl, a fused, bridged or spiro cyclic or polycyclic alkyl group, for example it may be a group from among:
  $C_{3-10}$-cycloalkyl representing a cyclic carbon-based group of 3 to 10 carbon atoms, such as a cyclopropyl, cyclobutyl, cyclopentyl, cyclohexyl or cycloheptyl,
  fused bicyclic $C_{4-10}$-cycloalkyl representing a fused bicyclic carbon-based group of 4 to 10 carbon atoms, such as a bicyclo[1.1.0]butane, bicyclo[3.1.0]hexane group, bicyclo[3.2.0]heptane or bicyclo[3.3.0]octane,
  bridged bicyclic $C_{5-10}$-cycloalkyl representing a bridged bicyclic carbon-based group of 5 to 10 carbon atoms, such as a bicyclo[1.1.1]pentane or a bicyclo[2.2.1]heptane,
  spiro bicyclic $C_{5-10}$-cycloalkyl representing a spiro bicyclic carbon-based group of 5 to 10 carbon atoms, such as a spiro[2.2]pentane or a spiro[4.4]nonane,
  tricyclic $C_{4-10}$-cycloalkyl representing a tricyclic carbon-based group of 4 to 10 carbon atoms, such as a tricyclo[1.1.0.0$^{2.4}$]butane, a tricyclo-[3.3.3.0$^{3.7}$]nonane or a tricyclo[3.3.3.1$^{3.7}$]decane;

hydroxyl, a group —OH;
hydroxyalkyl, an alkyl group in which a hydrogen atom has been replaced with a hydroxyl group;
alkyloxy, a group —O-alkyl;
alkylthio, a group —S-alkyl;
fluoroalkyl, an alkyl group in which one or more hydrogen atoms have been replaced with a fluorine atom;
fluoroalkyloxy, an alkyloxy group in which one or more hydrogen atoms have been replaced with a fluorine atom;
fluorocycloalkyl, a cycloalkyl group in which one or more hydrogen atoms have been replaced with a fluorine atom;
a heterocyclic group, a saturated carbon-based cyclic group comprising at least one heteroatom such as oxygen or sulfur or the oxide or dioxide forms thereof, for example a group from among oxetanyl, tetrahydrofuryl, tetrahydro-2H-pyranyl, oxepanyl, thietanyl, tetrahydrothiophenyl, tetrahydro-2H-thiopyranyl, thiepanyl, 1,1-dioxydothietanyl, 1,1-dioxydotetrahydrothiophenyl, 1,1-dioxydotetrahydro-2H-thiopyranyl and 1,1-dioxydothiepanyl;
heteroaryl, an aromatic carbon-based cyclic group comprising at least one heteroatom such as nitrogen, oxygen or sulfur, for example a group from among pyridyl, pyrimidinyl, pyridazinyl, pyrazinyl, triazinyl, pyrrolyl, furyl, thienyl, imidazolyl, oxazolyl, thiazolyl, pyrazolyl, isoxazolyl, isothiazolyl, oxadiazolyl, thiadiazolyl, triazolyl and tetrazolyl;
a halogen atom, a fluorine, chlorine, bromine or iodine atom;
aryl, a monocyclic or bicyclic aromatic group comprising between 6 and 10 carbon atoms, for example a phenyl or naphthyl group;
aryloxy, a group —O-aryl.

For the purposes of the present invention, it should be noted that the terms "ranging from . . . to . . . " and "between . . . and . . . " mean that the limits are also included.

In accordance with the invention, the compounds of general formula (I) may be prepared according to the general process described in Scheme 1 below:

SCHEME 1

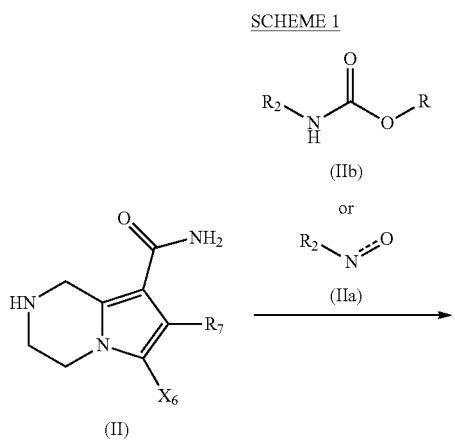

or alternatively
with a compound of formula

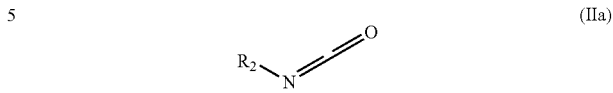

in which $R_2$ is as defined previously in the general formula (I) defined above, in an aprotic solvent such as dichloromethane and optionally in the presence of an organic amine such as triethylamine.

The compounds of general formula (I) may also be prepared according to the process described in Scheme 2 below.

SCHEME 2

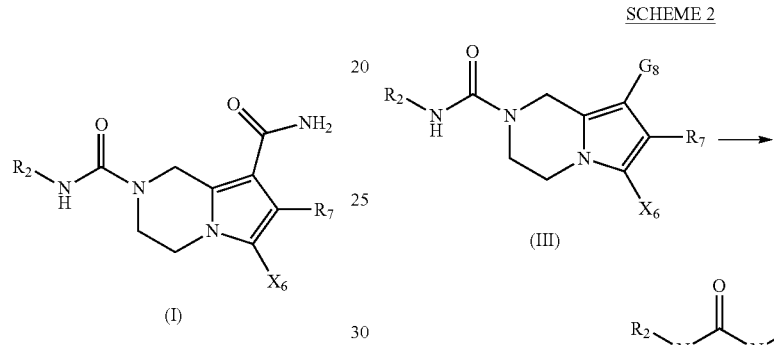

Thus, another subject of the invention is directed towards a process for preparing compounds of formula (I) according to the invention, comprising the step that consists in reacting a 1,2,3,4-tetrahydropyrrolo[1,2-a]pyrazine-8-carboxamide derivative, which is a compound of formula (II) below:

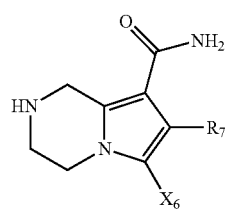

in which $R_7$ and $X_6$ are as defined previously in the general formula (I) defined above, with a compound of formula

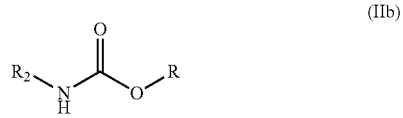

in which $R_2$ is as defined previously in the general formula (I) defined above and R represents a group such as phenyl, pentafluorophenyl or 4-nitrophenyl, in an aprotic solvent such as acetonitrile and in the presence of a mineral base such as sodium carbonate;

Thus, yet another subject of the invention is directed towards a process for preparing the compounds of formula (I) according to the invention, comprising the step that consists in hydrating the nitrile function of a 1,2,3,4-tetrahydropyrrolo[1,2-a]pyrazine derivative of general formula (III),

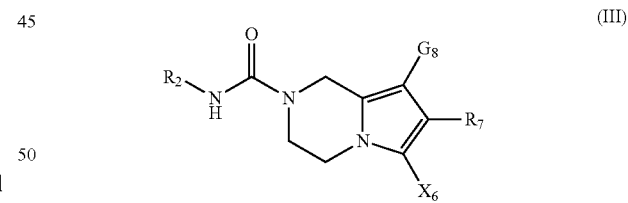

in which $R_2$, $X_6$ and $R_7$ are as defined previously and $G_8$ represents a nitrile group. This transformation may be performed, for example, in the presence of aqueous hydrogen peroxide solution and a base such as sodium hydroxide.

Still as illustrated in Scheme 2, the 3,4-dihydropyrrolo[1,2-a]pyrazine-2,8(1H)-dicarboxamide derivatives of general formula (I) in which $R_2$, $X_6$ and $R_7$ are as defined above may also be prepared from a 1,2,3,4-tetrahydropyrrolo[1,2-a]pyrazine derivative of general formula (III), in which $R_2$, $X_6$ and $R_7$ are as defined above and $G_8$ represents an alkyl carboxylate group, preferentially a methyl or ethyl carboxylate. The 3,4-dihydropyrrolo[1,2-a]pyrazine-2,8(1H)-dicarboxamide derivatives of general formula (I) as defined above are then prepared by saponification of the alkyl carboxylate group of the derivative of general formula (III) to the corresponding carboxylic acid, followed by amidation of this carboxylic acid function. This amidation may be performed, for example, by activation of the acid using a coupling agent such as carbonyldiimidazole in dichloromethane and treatment of the activated acid using aqueous ammonia.

The compounds of general formula (I) may also be prepared according to the process described in Scheme 3 below.

SCHEME 3

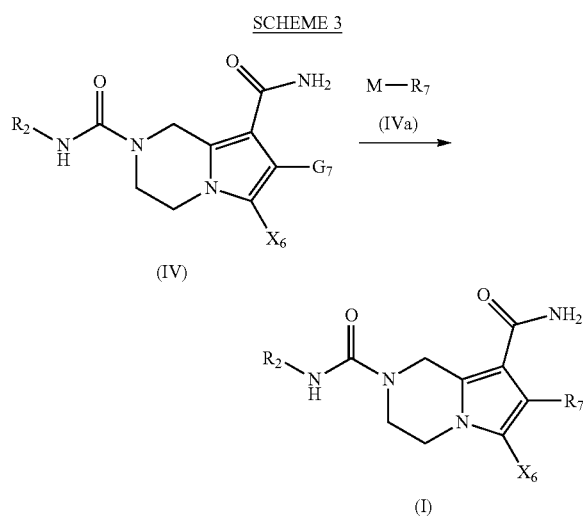

Thus, another subject of the invention is directed towards a process for preparing compounds of formula (I) according to the invention, comprising the step that consists in reacting a 1,2,3,4-tetrahydropyrrolo[1,2-a]pyrazine-2-carboxamide derivative of general formula (IV)

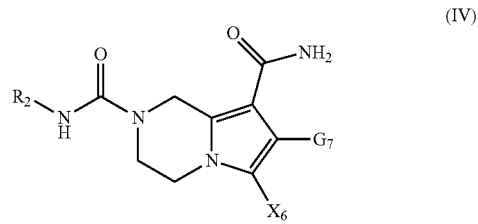

in which $R_2$ and $X_6$ are as defined above and $G_7$ represents a chlorine, bromine or iodine atom, preferentially a bromine atom, via metallo-catalysed coupling, such as the Suzuki reaction with a derivative of general formula M-$R_7$ (IVa) in which $R_7$ is as defined above and M represents a dihydroxyboryl or dialkyloxyboryl group, usually a 4,4,5,5-tetramethyl-1,3,2-dioxaborolan-2-yl group. This reaction may be performed, for example, in the presence of caesium carbonate or sodium carbonate, and 1,1'-bis(diphenylphosphino)ferrocenedichloropalladium (II) in a mixture of tetrahydrofuran and water.

More specifically, the 3,4-dihydropyrrolo[1,2-a]pyrazine-2,8(1H)-dicarboxamide derivatives of general formula (I) in which $R_2$ and $R_7$ are as defined above and $X_6$ represents a hydrogen atom may also be prepared from a 3,4-dihydropyrrolo[1,2-a]pyrazine-2,8(1H)-dicarboxamide derivative of general formula (I) in which $R_2$ and $R_7$ are as defined above and $X_6$ represents a chlorine atom. This transformation may be performed, for example, via a hydrogenation reaction in the presence of a catalyst such as palladium-on-charcoal.

Preparation of the Precursors (II)

The 1,2,3,4-tetrahydropyrrolo[1,2-a]pyrazine-8-carboxamide derivatives of general formula (II) as defined above and for which $X_6$ represents a group $C_{1-6}$-alkyl, $C_{3-7}$-cycloalkyl, $C_{3-7}$-cycloalkyl-$C_{1-6}$-alkyl or $C_{1-6}$-fluoroalkyl may be prepared in 5 steps (Scheme 4) starting with a piperazine-1,3-dicarboxylate derivative of general formula (IX) in which $X_6$ represents a group $C_{1-6}$-alkyl, $C_{3-7}$-cycloalkyl, $C_{3-7}$-cycloalkyl-$C_{1-6}$-alkyl or $C_{1-6}$-fluoroalkyl and PG represents an acid-labile protecting group for the amine function such as a tert-butyloxycarbonyl.

According to the method described in document WO 03/024967, treatment of the sodium or potassium salt of a piperazine-1,3-dicarboxylate derivative of general formula (IX) using a tosyl chloride followed by treatment with 2-chloroacrylonitrile and an organic base such as triethylamine in a solvent such as dichloromethane leads to a 8-cyano-3,4-dihydro-1H-pyrrolo[1,2-a]pyrazine derivative of general formula (VIII) in which $X_6$ and PG are as defined above.

These derivatives of general formula (VIII) are then transformed into 8-carbamoyl-3,4-dihydro-1H-pyrrolo[1,2-a]pyrazine derivatives of general formula (VII) in which $X_6$ and PG are as defined above, by treatment with aqueous hydrogen peroxide solution and a mineral base such as aqueous sodium hydroxide in a solvent such as methanol.

The 8-carbamoyl-3,4-dihydro-1H-pyrrolo[1,2-a]pyrazine derivatives of general formula (VII) as defined above are then transformed into derivatives of general formula (VI) in which $X_6$ and PG are as defined above and $G_7$ represents a chlorine, bromine or iodine atom, more particularly bromine, by regioselective halogenation. In the case of bromine, this halogenation is performed, for example, by treatment with N-bromosuccinimide in a solvent such as dichloromethane.

SCHEME 4

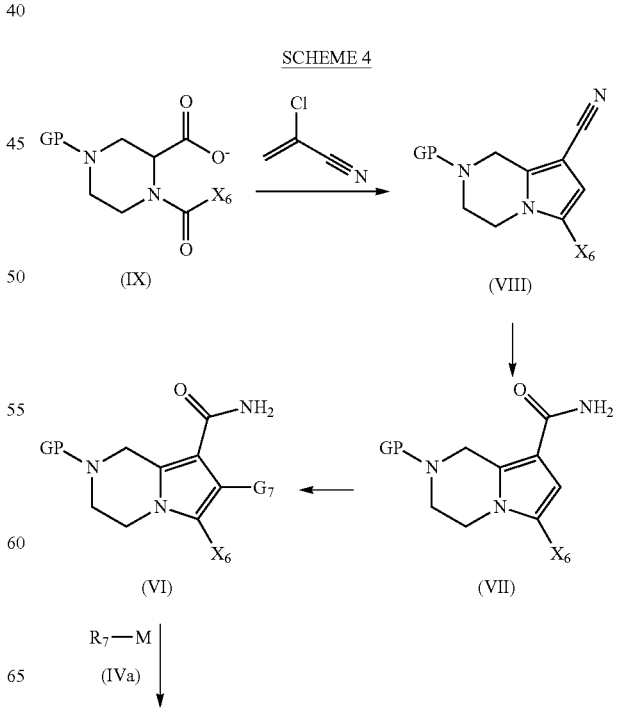

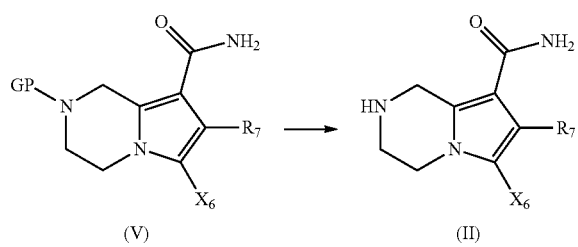

(V) → (II)

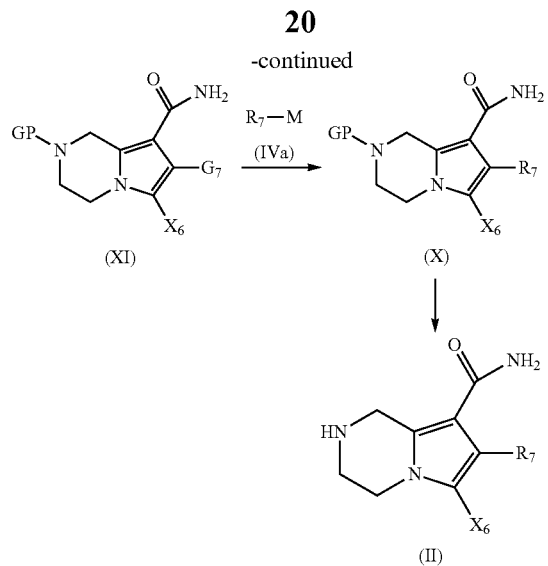

(XI) → (X) → (II)

The derivatives of general formula (VI) as defined above are transformed into derivatives of general formula (V) in which $X_6$ and PG are as defined above and $R_7$ is as defined in the general formula (I) by metallo-catalysed coupling, for example by Suzuki reaction with a derivative of general formula (IVa) as defined previously. This reaction may be performed, for example in the presence of caesium carbonate and 1,1'-bis(diphenylphosphino)ferrocenedichloropalladium (II) in a mixture of tetrahydrofuran and water.

The compound of general formula (II) is then obtained from the 8-carbamoyl-3,4-dihydro-1H-pyrrolo[1,2-a] derivative of general formula (V) by removal of the protecting group PG, for example by treatment with trimethylsilyl chloride in a solvent such as methanol when PG represents tert-butyloxycarbonyl.

The 1,2,3,4-tetrahydropyrrolo[1,2-a]pyrazine-8-carboxamide derivatives of general formula (II) as defined above in which $X_6$ represents a chlorine atom may be prepared in 6 steps (Scheme 5) starting with a piperazine-1,3-dicarboxylate derivative of general formula (XV) in which PG represents an acid-labile protecting group for the amine function such as a tert-butyloxycarbonyl.

SCHEME 5

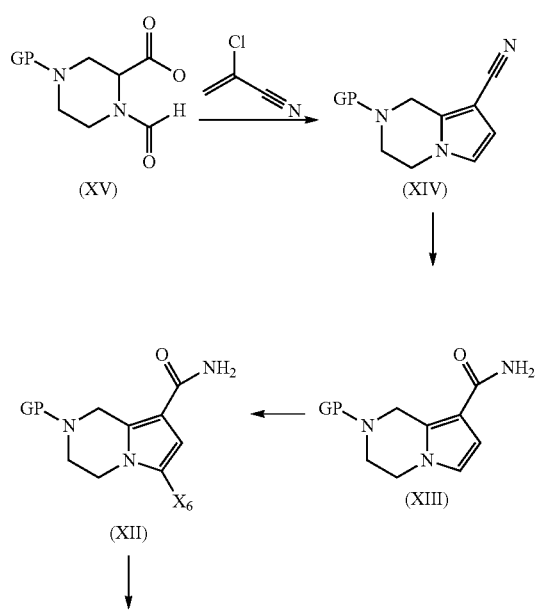

(XV) → (XIV) → (XIII) → (XII)

According to the method described in document WO 03/024 967, treatment with the sodium or potassium salt of a piperazine-1,3-dicarboxylate derivative of general formula (XV) using tosyl chloride followed by treatment with 2-chloroacrylonitrile and an organic base such as triethylamine in a solvent such as dichloromethane leads to a 8-cyano-3,4-dihydro-1H-pyrrolo[1,2-a]pyrazine derivative of general formula (XIV) in which PG is as defined above.

These 8-cyano-3,4-dihydro-1H-pyrrolo[1,2-a]pyrazine derivatives of general formula (XIV) as defined above are then transformed into 8-carbamoyl-3,4-dihydro-1H-pyrrolo[1,2-a]pyrazine derivatives of general formula (XIII) in which PG is as defined above by treatment with aqueous hydrogen peroxide solution and a mineral base such as aqueous sodium hydroxide in a solvent such as methanol.

The derivatives of general formula (XIII) as defined above are then transformed into 6-chloro-8-carbamoyl-3,4-dihydro-1H-pyrrolo[1,2-a]pyrazine derivatives of general formula (XII) in which PG is as defined above and $X_6$ represents a chlorine atom by regioselective chlorination. This halogenation is performed, for example, by treatment with N-chlorosuccinimide in a solvent such as dichloromethane.

The derivatives of general formula (XII) as defined above are then transformed into 7-bromo-6-chloro-8-carbamoyl-3,4-dihydro-1H-pyrrolo[1,2-a]pyrazine derivatives of general formula (XI) in which GP, $X_6$ and $G_7$ are as defined above by regioselective bromination. This halogenation is performed, for example, by treatment with N-bromosuccinimide in a solvent mixture such as dichloromethane and ethyl acetate.

The derivatives of general formula (XI) as defined above are transformed into 6-chloro-8-carbamoyl-3,4-dihydro-1H-pyrrolo[1,2-a]pyrazine derivatives of general formula (X) in which PG is as defined above and $R_7$ is as defined in the general formula, by metallo-catalysed coupling, for example by Suzuki reaction with a derivative of general formula (IVa) as defined previously. This reaction may be performed, for example, in the presence of caesium carbonate and 1,1'-bis(diphenylphosphino)ferrocenedichloropalladium (II) in a mixture of tetrahydrofuran and water.

The compound of general formula (II) for which $X_6$ represents a chlorine atom is then obtained from derivatives of general formula (X) by removal of the protecting group PG, for example by treatment with trimethylsilyl chloride in a solvent such as methanol or by treatment with an acid such as trifluoroacetic acid in a solvent such as dichloromethane when PG represents a tert-butyloxycarbonyl group.

The 1,2,3,4-tetrahydropyrrolo[1,2-a]pyrazine-8-carboxamide derivatives of general formula (II) as defined above and for which $X_6$ represents a fluorine or chlorine atom may be prepared in 6 steps starting with a pyrrole derivative of general formula (XX) for which $R_7$ is as defined above and $G_8$ represents a nitrile group or an alkyl carboxylate group, preferentially a methyl or ethyl carboxylate (Scheme 6).

The pyrrole derivatives of general formula (XX) are thus regioselectively halogenated in position 2 by treatment with N-chlorosuccinimide in a solvent such as tetrahydrofuran or using 1-chloromethyl-4-fluoro-1,4-diazoniabicyclo[2.2.2]octane (SelectFluor) in a solvent such as acetonitrile to give a derivative of general formula (IXX) for which $R_7$ and $G_8$ are as defined above and $X_6$ represents a fluorine or chlorine atom.

SCHEME 6

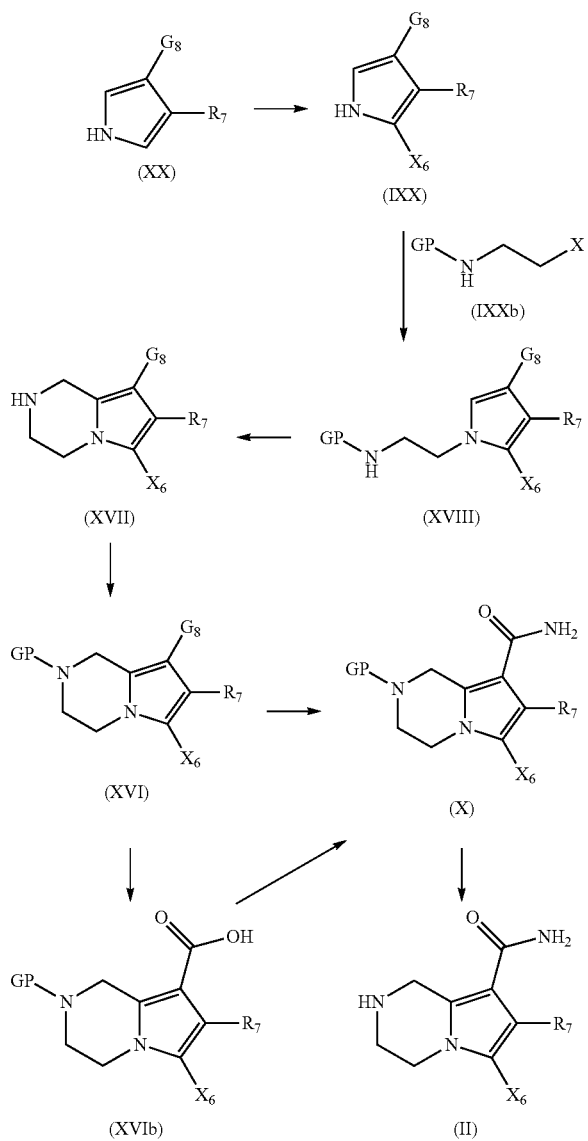

The pyrrole derivatives of general formula (IXX) are then alkylated using aminoethyl derivatives of general formula (IXXb) for which X constitutes a leaving group, for example a chlorine atom and PG constitutes an acid-labile protecting group such as tert-butyloxycarbonyl, to give a pyrrole derivative of general formula (XVIII) for which $X_6$ represents a fluorine or chlorine atom, $R_7$ and $G_8$ are as defined above and PG constitutes an acid-labile protecting group such as tert-butyloxycarbonyl. This alkylation reaction is performed, for example, in the presence of a mineral base such as sodium hydroxide and a phase-transfer catalyst such as tetrabutylammonium hydrogen sulfate, and in a solvent such as acetonitrile.

The pyrrole derivatives of general formula (XVIII) are treated in acidic medium in the presence of formaldehyde or paraformaldehyde to give, after deprotection of the protecting group PG and cyclization, the 1,2,3,4-tetrahydropyrrolo[1,2-a]pyrazine derivatives of general formula (XVII) for which $X_6$ represents a fluorine or chlorine atom, while $R_7$ and $G_8$ are as defined above. This step is performed, for example, using aqueous hydrochloric acid solution and formaldehyde or paraformaldehyde.

A subject of the present invention relates to a process for preparing compounds of formula (XVII) for which $X_6$ represents a fluorine or chlorine atom, while $R_7$ is as defined previously in the general formula (I), and $G_8$ represents a nitrile group or an alkyl carboxylate group, such as a methyl or ethyl carboxylate, comprising the step that consists in reacting a pyrrole derivative, which is a compound of formula (XVIII) with an acidic solution, for example an aqueous hydrochloric acid solution, and formaldehyde or paraformaldehyde, to give the 1,2,3,4-tetrahydropyrrolo[1,2-a]pyrazine derivatives of general formula (XVII) in which $X_6$ represents a fluorine or chlorine atom, while $R_7$ is as defined previously in the general formula (I), and $G_8$ represents a nitrile group or an alkyl carboxylate group, such as a methyl or ethyl carboxylate.

The 1,2,3,4-tetrahydropyrrolo[1,2-a]pyrazine derivatives of general formula (XVII) are then protected as 1,2,3,4-tetrahydropyrrolo[1,2-a]pyrazine derivatives of general formula (XVI) for which $X_6$ represents a fluorine or chlorine atom, while $R_7$ and $G_8$ are as defined above and PG represents an acid-labile protecting group, for example tert-butyloxycarbonyl. The reaction is then performed by treatment with di-tert-butyl dicarbonate in a solvent such as dichloromethane.

Depending on the nature of the group $G_8$, the process may be performed according to one of the alternatives described below.

The 1,2,3,4-tetrahydropyrrolo[1,2-a]pyrazine derivatives of general formula (XVI), for which $X_6$ represents a fluorine or chlorine atom, while $R_7$ and PG are as defined above and $G_8$ represents a nitrile group, are transformed into 8-carbamoyl-1,2,3,4-tetrahydropyrrolo[1,2-a]pyrazine derivatives of general formula (X) for which $X_6$ represents a fluorine or chlorine atom, while $R_7$ and PG are as defined above by hydration of the nitrile function. This transformation may be performed, for example, in the presence of aqueous hydrogen peroxide solution and a base such as sodium hydroxide.

The 1,2,3,4-tetrahydropyrrolo[1,2-a]pyrazine derivatives of general formula (XVI), for which $X_6$ represents a fluorine or chlorine atom, while $R_7$ and PG are as defined above and $G_8$ represents an alkyl carboxylate group, are transformed into 8-carbamoyl-1,2,3,4-tetrahydropyrrolo[1,2-a]pyrazine derivatives of general formula (X) as defined above, in two steps. Thus, the 3,4-dihydropyrrolo[1,2-a]pyrazine-2,8(1H)-dicarboxamide derivatives of general formula (XVI) as defined above are saponified using a base to the corresponding carboxylic acid of general formula (XVIb) for which $X_6$ represents a fluorine or chlorine atom, while $R_7$ and PG are as defined above. This reaction is performed, for example, by treatment with potassium, sodium or lithium hydroxide, preferentially lithium hydroxide, in a mixture of solvents such as water, methanol and tetrahydrofuran.

The transformation of the carboxylic acid derivatives of general formula (XVIb) into 8-carbamoyl-1,2,3,4-tetrahydropyrrolo[1,2-a]pyrazine derivatives of general formula (X), for which $X_6$ represents a fluorine or chlorine atom, while $R_7$ and PG are as defined above, may be performed by amidation of the carboxylic acid function. This amidation may be performed, for example, by activating the acid with a coupling agent such as carbonyldiimidazole in tetrahydrofuran, and then treatment of the formed activating acid using aqueous ammonia in a solvent such as dimethylformamide.

The compound of general formula (II) is then obtained from derivatives of general formula (X) according to the protocol described above.

Alternatively, and still according to Scheme 6, the 1,2,3,4-tetrahydropyrrolo[1,2-a]pyrazine-8-carboxamide derivatives of general formula (II) as defined above and for which $X_6$ represents a bromine atom or a cyano group, may be prepared in 5 steps starting with a pyrrole derivative of general formula (XVI) for which $R_7$ is as defined above, $X_6$ represents a hydrogen atom, $G_8$ represents an alkyl carboxylate group, preferentially a methyl or ethyl carboxylate and PG constitutes an acid-labile protecting group such as tert-butyloxycarbonyl.

These pyrrole derivatives of general formula (XVI) for which $X_6$ represents a hydrogen atom are thus regioselectively brominated or cyanated in position 6, respectively, by treatment with N-bromosuccinimide in a solvent such as tetrahydrofuran or using chlorosulfonyl isocyanate in a mixture of solvents such as dichloromethane and dimethylformamide to give the corresponding derivative of general formula (XVI) for which $R_7$, $G_8$ and PG are as defined above and $X_6$ represents a bromine atom or a cyano group.

The compounds of general formula (II) for which $X_6$ represents a bromine atom or a cyano group, are then obtained according to the protocol described above starting with the derivative of general formula (XVI), after step of saponification to the corresponding carboxylic acid, activation of the carboxylic acid using a coupling agent such as carbonyldiimidazole and then treatment of the activated form with aqueous ammonia and removal of the protecting group PG using an acid.

The pyrrole derivatives of general formula (XVI) for which $R_7$ is as defined above, $X_6$ represents a hydrogen atom, $G_8$ represents an alkyl carboxylate group and PG constitutes an acid-labile protecting group such as tert-butyloxycarbonyl may be prepared from the corresponding pyrrole derivative of general formula (XVI) for which $R_7$ is as defined above, $X_6$ represents a chlorine or bromine atom, $G_8$ represents an alkyl carboxylate group and PG constitutes an acid-labile protecting group such as tert-butyloxycarbonyl. This transformation may be performed, for example, via a hydrogenation reaction in the presence of a catalyst such as palladium-on-charcoal.

Preparation of the Precursors (III)

The 1,2,3,4-tetrahydropyrrolo[1,2-a]pyrazine derivatives of general formula (III), in which $R_2$, $X_6$, and $R_7$ are as defined above and $G_8$ represents a nitrile group or an alkyl carboxylate group, may be prepared in two steps starting with derivatives of general formula (XVI), in which $X_6$ and $R_7$ are as defined above, $G_8$ represents a nitrile or alkyl carboxylate group and PG represents an acid-labile protecting group such as a tert-butyloxycarbonyl.

Thus, the derivatives of general formula (XXI) in which $X_6$ and $R_7$ are as defined above and $G_8$ represents a nitrile or alkyl carboxylate group are then obtained from derivatives of general formula (XVI) by removal of the protecting group PG, for example, by treatment with trimethylsilyl chloride in a solvent such as methanol or by treatment with an acid such as trifluoroacetic acid in a solvent such as dichloromethane. The derivatives of general formula (III) as defined above may then be prepared from derivatives of general formula (XXI) as defined above:
- either by treatment with an isocyanate derivative of general formula (IIa) in which $R_2$ is as defined previously, in an aprotic solvent such as dichloromethane and optionally in the presence of an organic amine such as triethylamine,
- or by treatment with a carbamate derivative of general formula (IIb) in which $R_2$ is as defined previously and R represents a group such as phenyl, pentafluorophenyl or 4-nitrophenyl, in an aprotic solvent such as acetonitrile and in the presence of a mineral base such as sodium carbonate.

SCHEME 7

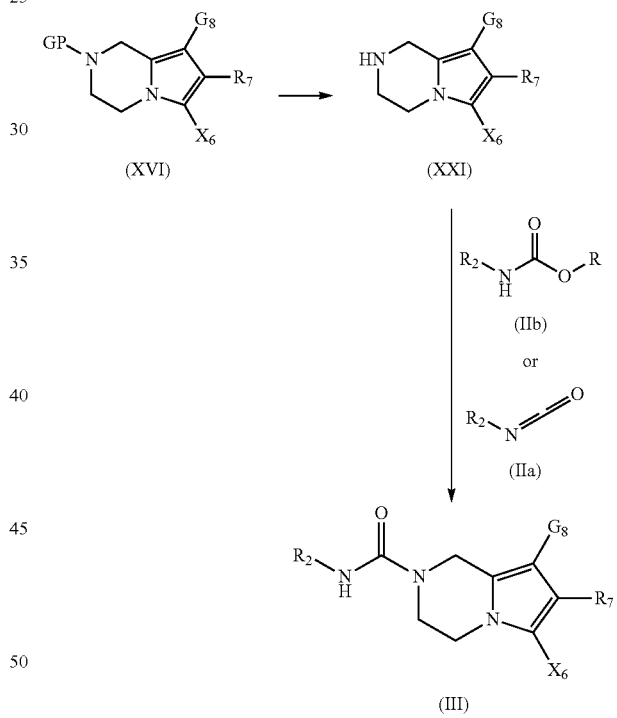

Preparation of the Precursors (IV)

The 1,2,3,4-tetrahydropyrrolo[1,2-a]pyrazine derivatives of general formula (IV), in which $R_2$, $X_6$ and $G_7$ are as defined above, may be prepared in two steps starting with derivatives of general formula (VI), in which $X_6$ and $G_7$ are as defined above, and PG represents an acid-labile protecting group such as a tert-butyloxycarbonyl.

Thus, the derivatives of general formula (XXII), in which $X_6$ and $G_7$ are as defined above, are then obtained from derivatives of general formula (VI) by removal of the protecting group PG, for example by treatment with trimethylsilyl chloride in a solvent such as methanol or by treatment with an acid such as trifluoroacetic acid in a solvent such as dichloromethane. The derivatives of general formula (IV) as defined above may then be prepared from derivatives of general formula (XXII) as defined above:
- either by treatment with an isocyanate derivative of general formula (IIa) in which $R_2$ is as defined previously, in an aprotic solvent such as dichloromethane and optionally in the presence of an organic amine such as triethylamine,
- or by treatment with a carbamate derivative of general formula (IIb) in which $R_2$ is as defined previously and R represents a group such as phenyl, pentafluorophenyl or 4-nitrophenyl, in an aprotic solvent such as acetonitrile and in the presence of a mineral base such as sodium carbonate.

SCHEME 8

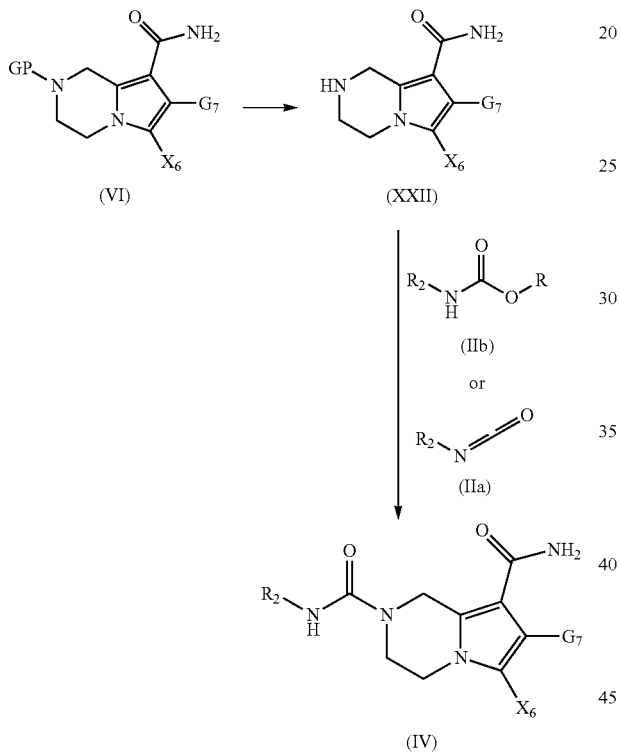

Isocyanate Derivatives of General Formula (IIa)

The isocyanate derivatives of general formula (IIa), in which $R_2$ is as defined, are either commercially available, or prepared according to methods known to those skilled in the art.

Carbamate Derivatives of General Formula (IIb)

The carbamate derivatives of general formula (IIb), in which $R_2$ is as defined previously and R represents a group such as phenyl, pentafluorophenyl or 4-nitrophenyl, are prepared from the corresponding amine $R_2NH_2$ by reaction with the corresponding chloroformate according to methods known to those skilled in the art.

Leaving Groups

In the text hereinabove, the term "leaving group" means a group that can be readily cleaved from a molecule by breaking a heterolytic bond, with loss of an electron pair. This group may, for example, thus be readily replaced with another group during a substitution reaction. Such leaving groups are, for example, halogens or an activated hydroxyl group such as a mesyl, tosyl, triflate, acetyl, etc. Examples of leaving groups and references for preparing them are given in "Advances in Organic Chemistry", J. March, $3^{rd}$ Edition, Wiley Interscience, pp. 310-316.

Protecting Groups

For the compounds of general formula (I) as defined above and in the case where group $R_2$ comprises a hydroxyl function, this function may optionally be protected during the synthesis with a protecting group, for example a tert-butyldiphenylsilyl. This protecting group is removed at the end of the synthesis. Examples of hydroxyl-function protecting groups and references for preparing them and removing them are given in "Greene's Protective Groups in Organic Synthesis" (Fourth Edition), Peter G. M. Wuts, Theodora W. Green, John Wiley & Sons, Inc.

The examples that follow describe the preparation of certain compounds in accordance with the invention. These examples are not limiting, and serve merely to illustrate the invention. The numbers for the compounds given as examples refer to those given in Table 1 below, which illustrate the chemical structures and physical properties, respectively, of a number of compounds according to the invention.

EXAMPLES

Example 1 (Compound 81)

6-Chloro-7-(3-fluorophenyl)-$N^2$-(4,4,4-trifluorobutyl)-3,4-dihydropyrrolo[1,2-a]pyrazine-2,8(1H)-dicarboxamide

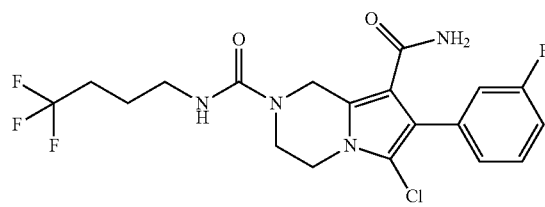

Step 1.1. 4-Nitrophenyl 4,4,4-trifluorobutylcarbamate

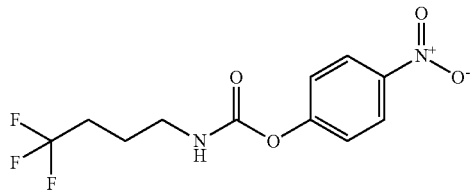 [SMILES: O=C(NCCCC(F)(F)F)Oc1ccc([N+](=O)[O-])cc1]

To a solution of 0.35 g (2.75 mmol) of 4,4,4-trifluorobutylamine (CAS 819-46-5) in 20 ml of dichloromethane, cooled to −15° C., is added dropwise 1.00 g (4.96 mmol) of 4-nitrophenyl chloroformate (CAS 7693-46-1) dissolved in 15 ml of dichloromethane, while maintaining the temperature at −15° C. 0.48 ml (2.75 mmol) of diisopropylethylamine in 10 ml of dichloromethane still at −15° C. is then added. Stirring is continued at −15° C. for 45 minutes, and the temperature of the mixture is then allowed to return to 0° C. over 30 minutes. 20 ml of saturated aqueous sodium hydrogen carbonate solution are then added. The organic phase is separated out by settling and dried over sodium sulfate, and the solvent is partially evaporated off under reduced pressure to a volume of about 8 ml. This solution is chromatographed on a column of 40 g of silica gel, eluting with a mixture of 20% cyclohexane in dichloromethane, to give 0.76 g of 4-nitrophenyl 4,4,4-trifluorobutylcarbamate in the form of a white solid.

m.p.: 118-120° C.

$^1$H NMR (CDCl$_3$) δ: 8.20 (d, 2H); 7.25 (d, 2H); 5.15 (broad s, 1H); 3.3 (m, 2H); 2.15 (m, 2H); 1.8 (m, 2H) ppm.

Step 1.2. (E) and (Z) 3-(3-Fluorophenyl)-2-propenenitrile (CAS 82344-56-7 and 115665-80-0)

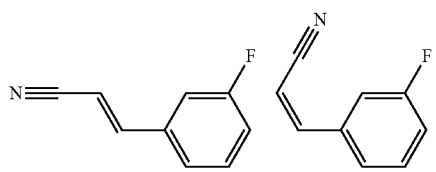

A mixture of 35.0 g (411 mmol) of cyanoacetic acid (CAS 372-09-8) and 56.2 g (453 mmol) of 3-fluorobenzaldehyde (CAS 456-48-4) in a mixture of 400 ml of toluene and 220 ml of pyridine is refluxed for 22 hours using Dean-Stark apparatus to remove the water formed during the reaction. The solvent is then removed under reduced pressure and the residue is co-evaporated 3 times with toluene. The residue is then taken up in ethyl acetate and the organic phase is washed successively with aqueous 1N sodium hydroxide solution, aqueous 1N hydrochloric acid solution and then with saturated sodium chloride solution. The organic phase is then dried over sodium sulfate and the solvent is evaporated off under reduced pressure to give a brown oil, which is chromatographed on a column of silica gel, eluting with toluene, to give 48.5 g a mixture of (E) and (Z) 3-(3-fluorophenyl)-2-propenenitrile in a ratio of (7/3)

$^1$H NMR (CDCl$_3$) δ: 7.55-7.00 (m, 5H); 5.85 and 5.55 (d and d, 1H) ppm.

Step 1.3. 4-(3-Fluorophenyl)-1H-pyrrole-3-carbonitrile (CAS 87388-09-8)

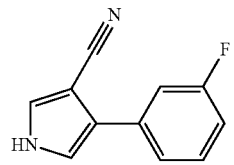 [SMILES: N#Cc1c[nH]cc1-c1cccc(F)c1]

To a suspension of 19.8 g (494 mmol) of sodium hydride at 60% in oil in 350 ml of anhydrous tetrahydrofuran is added dropwise a mixture of 48.5 g (330 mmol) of the mixture of (Z) and (E) 3-(3-fluorophenyl)-2-propenenitrile in a ratio of (7/3) and 64.4 g (330 mmol) of tosylmethyl isocyanide (CAS 36635-61-7) dissolved in 250 ml of tetrahydrofuran, while maintaining the temperature of the reaction medium at about 25° C. The mixture is then stirred for 1 hour at room temperature and is then poured into ice-water. The reaction product is then extracted with ethyl acetate, the organic phase is dried over sodium sulfate and the solvent is evaporated off under reduced pressure to give a brown solid, which is dissolved in 350 ml of hot chloroform and purified by chromatography on a column of 600 g of silica gel, eluting with dichloromethane and then with a mixture of 1% methanol in dichloromethane, to give 41.5 g of 4-(3-fluorophenyl)-1H-pyrrole-3-carbonitrile in the form of a beige-coloured solid after triturating in dichloromethane, filtering off and drying.

m.p.: 140-142° C.

$^1$H NMR (DMSO-d$_6$) δ: 12.0 (broad s, 1H); 7.75 (s, 1H); 7.55-7.00 (m, 4H); 7.10 (m, 1H) ppm.

Step 1.4. 5-Chloro-4-(3-fluorophenyl)-1H-pyrrole-3-carbonitrile

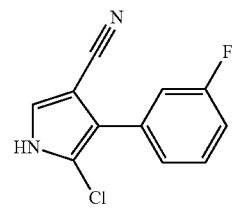 [SMILES: N#Cc1c[nH]c(Cl)c1-c1cccc(F)c1]

To a solution of 41.0 g (220 mmol) of 4-(3-fluorophenyl)-1H-pyrrole-3-carbonitrile in 400 ml of tetrahydrofuran are added portionwise 33.0 g (242 mmol) of N-chlorosuccinimide (CAS 128-09-6) and the mixture is then stirred for 24 hours at reflux. After cooling, 200 ml of water containing 5 g of sodium thiosulfate are added and, after stirring for 5 minutes, the reaction product is extracted with ethyl acetate. The organic phase is dried over sodium sulfate and the solvent is evaporated off under reduced pressure to give 45.5 g of 5-chloro-4-(3-fluorophenyl)-1H-pyrrole-3-carbonitrile in the form of a whitish powder after triturating in 200 ml of dichloromethane, filtering off and drying.

m.p.: 158-161° C.

$^1$H NMR (DMSO-d$_6$) δ: 12.9 (broad s, 1H); 7.85 (s, 1H); 7.55 (m, 1H); 7.35 (m, 2H); 7.25 (m, 1H) ppm.

Step 1.5. tert-Butyl {2-[2-chloro-4-cyano-3-(3-fluorophenyl)-1H-pyrrol-1-yl]ethyl}carbamate

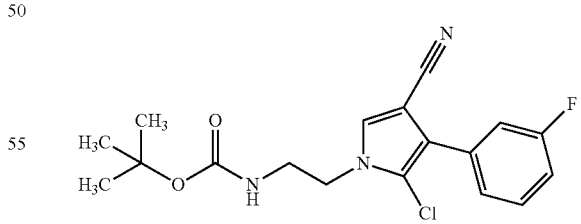

To a solution of 39.5 g (179 mmol) of 5-chloro-4-(3-fluorophenyl)-1H-pyrrole-3-carbonitrile in 450 ml of acetonitrile are added 14.3 g (358 mmol) of powdered sodium hydroxide and 2.43 g (7.1 mmol) of tetrabutylammonium hydrogen sulfate, and the mixture is stirred vigorously for 30 minutes, 48.1 g (214 mmol) of tert-butyl(2-bromoethyl)-carbamate (CAS 39684-80-5) are then added and the mixture is then stirred for 17 hours at reflux. After cooling, the solvent is evaporated off under reduced pressure, and the residue is taken up in ethyl acetate. The organic phase is then washed with saturated sodium chloride solution and dried over sodium sulfate, and the solvent is evaporated off under reduced pressure to give 47.3 g of tert-butyl{2-[2-chloro-4-cyano-3-(3-fluorophenyl)-1H-pyrrol-1-yl]ethyl}-carbamate in the form of a beige-coloured powder after triturating in 150 ml of diisopropyl ether, filtering off and drying.

m.p.: 97-99° C.

¹H NMR (DMSO-d₆) δ: 7.85 (s, 1H); 7.60 (m, 1H); 7.35 (m, 1H); 7.30 (m, 2H); 7.0 (broad t, 1H); 4.10 (m, 2H); 3.30 (m, 2H); 1.40 (s, 9H) ppm.

Step 1.6. 6-Chloro-7-(3-fluorophenyl)-1,2,3,4-tetrahydropyrrolo[1,2-a]pyrazine-8-carbonitrile

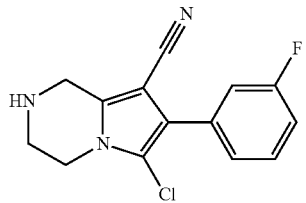 [SMILES: N#Cc1c(-c2cccc(F)c2)c(Cl)n2c1CNCC2]

To a solution of 47.3 g (130 mmol) of tert-butyl{2-[2-chloro-4-cyano-3-(3-fluorophenyl)-1H-pyrrol-1-yl]ethyl}-carbamate in 85 ml of ethanol are added slowly 488 ml (1465 mmol) of aqueous 3N hydrochloric acid solution. Setting to a solid is rapidly observed, and the medium then becomes clear. After 45 minutes, 5.56 g (48.1 mmol) of paraformaldehyde are added and heating is continued at 70° C. for 2 hours 30 minutes. After cooling, the reaction medium is poured slowly into ice-cold aqueous 4N sodium hydroxide solution. The product is extracted with dichloromethane, the organic phase is dried over sodium sulfate and the solvent is evaporated off under reduced pressure to give a brown oil, which is chromatographed on a column of 300 g of silica gel, eluting with a mixture of 1 to 2% methanol in dichloromethane, to give 21.0 g of 6-chloro-7-(3-fluorophenyl)-1,2,3,4-tetrahydropyrrolo[1,2-a]pyrazine-8-carbonitrile in the form of a beige-coloured powder after triturating in 150 ml of diisopropyl ether, at reflux, chilling, filtering off and drying.

m.p.: 104-106° C.

¹H NMR (DMSO-d₆) δ: 7.55 (m, 1H); 7.35 (m, 1H); 7.30 (m, 1H);

7.25 (m, 1H); 4.00 (s, 2H); 3.80 (t, 2H); 3.15 (t, 2H); 1.70 (broad s, 1H) ppm.

Step 1.7. tert-Butyl-6-chloro-8-cyano-7-(3-fluorophenyl)-3,4-dihydropyrrolo[1,2-a]pyrazine-2(1H)-carboxamide

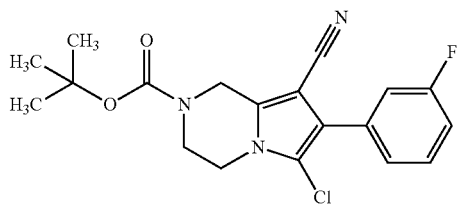 [SMILES: CC(C)(C)OC(=O)N1CCn2c(Cl)c(-c3cccc(F)c3)c(C#N)c2C1]

To a solution of 21.0 g (76.0 mmol) of 6-chloro-7-(3-fluorophenyl)-1,2,3,4-tetrahydropyrrolo[1,2-a]pyrazine-8-carbonitrile in 200 ml of dichloromethane are added slowly 18.2 g (83.6 mmol) of di-tert-butyl dicarbonate (CAS 24424-99-5) dissolved in about 100 ml of dichloromethane. After stirring for 45 minutes at room temperature, the solvent is evaporated off under reduced pressure to give a brown oil, which is crystallized from 100 ml of diisopropyl ether to give 26.3 g of tert-butyl-6-chloro-8-cyano-7-(3-fluorophenyl)-3,4-dihydropyrrolo[1,2-a]pyrazine-2(1H)-carboxamide in the form of a beige-coloured powder after filtering off and drying.

m.p.: 144-116° C.

¹H NMR (DMSO-d₆) δ: 7.58 (m, 1H); 7.38 (m, 1H); 7.32 (m, 1H); 7.26 (m, 1H); 4.70 (s, 2H); 4.05 (t, 2H); 3.85 (t, 2H); 1.50 (s, 9H) ppm.

Step 1.8. tert-butyl 8-carbamoyl-6-chloro-7-(3-fluoro-phenyl)-3,4-dihydropyrrolo[1,2-a]pyrazine-2(1H)-carboxylate

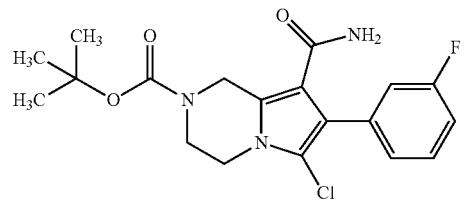 [SMILES: CC(C)(C)OC(=O)N1CCn2c(Cl)c(-c3cccc(F)c3)c(C(N)=O)c2C1]

To a solution of 26.6 g (70.8 mmol) of tert-butyl-6-chloro-8-cyano-7-(3-fluorophenyl)-3,4-dihydropyrrolo[1,2-a]pyrazine-2(1H)-carboxamide in 270 ml of methanol and dimethyl sulfoxide (3:2) are added 6.15 ml (74.3 mmol) of aqueous 35% sodium hydroxide solution and then 12.4 ml (142 mmol) of 35-volumes aqueous hydrogen peroxide solution in 4 fractions every 30 minutes. After reaction for 18 hours at 60° C., the mixture is cooled, partially concentrated under reduced pressure and taken up in ethyl acetate. The solution is washed with aqueous 5% sodium thiosulfate solution and then with saturated aqueous sodium chloride solution. The organic phase is dried over sodium sulfate and the solvent is evaporated off under reduced pressure to give an orange-coloured solid, which is crystallized from about 200 ml of acetonitrile to give 19.8 g of tert-butyl 8-carbamoyl-6-chloro-7-(3-fluorophenyl)-3,4-dihydropyrrolo[1,2-a]pyrazine-2(1H)-carboxylate in the form of a whitish powder after filtering off and drying.

After evaporating off the solvent under reduced pressure and purifying by chromatography of the crystallization mother liquors on a column of 80 g of silica gel, elution with a mixture of 4% methanol in dichloromethane gives 2.35 g of additional product after crystallizing from acetonitrile, filtering off and drying.

m.p.: 189-192° C.

¹H NMR (DMSO-d₆) δ: 7.55 (m, 1H); 7.2 (m, 3H); 7.1 (broad s, 1H); 6.2 (broad s, 1H); 4.80 (s, 2H); 4.00 (t, 2H); 3.85 (t, 2H); 1.50 (s, 9H) ppm.

Step 1.9. 6-Chloro-7-(3-fluorophenyl)-1,2,3,4-tetrahydropyrrolo[1,2-a]pyrazine-8-carboxamide

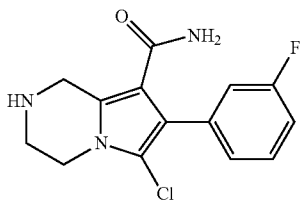

To a solution of 22.0 g (70.8 mmol) of tert-butyl 8-carbamoyl-6-chloro-7-(3-fluorophenyl)-3,4-dihydropyrrolo-[1,2-a]pyrazine-2(1H)-carboxylate in 130 ml of dichloromethane are added slowly 128 ml (1680 mmol) of trifluoroacetic acid.

After stirring for 1 hour at room temperature, the solvent is evaporated off under reduced pressure, the residue is taken up in aqueous 3N hydrochloric acid solution and the aqueous phase is washed with ethyl acetate. The aqueous phase is basified by addition of aqueous ammonia and the product is extracted with chloroform. The organic phase is dried over sodium sulfate and concentrated under reduced pressure. The residue is triturated while hot from 80 ml of hot acetonitrile. After cooling, 15.4 g of 6-chloro-7-(3-fluorophenyl)-1,2,3,4-tetrahydropyrrolo[1,2-a]pyrazine-8-carboxamide are isolated in the form of a whitish powder after separating out by filtration and drying under reduced pressure.

m.p.: 226-228° C.

$^1$H NMR (DMSO-$d_6$) δ: 7.55 (m, 1H); 7.15 (m, 3H); 6.9 (broad s, 1H); 6.2 (broad s, 1H); 4.00 (s, 2H); 3.85 (t, 2H); 3.10 (t, 2H) ppm.

Step 1.10. 6-Chloro-7-(3-fluorophenyl)-$N^2$-(4,4,4-trifluoro-butyl)-3,4-dihydropyrrolo[1,2-a]pyrazine-2,8(1H)-dicarboxamide

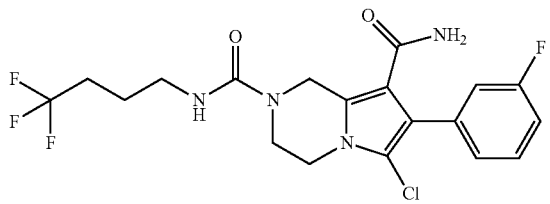 [SMILES: NC(=O)c1c(-c2cccc(F)c2)c(Cl)n2c1CN(C(=O)NCCCC(F)(F)F)CC2]

A suspension of 0.165 (0.56 mmol) of 6-chloro-7-(3-fluorophenyl)-1,2,3,4-tetrahydropyrrolo[1,2-a]pyrazine-8-carboxamide, 0.197 g (0.67 mmol) of 4-nitrophenyl 4,4,4-trifluorobutylcarbamate and 0.155 g (1.12 mmol) of sodium carbonate in 3 ml of acetonitrile is heated at 65° C. for 1 hour 30 minutes. After cooling, the mixture is poured into aqueous 1N sodium hydroxide solution and the product is extracted with dichloromethane. After drying over sodium sulfate and filtering, the solvent is evaporated off under reduced pressure and the residue is purified by chromatography on a column of 24 g of silica gel, eluting with a mixture of 3% methanol in dichloromethane, to give 0.192 g of 6-chloro-7-(3-fluorophenyl)-$N^2$-((4,4,4-trifluoro-butyl)-3,4-dihydropyrrolo[1,2-a]pyrazine-2,8(1H)-dicarboxamide in the form of a white powder after crystallization from 8 ml of acetonitrile, filtering off and drying under reduced pressure.

m.p.: 100-117° C.

$^1$H NMR (DMSO-$d_6$) δ: 7.50 (m, 1H); 7.2 (m, 3H); 7.05 (broad s, 1H); 6.90 (t, 1H); 6.20 (broad s, 1H); 4.75 (s, 2H); 3.90 (m, 2H); 3.80 (m, 2H); 3.15 (m, 2H); 2.3 (m, 2H); 1.70 (m, 2H) ppm.

Example 2 (Compound 79)

6-Chloro-7-(3-fluorophenyl)-$N^2$-(1,1,1-trifluoro-2-methylpropan-2-yl)-3,4-dihydropyrrolo[1,2-a]pyrazine-2,8(1H)-dicarboxamide

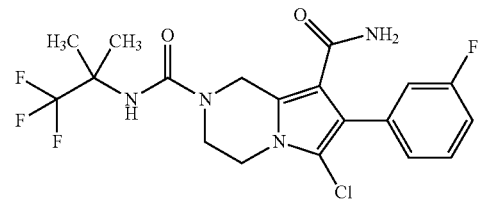

Step 2.1. 4-Nitrophenyl 1,1,1-trifluoro-2-methylpropan-2-ylcarbamate

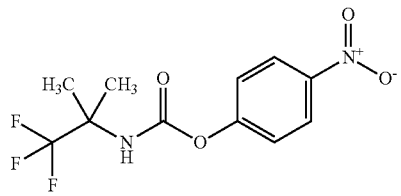 [SMILES: CC(C)(NC(=O)Oc1ccc([N+](=O)[O-])cc1)C(F)(F)F]

To a solution of 0.35 g (2.75 mmol) of 1,1,1-trifluoro-2-methylpropan-2-ylamine (CAS 812-18-0) in 20 ml of dichloromethane, cooled to −15° C., is added dropwise 1.00 g (4.96 mmol) of 4-nitrophenyl chloroformate (CAS 7693-46-1) dissolved in 15 ml of dichloromethane, while maintaining the temperature at −15° C. 0.48 ml (2.75 mmol) of diisopropylethylamine in 10 ml of dichloromethane is then added, still at −15° C. Stirring is continued at −15° C. for 2 hours, and the temperature of the mixture is then allowed to return to 0° C. over 1 hour. 20 ml of saturated aqueous sodium hydrogen carbonate solution are then added. The organic phase is separated out by settling and dried over sodium sulfate, and the solvent is partially evaporated off under reduced pressure to a volume of about 8 ml. This solution is chromatographed on a column of 40 g of silica gel, eluting with a mixture of 20% cyclohexane in dichloromethane, to give 0.21 g of 4-nitrophenyl 1,1,1-trifluoro-2-methylpropan-2-ylcarbamate in the form of a white solid.

m.p.: 77-80° C.

$^1$H NMR (CDCl$_3$) δ: 8.30 (d, 2H); 7.35 (d, 2H); 5.25 (broad s, 1H); 1.65 (s, 6H) ppm.

Step 2.2 6-Chloro-7-(3-fluorophenyl)-N²-(1,1,1-trifluoro-2-methylpropan-2-yl)-3,4-dihydropyrrolo[1,2-a]pyrazine-2,8(1H)-dicarboxamide

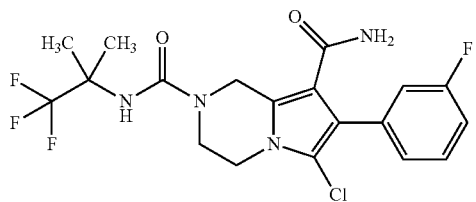 [SMILES: CC(C)(NC(=O)N1CCn2c(Cl)c(-c3cccc(F)c3)c(C(N)=O)c2C1)C(F)(F)F]

A suspension of 0.165 (0.56 mmol) of 6-chloro-7-(3-fluorophenyl)-1,2,3,4-tetrahydropyrrolo[1,2-a]pyrazine-8-carboxamide, 0.197 g (0.67 mmol) of 4-nitrophenyl 1,1,1-trifluoro-2-methylpropan-2-ylcarbamate and 0.155 (1.12 mmol) of sodium carbonate in 3 ml of acetonitrile is heated at 65° C. for 1 hour 30 minutes. After cooling, the mixture is poured into aqueous 1N sodium hydroxide solution and the product is extracted with dichloromethane. After drying over sodium sulfate and filtering, the solvent is evaporated off under reduced pressure and the residue is purified by chromatography on a column of 24 g of silica gel, eluting with a mixture of 3% methanol in dichloromethane, to give 0.125 g of 6-chloro-7-(3-fluorophenyl)-N²-(1,1,1-trifluoro-2-methylpropan-2-yl)-3,4-dihydropyrrolo[1,2-a]pyrazine-2,8(1H)-dicarboxamide in the form of a white powder after crystallization from 4 ml of acetonitrile, filtering off and drying under reduced pressure.

m.p.: 183-187° C.

¹H NMR (DMSO-d₆) δ: 7.50 (m, 1H); 7.2 (m, 3H); 7.05 (broad s, 1H); 6.65 (s, 1H); 6.25 (broad s, 1H); 4.70 (s, 2H); 3.95 (m, 2H); 3.80 (m, 2H); 1.50 (s, 6H) ppm.

Example 3 (Compound 73)

6-Chloro-7-(3-fluorophenyl)-N²-(3-hydroxy-2,2-dimethylpropyl)-3,4-dihydropyrrolo[1,2-a]pyrazine-2,8(1H)-dicarboxamide

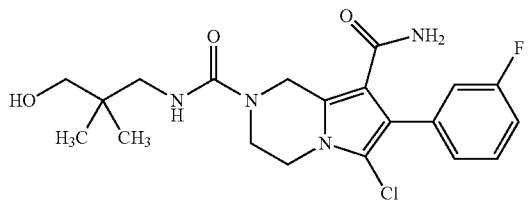 [SMILES: CC(C)(CO)CNC(=O)N1CCn2c(Cl)c(-c3cccc(F)c3)c(C(N)=O)c2C1]

Step 3.1. 3-(tert-Butyldiphenylsilanoxy)-2,2-dimethyl-propylamine

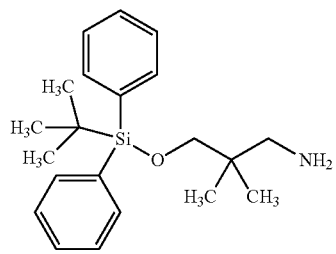 [SMILES: CC(C)(CN)CO[Si](c1ccccc1)(c1ccccc1)C(C)(C)C]

To a solution at 0° C. of 0.500 g (4.85 mmol) of 3-amino-2,2-dimethylpropanol (CAS 26734-09-8) in 12 ml of dichloromethane are added 0.059 g (0.48 mmol) of dimethylaminopyridine and 1.35 ml (9.7 mmol) of triethylamine. 1.60 g (5.82 mmol) of tert-butyldiphenylsilyl chloride dissolved in 5 ml of dichloromethane are then added dropwise. The mixture is stirred for 30 minutes at 0° C. and then for 2 hours at room temperature. 20 ml of water are then added. The organic phase is separated out by settling, washed with water and then with saturated aqueous sodium chloride solution and dried over sodium sulfate, and the solvent is evaporated off under reduced pressure to give an oil, which is chromatographed on a column of aminopropyl silica gel, eluting with a mixture of 0 to 10% methanol in dichloromethane, to give 1.20 g of 3-(tert-butyldiphenyl-silanoxy)-2,2-dimethylpropylamine in the form of a colourless oil.

¹H NMR (CDCl₃) δ: 7.70 (m, 4H); 7.45 (m, 6H); 3.40 (s, 2H); 2.65 (s, 2H); 1.5 (broad s, 2H); 1.10 (s, 9H); 0.90 (s, 4H) ppm.

Step 3.2. 4-Nitrophenyl 3-(tert-butyldiphenylsilanoxy)-2,2-dimethylpropylcarbamate

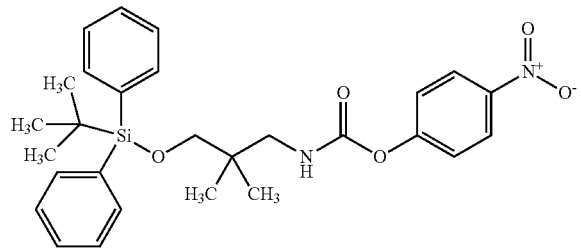 [SMILES: CC(C)(CNC(=O)Oc1ccc([N+](=O)[O-])cc1)CO[Si](c1ccccc1)(c1ccccc1)C(C)(C)C]

To a solution, at 0° C., of 0.120 g (3.51 mmol) of 3-(tert-butyldiphenylsilanoxy)-2,2-dimethylpropylamine in 25 ml of dichloromethane are added dropwise 1.42 g (7.03 mmol) of 4-nitrophenyl chloroformate (CAS 7693-46-1) dissolved in 5 ml of dichloromethane. 0.63 ml (3.5 mmol) of diisopropylethylamine is then added. Stirring is continued at 0° C. for 45 minutes, and the temperature of the mixture is then allowed to return to 0° C. over 1 hour. 20 ml of saturated aqueous sodium hydrogen carbonate solution are then added. The organic phase is separated out on a hydrophobic filter cartridge and the solvent is partially evaporated off under reduced pressure to a volume of about 8 ml. This solution is chromatographed on a column of silica gel, eluting with a mixture of 5 to 40% ethyl acetate in cyclohexane, to give 0.21 g of 4-nitrophenyl 3-(tert-butyldiphenylsilanoxy)-2,2-dimethylpropylcarbamate in the form of an oil.

¹H NMR (CDCl₃) δ: 8.28 (d, 2H); 7.73 (m, 4H); 7.5 (m, 6H); 7.34 (d, 2H); 5.9 (broad s, 1H); 3.50 (s, 2H); 2.29 (d, 2H); 1.16 (s, 9H); 1.00 (s, 4H) ppm.

Step 3.3 N²-(3-(tert-Butyldiphenylsilanoxy)-2,2-dimethyl-propyl)-6-chloro-7-(3-fluorophenyl)-3,4-dihydropyrrolo[1,2-a]pyrazine-2,8(1H)-dicarboxamide

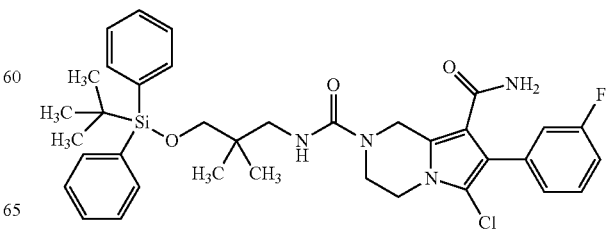

A suspension of 0.250 (0.85 mmol) of 6-chloro-7-(3-fluorophenyl)-1,2,3,4-tetrahydropyrrolo[1,2-a]pyrazine-8-carboxamide, 0.518 g (1.02 mmol) of 4-nitrophenyl 3-(tert-butyldiphenylsilanoxy)-2,2-dimethylpropylcarbamate and 0.235 g (1.70 mmol) of sodium carbonate in 3 ml of acetonitrile is heated at 65° C. for 1 hour 30 minutes. After cooling, the mixture is poured into aqueous 1N sodium hydroxide solution and the product is extracted with dichloromethane. After drying over sodium sulfate and filtering, the solvent is evaporated off under reduced pressure and the residue is purified by chromatography on a column of silica gel, eluting with a mixture of 35 to 65% ethyl acetate in cyclohexane, to give 0.44 g of $N^2$-(3-(tert-butyldiphenylsilanoxy)-2,2-dimethylpropyl)-6-chloro-7-(3-fluorophenyl)-3,4-dihydropyrrolo[1,2-a]pyrazine-2,8(1H)-dicarboxamide in the form of a pale yellow foam.

$^1$H NMR (DMSO-$d_6$) δ: 7.59 (m, 4H); 7.3 (m, 7H); 7.1 (m, 3H); 5.20 (broad s, 2H); 4.8 (broad t, 1H); 6.25 (broad s, 1H); 3.80 (m, 4H); 4.70 (s, 2H); 3.34 (s, 2H); 3.21 (d, 2H); 1.01 (s, 9H); 0.85 (s, 6H) ppm.

Step 3.4. 6-Chloro-7-(3-fluorophenyl)-$N^2$-(3-hydroxy-2,2-dimethylpropyl)-3,4-dihydropyrrolo[1,2-a]pyrazine-2,8(1H)-dicarboxamide

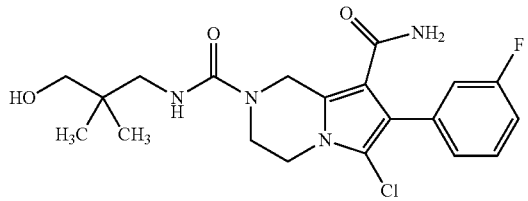 [SMILES: CC(C)(CO)CNC(=O)N1CCn2c(Cl)c(-c3cccc(F)c3)c(C(N)=O)c2C1]

To a solution at 0° C. of 0.44 g (0.65 mmol) of $N^2$-(3-(tert-butyldiphenylsilanoxy)-2,2-dimethylpropyl)-6-chloro-7-(3-fluorophenyl)-3,4-dihydropyrrolo[1,2-a]pyrazine-2,8(1H)-dicarboxamide in 1.3 ml of tetrahydrofuran is added 0.73 ml (0.73 mmol) of a 1M solution of tetrabutylammonium fluoride in tetrahydrofuran. The mixture is stirred for 30 minutes at 0° C. and then for 4 hours at room temperature, and is then diluted with 20 ml of dichloromethane. The solution is washed with aqueous ammonia solution and the organic phase is separated out on a hydrophobic cartridge and then concentrated under reduced pressure. The residue is purified by chromatography on a column of silica gel, eluting with a mixture of 2 to 5% methanol in dichloromethane, to give 0.095 g of 6-chloro-7-(3-fluorophenyl)-N2-(-[(3-hydroxy-2,2-dimethylpropyl)-3,4-dihydropyrrolo[1,2-a]pyrazine-2,8(1H)-dicarboxamide in the form of a white solid after recrystallizing from acetonitrile and drying.

m.p.: 205-207° C.

$^1$H NMR (DMSO-$d_6$) δ: 7.48 (m, 1H); 7.2 (m, 4H); 6.86 (broad t, 1H); 6.9 (broad s, 1H); 4.75 (s, 2H); 4.65 (t, 1H); 3.92 (m, 2H); 3.84 (m, 2H); 3.06 (d, 2H); 2.97 (d, 2H); 0.79 (s, 6H) ppm.

Example 4 (Compound 60)

$N^2$-(tert-Butyl)-6-chloro-7-phenyl-3,4-dihydropyrrolo[1,2-a]pyrazine-2,8(1H)-dicarboxamide

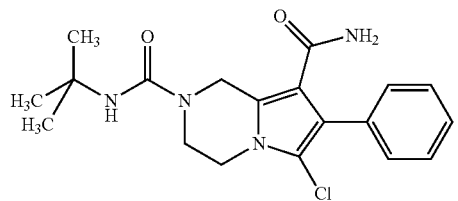 [SMILES: CC(C)(C)NC(=O)N1CCn2c(Cl)c(-c3ccccc3)c(C(N)=O)c2C1]

Step 4.1. 4-Phenyl-1H-pyrrole-3-carbonitrile (CAS 40167-37-1) (*Organic Reactions*. Vol. 57, Edited by Larry E. Overman et al. 2001 Organic Reactions, Inc. published by John Wiley & Sons)

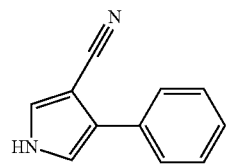 [SMILES: N#Cc1c[nH]cc1-c1ccccc1]

To a suspension of 53.7 g (464 mmol) of potassium tert-butoxide in 500 ml of anhydrous tetrahydrofuran is added dropwise a mixture of 48.5 g (330 mmol) of the mixture of 50.0 g (387 mmol) of cinnamonitrile (CAS 1885-38-7) and 75.6 g (387 mmol) of tosylmethyl isocyanide (CAS 36635-61-7) dissolved in 500 ml of tetrahydrofuran, while maintaining the temperature of the reaction medium at about 25° C. The mixture is then stirred for 1 hour 30 minutes at room temperature and is then poured into saturated sodium chloride solution. The reaction product is then extracted with ethyl acetate, the organic phase is dried over sodium sulfate and the solvent is evaporated off under reduced pressure to give a brown solid, which is dissolved in 350 ml of hot chloroform and purified by chromatography on silica gel, eluting with dichloromethane, to give 44.3 g of 4-phenyl-1H-pyrrole-3-carbonitrile in the form of a beige-coloured powder after triturating in diisopropyl ether, filtering off and drying.

$^1$H NMR (CDCl$_3$) δ: 7.7-7.6 (m, 2H); 7.5-7.3 (m, 3H); 7.00 (t, 1H) ppm.

Step 4.2.
5-Chloro-4-phenyl-1H-pyrrole-3-carbonitrile

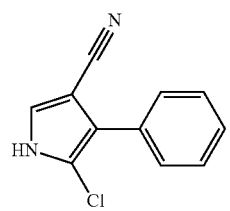

To a solution of 44.3 g (263 mmol) of 4-phenyl-1H-pyrrole-3-carbonitrile (CAS 40167-37-1) in 600 ml of tetrahydrofuran are added portionwise 35.8 g (268 mmol) of N-chlorosuccinimide (CAS 128-09-6) and the mixture is then stirred for 48 hours at reflux. After cooling, the reaction medium is concentrated under reduced pressure and the residue is then taken up in water. The reaction product is extracted with ethyl acetate, the organic phase is dried over sodium sulfate and the solvent is evaporated off under reduced pressure to give a brown solid, which is triturated in diisopropyl ether and then isolated by filtration. The filtrate is concentrated under reduced pressure and the solid residue obtained is triturated in diisopropyl ether and then isolated by filtration. The two batches of solid are combined to give 51.7 g of 5-chloro-4-phenyl-1H-pyrrole-3-carbonitrile in the form of a beige-coloured powder after drying.

m.p.: 140-142° C.

$^1$H NMR (CDCl$_3$) δ: 7.65-7.55 (m, 2H); 7.5-7.3 (m, 3H); 7.30 (d, 1H) ppm.

Step 4.3. tert-Butyl {2-[2-chloro-4-cyano-3-phenyl-1H-pyrrol-1-yl]ethyl}carbamate

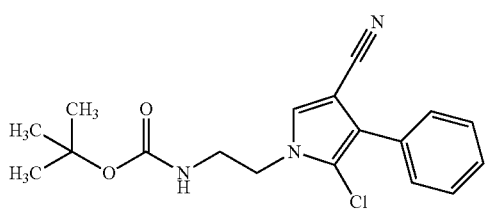

To a solution of 51.6 g (254 mmol) of 5-chloro-4-phenyl-1H-pyrrole-3-carbonitrile in 400 ml of acetonitrile are added 20.4 g (509 mmol) of finely ground sodium hydroxide and 3.46 g (10.2 mmol) of tetrabutylammonium hydrogen sulfate, and the mixture is stirred vigorously for a few minutes, followed by adding 68.5 g (255 mmol) of tert-butyl(2-bromoethyl)carbamate (CAS 39684-80-5), and the mixture is then stirred for 4 hours at reflux. [After cooling, the solvent is evaporated off under reduced pressure, the residue is taken up in water and the product is extracted with ethyl acetate.] The organic phase is then dried over sodium sulfate and the solvent is evaporated off under reduced pressure to give 67.9 g of tert-butyl{2-[2-chloro-4-cyano-3-phenyl-1H-pyrrol-1-yl]ethyl}carbamate in the form of a white powder after recrystallizing from acetonitrile, filtering off and drying.

m.p.: 114-116° C.

$^1$H NMR (CDCl$_3$) δ: 7.6-7.55 (m, 2H); 7.5-7.3 (m, 1H); 7.20 (s, 1H); 4.65 (broad s, 1H); 4.15 (broad t, 2H); 3.45 (m, 2H); 1.46 (s, 9H) ppm.

Step 4.4. 6-Chloro-7-phenyl-1,2,3,4-tetrahydropyrrolo-[1,2-a]pyrazine-8-carbonitrile

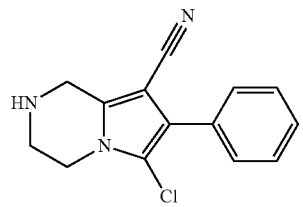

To a suspension of 66.9 g (193 mmol) of tert-butyl{2-[2-chloro-4-cyano-3-phenyl-1H-pyrrol-1-yl]ethyl}carbamate in 150 ml of ethanol are added slowly 688 ml (2670 mmol) of aqueous 4N hydrochloric acid solution and the mixture is heated to 90° C. Evolution of gas is rapidly observed, and after 1 hour, the medium is clear. 6.44 g (71.5 mmol) of paraformaldehyde are then added and heating is continued for a further 4 hours. After cooling, the reaction medium is basified slowly by adding aqueous ammonia, the product is extracted with dichloromethane, the organic phase is dried over sodium sulfate and the solvent is evaporated off under reduced pressure to give a yellow solid, which is triturated in acetonitrile and then isolated by filtration. The filtrate is concentrated under reduced pressure and the solid residue obtained is triturated in acetonitrile and then isolated by filtration. The two batches of solid are combined to give 30.6 g of 6-chloro-7-phenyl-1,2,3,4-tetrahydropyrrolo[1,2-a]pyrazine-8-carbonitrile in the form of a beige-coloured powder after drying.

m.p.: 128-130° C.

$^1$H NMR (CDCl$_3$) δ: 7.6 (m, 2H); 7.5-7.3 (m, 6H); 4.20 (s, 2H); 3.90 (t, 2H); 3.35 (t, 2H); 1.7 (bs, 1H) ppm.

Step 4.5. N-tert-Butyl-6-chloro-8-cyano-7-phenyl-3,4-dihydropyrrolo[1,2-a]pyrazine-2(1H)-carboxamide

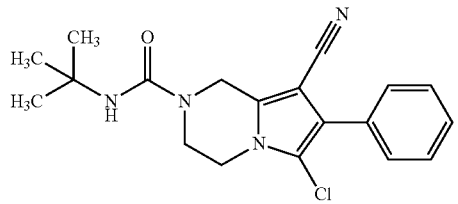 [SMILES: CC(C)(C)NC(=O)N1CCn2c(Cl)c(-c3ccccc3)c(C#N)c2C1]

To a solution of 34 g (119 mmol) of 6-chloro-7-phenyl-1,2,3,4-tetrahydropyrrolo[1,2-a]pyrazine-8-carbonitrile in 300 ml of dichloromethane are added 16.3 ml (143 mmol) of tert-butyl isocyanate (CAS 1609-86-5). After stirring for 4 hours at room temperature, the solvent is evaporated off under reduced pressure to give an orange-coloured solid, which is crystallized from acetonitrile to give 40.0 g of N-tert-butyl-6-chloro-8-cyano-7-phenyl-3,4-dihydropyrrolo[1,2-a]pyrazine-2(1H)-carboxamide in the form of a yellow powder after filtering off and drying.

m.p.: 174-176° C.

$^1$H NMR (CDCl$_3$) δ: 7.6 (m, 2H); 7.5-7.3 (m, 3H); 4.35 (s, 2H); 4.4 (broad s, 1H); 4.0 (m, 2H); 3.9 (m, 2H); 1.4 (s, 9H) ppm.

Step 4.6. N²-(tert-Butyl)-6-chloro-7-phenyl-3,4-dihydropyrrolo[1,2-a]pyrazine-2,8(1H)-dicarboxamide

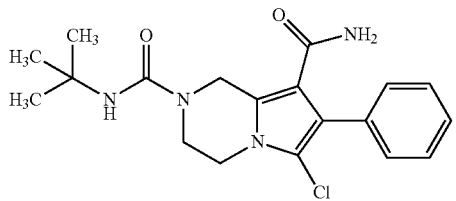

To a solution at 65° C. of 40.0 g (112 mmol) of N-tert-butyl-6-chloro-8-cyano-7-phenyl-3,4-dihydropyrrolo[1,2-a]pyrazine-2(1H)-carboxamide in 400 ml of methanol and dimethyl sulfoxide (3:2) are added 10.1 ml (118 mmol) of aqueous 35% sodium hydroxide solution and then 19.8 ml (21.8 mmol) of 35-volumes aqueous hydrogen peroxide solution in 4 fractions every 15 minutes. After reaction for 30 minutes at 65° C., the mixture is cooled, partially concentrated under reduced pressure and taken up in dichloromethane. The organic phase is washed with water and is then dried over sodium sulfate, and the solvent is evaporated off under reduced pressure to give a yellow solid, which is crystallized from acetonitrile and then recrystallized from acetonitrile, to give 25.2 g of N²-(tert-butyl)-6-chloro-7-phenyl-3,4-dihydropyrrolo[1,2-a]pyrazine-2,8(1H)-dicarboxamide in the form of a white powder after filtering off and drying.

m.p.: 197-199° C.

$^1$H NMR (DMSO-d$_6$) δ: 7.45 (m, 2H); 7.35 (m, 3H); 7.0 (broad s, 1H); 6.15 (s, 1H); 5.85 (broad s, 1H); 4.70 (s, 2H); 3.90 (m, 2H); 3.80 (m, 2H); 1.30 (s, 9H) ppm.

Example 5 (Compound 95)

6-Chloro-7-(3-cyanophenyl)-N²-(tetrahydro-2H-pyran-4-yl)-3,4-dihydropyrrolo[1,2-a]pyrazine-2,8(1H)-dicarboxamide

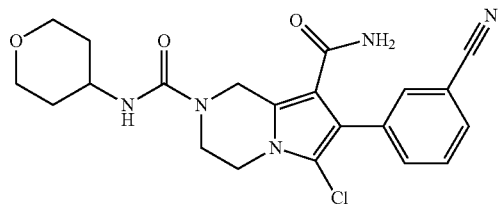 [SMILES: N#Cc1cccc(-c2c(C(N)=O)c3n(c2Cl)CCN(C(=O)NC2CCOCC2)C3)c1]

Step 5.1. 4-Nitrophenyl tetrahydro-2H-pyran-4-ylcarbamate

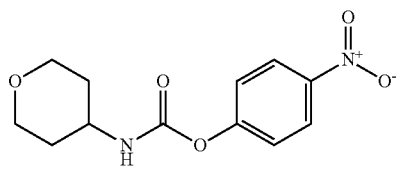 [SMILES: O=C(NC1CCOCC1)Oc1ccc([N+](=O)[O-])cc1]

To a solution of 5.00 g (36.3 mmol) of tetrahydro-2H-pyran-4-yl-amine hydrochloride (CAS 38041-19-9) in 300 ml of dichloromethane, cooled to −15° C. are added portionwise 13.2 g (65.4 mmol) of 4-nitrophenyl chloroformate (CAS 7693-46-1) and then 12.7 ml (72.7 mmol) of diisopropylethylamine. Stirring is continued at −0° C. for 2 hours, and 20 ml of saturated aqueous sodium hydrogen carbonate solution are then added. The organic phase is separated out by settling and dried over sodium sulfate and the solvent is evaporated off under reduced pressure. The residue is purified by chromatography on a column 80 g of silica gel, eluting with a mixture of 20% acetone in dichloromethane, to give 8.26 g of 4-nitrophenyl tetrahydro-2H-pyran-4-ylcarbamate in the form of a white powder.

m.p.: 174-176° C.

$^1$H NMR (CDCl$_3$) δ: 8.25 (d, 2H); 7.35 (d, 2H); 5.10 (broad d, 1H); 4.05 (m d, 2H); 3.85 (m, 1H); 3.50 (t d, 2H); 2.0 (m, 2H); 1.60 (m, 2H) ppm.

Step 5.2. Methyl 4-(3-cyanophenyl)-1H-pyrrole-3-carboxylate

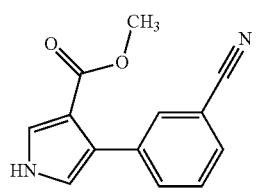 [SMILES: COC(=O)c1c[nH]cc1-c1cccc(C#N)c1]

To a suspension of 12.0 g (107 mmol) of potassium tert-butoxide at 60% in oil, in 100 ml of anhydrous tetrahydrofuran, is added dropwise a mixture of 13.3 g (71.1 mmol) of methyl(E)-3-(3-cyanophenyl)acrylate (CAS 193151-10-9) and 13.9 g (71.1 mmol) of tosylmethyl isocyanide (CAS 36635-61-7) dissolved in 100 ml of tetrahydrofuran, while maintaining the temperature of the reaction medium at about 25° C. The mixture is then stirred for 2 hours at room temperature, and is then partially concentrated under reduced pressure. This solution is then poured into ice-water and the reaction product is then extracted with dichloromethane. The organic phase is dried over sodium sulfate and the solvent is evaporated off under reduced pressure to give a brown solid, which is triturated in chloroform to give 10.8 g of methyl 4-(3-cyanophenyl)-1H-pyrrole-3-carboxylate in the form of a beige-coloured solid after cooling, filtering off and drying.

m.p.: 181-183° C.

$^1$H NMR (CDCl$_3$) δ: 8.6 (broad s, 1H); 7.70-7.80 (m, 2H); 7.40-7.60 (m, 3H); 6.85 (t, 1H); 3.75 (s, 3H) ppm.

Step 5.3. Methyl 5-chloro-4-(3-cyanophenyl)-1H-pyrrole-3-carboxylate

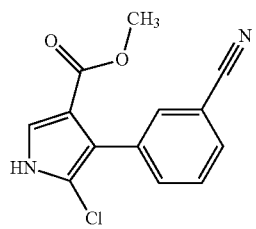 [SMILES: COC(=O)c1c[nH]c(Cl)c1-c1cccc(C#N)c1]

To a solution of 16.5 g (72.9 mmol) of methyl 4-(3-cyanophenyl)-1H-pyrrole-3-carboxylate in 150 ml of tetrahydrofuran are added portionwise 9.93 g (74.4 mmol) of N-chlorosuccinimide (CAS 128-09-6) and the mixture is then stirred for 6 hours at reflux. After cooling, 250 ml of water are added and the reaction product is extracted with ethyl acetate. The organic phase is dried over sodium sulfate and the solvent is evaporated off under reduced pressure to give 17.1 g of methyl 5-chloro-4-(3-cyanophenyl)-1H-pyrrole-3-carboxylate in the form of a beige-coloured powder after recrystallizing from acetonitrile, filtering off and drying.

m.p.: 194-196° C.

$^1$H NMR (CDCl$_3$) δ: 8.6 (broad s, 1H); 7.7-7.6 (m, 3H); 7.50 (m, 1H); 7.45 (d, 1H); 3.73 (s, 3H) ppm.

Step 5.4. Methyl 1-(2-tert-butoxycarbonylaminoethyl)-5-chloro-4-(3-cyanophenyl)-1H-pyrrole-3-carboxylate

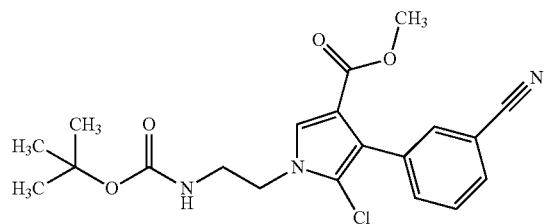 [SMILES: COC(=O)c1cn(CCNC(=O)OC(C)(C)C)c(Cl)c1-c1cccc(C#N)c1]

To a solution of 9.38 g (36.0 mmol) of methyl 5-chloro-4-(3-cyano-phenyl)-1H-pyrrole-3-carboxylate in 60 ml of acetonitrile are added 2.88 g (72.0 mmol) of powdered sodium hydroxide and 0.49 g (1.4 mmol) of tetrabutylammonium hydrogen sulfate, and the mixture is stirred vigorously for a few minutes, followed by adding 9.68 g (43.2 mmol) of tert-butyl(2-bromoethyl)carbamate (CAS 39684-80-5), and the mixture is then stirred for 6 hours at reflux. After cooling, the mixture is taken up in 250 ml of water and the product is extracted with ethyl acetate. The organic phase is then dried over sodium sulfate and the solvent is evaporated off under reduced pressure to give an orange-coloured oil, which is purified by chromatography on a column of 150 g of silica gel, eluting with a mixture of 2% methanol in dichloromethane, to give 13.5 g of methyl 1-(2-tert-butyloxycarbonylaminoethyl)-5-chloro-4-(3-cyanophenyl)-1H-pyrrole-3-carboxylate in the form of a yellow oil.

$^1$H NMR (CDCl$_3$) δ: 7.60-7.75 (m, 3H); 7.50 (d, 1H); 7.37 (s, 1H); 4.68 (broad s, 1H); 4.15 (m, 2H); 3.71 (s, 3H); 3.47 (q, 2H); 1.46 (s, 9H) ppm.

Step 5.5. Methyl 1-(2-aminoethyl)-5-chloro-4-(3-cyano-phenyl)-1H-pyrrole-3-carboxylate

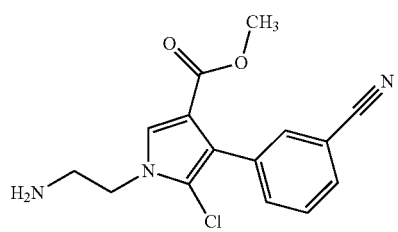 [SMILES: COC(=O)c1cn(CCN)c(Cl)c1-c1cccc(C#N)c1]

To a solution of 13.5 g (33.4 mmol) of methyl 1-(2-tert-butyloxycarbonylaminoethyl)-5-chloro-4-(3-cyanophenyl)-1H-pyrrole-3-carboxylate in 50 ml of methanol are added 80 ml (320 mmol) of 4N hydrochloric acid and the mixture is heated vigorously at 60° C. for 2 hours. 150 ml of water are then added and the solution is basified by adding aqueous ammonia. The product is extracted with dichloromethane, the organic phase is then dried over sodium sulfate and the solvent is evaporated off under reduced pressure to give a yellow oil, which is purified by chromatography on a column of 80 g of silica gel, eluting with a mixture of 0.3% aqueous ammonia and 3% methanol in dichloromethane, to give 8.4 g of methyl 1-(2-aminoethyl)-5-chloro-4-(3-cyanophenyl)-1H-pyrrole-3-carboxylate in the form of a white powder after crystallizing, triturating in diisopropyl ether, filtering off and drying.

m.p.: 111-113° C.

$^1$H NMR (CDCl$_3$) δ: 7.80-7.4 (m, 5H); 4.09 (t, 2H); 3.70 (s, 3H); 3.12 (t, 2H); 1.4 (broad s, 2H) ppm.

Step 5.6. Methyl 6-chloro-7-(3-cyanophenyl)-1,2,3,4-tetrahydropyrrolo[1,2-a]pyrazine-8-carboxylate

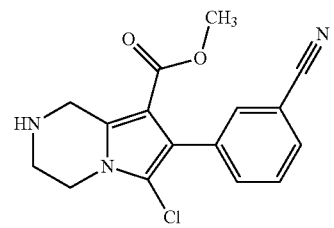 [SMILES: COC(=O)c1c(-c2cccc(C#N)c2)c(Cl)n2c1CNCC2]

To a solution of 8.41 g (27.7 mmol) of methyl 1-(2-aminoethyl)-5-chloro-4-(3-cyanophenyl)-1H-pyrrole-3-carboxylate in 20 ml of methanol are added 84 ml (340 mmol) of aqueous 4N hydrochloric acid solution. The formation of a white precipitate is rapidly observed and the medium then becomes clear, while the mixture is heated to 90° C. and 0.92 g (10 mmol) of paraformaldehyde is added. Heating is continued at 90° C. for 4 hours. After cooling, the reaction medium is poured into 200 ml of water and the solution is basified by adding aqueous ammonia. The product is extracted with ethyl acetate, the organic phase is dried over sodium sulfate and the solvent is evaporated off under reduced pressure to give an orange-coloured oil, which is chromatographed on a column of 80 g of silica gel, eluting with a mixture of 2% methanol in dichloromethane, to give 7.1 g of methyl 6-chloro-7-(3-cyanophenyl)-1,2,3,4-tetrahydropyrrolo[1,2-a]pyrazine-8-carboxylate in the form of a yellow oil.

$^1$H NMR (CDCl$_3$) δ: 7.65-7.40 (m, 4H); 4.35 (s, 2H); 3.90 (t, 2H); 3.65 (s, 3H); 3.35 (t, 2H) ppm.

Step 5.7. 2-tert-Butyl 8-methyl 6-chloro-7-(3-cyanophenyl)-3,4-dihydropyrrolo[1,2-a]pyrazine-2,8 (1H)-dicarboxylate

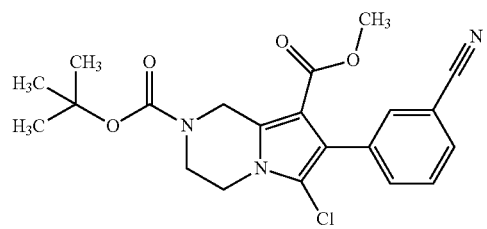 [SMILES: COC(=O)c1c(-c2cccc(C#N)c2)c(Cl)n2c1CN(C(=O)OC(C)(C)C)CC2]

To a solution of 7.10 g (22.5 mmol) of methyl 6-chloro-7-(3-cyanophenyl)-1,2,3,4-tetrahydropyrrolo[1,2-a]pyrazine-8-carboxylate in 50 ml of dichloromethane are added slowly 5.40 g (24.7 mmol) of di-tert-butyl dicarbonate (CAS 24424-99-5) dissolved in about 20 ml of dichloromethane. After stirring for 1 hour at room temperature, the solvent is evaporated off under reduced pressure to give a yellow oil, which is purified by chromatography on a column of 80 g of silica gel, eluting with a mixture of 20% ethyl acetate in cyclohexane to give 7.5 g of 2-tert-butyl 8-methyl 6-chloro-7-(3-cyanophenyl)-3,4-dihydropyrrolo[1,2-a]pyrazine-2,8(1H)-dicarboxylate in the form of a transparent oil that crystallizes from methanol.

m.p.: 154-156° C.

$^1$H NMR (CDCl$_3$) δ: 7.65-7.40 (m, 4H); 4.90 (s, 2H); 3.9 (2m, 4H); 3.70 (s, 3H); 1.50 (s, 9H) ppm.

Step 5.8. 2-(tert-Butoxycarbonyl)-6-chloro-7-(3-cyanophenyl)-1,2,3,4-tetrahydropyrrolo[1,2-a]pyrazine-8-carboxylic acid

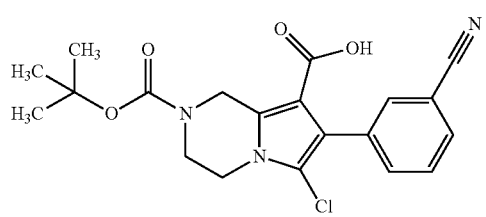

To a suspension of 5.50 g (13.2 mmol) of 2-tert-butyl 8-methyl 6-chloro-7-(3-cyanophenyl)-3,4-dihydropyrrolo[1,2-a]pyrazine-2,8(1H)-dicarboxylate in 60 ml of a mixture of methanol, water and tetrahydrofuran (1:1:2) is added 0.38 g (15.9 mmol) of lithium hydroxide, and the mixture is heated at 60° C. for 18 hours. The mixture is then taken up in 100 ml of dichloromethane and 100 ml of water, and is then acidified by addition of aqueous 1N sulfuric acid. The organic phase is separated out and dried over sodium sulfate, and the solvent is evaporated off under reduced pressure to give a yellow solid, which is purified by chromatography on a column of 80 g of silica gel, eluting with a mixture of 2% methanol in dichloromethane, to give 3.35 g of 2-(tert-butyloxycarbonyl)-6-chloro-7-(3-cyanophenyl)-1,2,3,4-tetrahydropyrrolo[1,2-a]pyrazine-8-carboxylic acid in the form of a white powder after triturating in acetonitrile, filtering off and drying.

m.p.: 208-210° C.

$^1$H NMR (DMSO-d$_6$) δ: 12.1 (broad s, 1H); 7.8-7.5 (m, 4H); 4.80 (s, 2H); 3.95 (m, 2H); 3.80 (m, 2H); 1.45 (s, 9H) ppm.

Step 5.9. tert-Butyl 6-chloro-7-(3-cyanophenyl)-8-(1H-imidazol-1-ylcarbonyl)-3,4-dihydropyrrolo[1,2-a]pyrazine-2(1H)-carboxylate

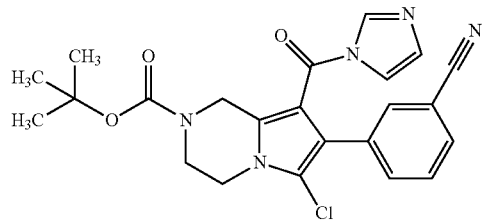 [SMILES: CC(C)(C)OC(=O)N1CCn2c(Cl)c(-c3cccc(C#N)c3)c(C(=O)n3ccnc3)c2C1]

To a solution of 3.1 g (7.71 mmol) of 2-(tert-butyloxycarbonyl)-6-chloro-7-(3-cyanophenyl)-1,2,3,4-tetrahydropyrrolo[1,2-a]pyrazine-8-carboxylic acid in 20 ml of tetrahydrofuran are added 1.38 g (8.49 mmol) of carbonyl-diimidazole (CAS 530-62-1). After reaction for 2 hours at 60° C., the mixture is cooled and concentrated under reduced pressure. The residue is taken up in 60 ml of water and the product is extracted with dichloromethane. The organic phase is dried over sodium sulfate and the solvent is evaporated off under reduced pressure to give a yellow oil, which is purified by chromatography on a column of 80 g of silica gel, eluting with a mixture of 2% methanol in dichloromethane, to give 3.38 g of tert-butyl 6-chloro-7-(3-cyanophenyl)-8-(1H-imidazol-1-ylcarbonyl)-3,4-dihydropyrrolo[1,2-a]pyrazine-2(1H)-carboxylate in the form of a colourless oil.

$^1$H NMR (CDCl$_3$) δ: 7.60 (m, 1H); 7.5 (m, 2H); 7.30 (m, 2H); 7.2 (m, 1H); 6.80 (m, 1H); 4.80 (s, 2H); 4.05 (t, 2H); 3.95 (m, 2H); 1.50 (s, 9H) ppm.

Step 5.10. tert-Butyl 8-carbamoyl-6-chloro-7-(3-cyanophenyl)-3,4-dihydropyrrolo[1,2-a]pyrazine-2(1H)-carboxylate

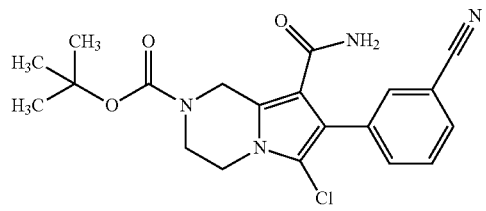 [SMILES: CC(C)(C)OC(=O)N1CCn2c(Cl)c(-c3cccc(C#N)c3)c(C(N)=O)c2C1]

To a solution of 3.28 g (7.26 mmol) of tert-butyl 6-chloro-7-(3-cyanophenyl)-8-(1H-imidazol-1-ylcarbonyl)-3,4-dihydropyrrolo[1,2-a]pyrazine-2(1H)-carboxylate in 4 ml of dimethylformamide in an autoclave are added 6 ml of 33% aqueous ammonia. The mixture is stirred for 3 hours at 110° C. and, after cooling, is then poured into 80 ml of water and the solid is separated out by filtration. The solid is taken up in dichloromethane, the solution is then dried over sodium sulfate and the solvent is evaporated off under reduced pressure to give 2.9 g of tert-butyl 8-carbamoyl-6-chloro-7-(3-cyanophenyl)-3,4-dihydropyrrolo[1,2-a]pyrazine-2(1H)-carboxylate after drying.

m.p.: 206-208° C.

$^1$H NMR (DMSO-d$_6$) δ: 7.85-7.75 (m, 1H); 7.70 (m, 1H); 7.65-7.60 (m, 2H); 7.1 (broad s, 1H); 6.45 (broad s, 1H); 4.70 (s, 2H); 3.95 (m, 2H); 3.8 (m, 2H); 1.45 (s, 9H) ppm.

Step 5.11. 6-Chloro-7-(3-cyanophenyl)-1,2,3,4-tetrahydro-pyrrolo[1,2-a]pyrazine-8-carboxamide

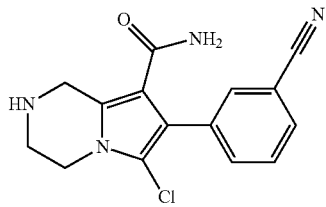 [SMILES: N#Cc1cccc(-c2c(C(N)=O)c3n(c2Cl)CCNC3)c1]

To a solution of 2.90 g (7.23 mmol) of tert-butyl 8-carbamoyl-6-chloro-7-(3-cyanophenyl)-3,4-dihydropyrrolo[1,2-a]pyrazine-2(1H)-carboxylate in 7 ml of dichloromethane are added slowly 7 ml (72 mmol) of trifluoroacetic acid. After stirring for 1 hour at room temperature, the solvent is evaporated off under reduced pressure, the residue is taken up in water and the aqueous phase is basified by addition of aqueous ammonia. The white solid formed is separated out by filtration, rinsed with water and triturated in acetonitrile to give 1.7 g of 6-chloro-7-(3-cyanophenyl)-1,2,3,4-tetrahydro-pyrrolo[1,2-a]pyrazine-8-carboxamide in the form of a white powder after separating out by filtration and drying under reduced pressure.

m.p.: 151-153° C.

$^1$H NMR (DMSO-$d_6$) δ: 7.80-7.65 (m, 1H); 7.65 (m, 1H); 7.6-7.5 (m, 2H); 7.0 (broad s, 1H); 6.5 (broad s, 1H); 4.00 (s, 2H); 3.75 (t, 2H); 3.10 (t, 2H) ppm.

Step 5.12. 6-Chloro-7-(3-cyanophenyl)-N²-(tetrahydro-2H-pyran-4-yl)-3,4-dihydropyrrolo[1,2-a]pyrazine-2,8(1H)-dicarboxamide

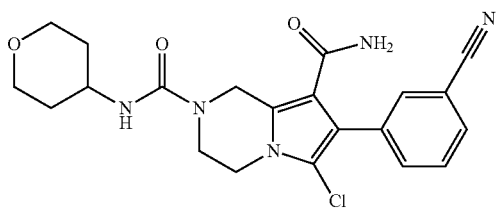 [SMILES: N#Cc1cccc(-c2c(C(N)=O)c3n(c2Cl)CCN(C(=O)NC2CCOCC2)C3)c1]

A suspension of 0.67 g (2.23 mmol) of 6-chloro-7-(3-cyanophenyl)-1,2,3,4-tetrahydropyrrolo[1,2-a]pyrazine-8-carboxamide, 0.712 g (2.67 mmol) of 4-nitrophenyl tetrahydro-2H-pyran-4-ylcarbamate and 0.616 g (1.12 mmol) of potassium carbonate in 10 ml of acetonitrile is heated at 65° C. for 1 hour 30 minutes. After cooling, the mixture is concentrated under reduced pressure, the residue is diluted with dichloromethane and the solution is washed with aqueous 1N sodium hydroxide solution. The organic phase is washed with water, dried over sodium sulfate and filtered, and the solvent is evaporated off under reduced pressure. The residue is purified by chromatography on a column of 40 g of silica gel, eluting with a mixture of 2 to 5% methanol in dichloromethane, to give 0.79 g of 6-chloro-7-(3-cyanophenyl)-N²-(tetrahydro-2H-pyran-4-yl)-3,4-dihydropyrrolo[1,2-a]pyrazine-2,8(1H)-dicarboxamide in the form of a whitish powder after recrystallizing from 100 ml of ethanol, filtering off and drying under reduced pressure.

m.p.: 236-238° C.

$^1$H NMR (DMSO-$d_6$) δ: 7.80 (m, 1H); 7.70 (m, 1H); 7.65 (, 2H); 7.05 (broad s, 1H); 6.65 (d, 1H); 6.50 (broad s, 1H); 4.75 (s, 2H); 3.95-3.75 (m, 6H); 3.70 (m, 1H); 3.45 (m, 2H); 1.70 (m, 2H); 1.50 (m, 2H) ppm.

Example 6 (Compound 58)

N²-(tert-Butyl)-6-fluoro-7-phenyl-3,4-dihydropyrrolo[1,2-a]pyrazine-2,8(1H)-dicarboxamide

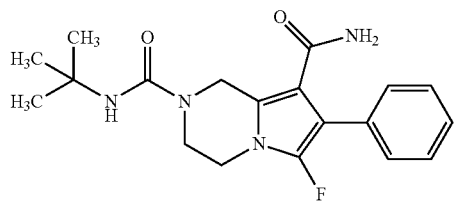 [SMILES: CC(C)(C)NC(=O)N1CCn2c(F)c(-c3ccccc3)c(C(N)=O)c2C1]

Step 6.1. 5-Fluoro-4-phenyl-1H-pyrrole-3-carbonitrile

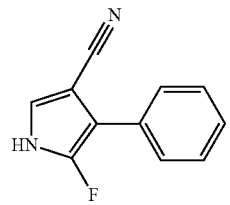 [SMILES: N#Cc1c[nH]c(F)c1-c1ccccc1]

To a solution of 9.50 g (56.5 mmol) of 4-phenyl-1H-pyrrole-3-carbonitrile (CAS 40167-37-1) in 300 ml of acetonitrile are added portionwise 24.0 g (67.8 mmol) of 1-chloromethyl-4-fluoro-1,4-diazoniabicyclo[2.2.2]octane bis(tetrafluoroborate) (SelectFluor—CAS 140681-55-6), with a certain amount of exothermicity being observed. The mixture is stirred for 18 hours at 60° C. After cooling, the reaction medium is concentrated under reduced pressure and the residue is then taken up in 500 ml of ethyl acetate. The solution is washed twice with 250 ml of water and then with saturated aqueous sodium chloride solution. The organic phase is dried over sodium sulfate and the solvent is evaporated off under reduced pressure to give a brown oil, which is chromatographed on a column of silica gel, eluting with a mixture of 15% ethyl acetate in cyclohexane, to give 3.75 g of 5-fluoro-4-phenyl-1H-pyrrole-3-carbonitrile in the form of a red oil after drying, which product is used as obtained for the rest of the synthesis.

$^1$H NMR (CDCl$_3$) δ: 8.7 (broad s, 1H); 7.7-7.3 (m, 5H); 6.95 (m, 1H) ppm.

Step 6.2. tert-Butyl {2-[4-cyano-2-fluoro-3-phenyl-1H-pyrrol-1-yl]ethyl}carbamate

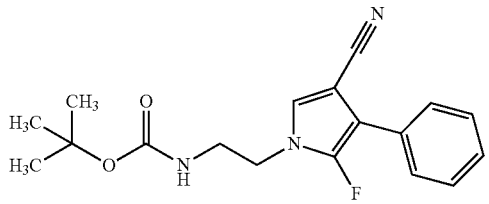 [SMILES: CC(C)(C)OC(=O)NCCn1cc(C#N)c(-c2ccccc2)c1F]

To a solution of 3.75 g (20.1 mmol) of 5-fluoro-4-phenyl-1H-pyrrole-3-carbonitrile in 101 ml of acetonitrile are added 1.6 g (40 mmol) of finely ground sodium hydroxide and 0.27 g (0.81 mmol) of tetrabutylammonium hydrogen sulfate, and the mixture is stirred vigorously for a few minutes, followed by adding 5.42 g (24.2 mmol) of tert-butyl(2-bromoethyl) carbamate (CAS 39684-80-5), and the mixture is then stirred for 18 hours at 90° C. After cooling, the solvent is evaporated off under reduced pressure and the residue is taken up in twice 125 ml of water. The product is extracted with ethyl acetate. The organic phase is then washed with saturated aqueous sodium chloride solution and dried over sodium sulfate, and the solvent is evaporated off under reduced pressure. The residue is purified by chromatography on a column of silica gel, eluting with a mixture of 15 to 50% ethyl acetate in cyclohexane, to give 2.5 g of tert-butyl{2-[4-cyano-2-fluoro-3-phenyl-1H-pyrrol-1-yl]ethyl}carbamate in the form of a brown oil.

$^1$H NMR (CDCl$_3$) δ: 7.65 (d, 2H); 7.55 (t, 2H); 7.30 (d, 1H); 4.7 (broad s, 1H); 4.05 (m, 2H); 3.45 (m, 2H); 1.46 (s, 9H) ppm.

Step 6.3. 6-Fluoro-7-phenyl-1,2,3,4-tetrahydropyrrolo-[1,2-a]pyrazine-8-carbonitrile

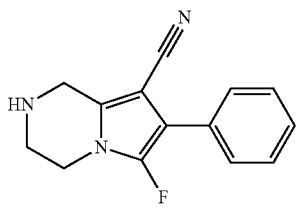 [SMILES: N#Cc1c(-c2ccccc2)c(F)n2c1CNCC2]

To a suspension of 2.50 g (7.59 mmol) of tert-butyl{2-[2-fluoro-4-cyano-3-phenyl-1H-pyrrol-1-yl]ethyl}carbamate in 5 ml of ethanol are added slowly 25 ml (100 mmol) of aqueous 4N hydrochloric acid solution and 0.25 g (2.8 mmol) of paraformaldehyde. The mixture is heated at 90° C. for a further 2 hours. After cooling, the reaction medium is basified slowly by adding aqueous ammonia and the product is extracted with dichloromethane, the organic phase is dried over sodium sulfate and the solvent is evaporated off under reduced pressure. The black oil obtained is purified by chromatography on a column of silica gel, eluting with a mixture of 2 to 5% methanol in dichloromethane, to give 0.75 g of 6-fluoro-7-phenyl-1,2,3,4-tetrahydropyrrolo[1,2-a]pyrazine-8-carbonitrile in the form of a brown oil after drying.

$^1$H NMR (CDCl$_3$) δ: 7.7 (m, 1H); 7.5-7.3 (m, 4H); 4.20 (s, 2H); 3.90 (t, 2H); 3.30 (t, 2H); 1.8 (bs, 1H) ppm.

Step 6.4. N-tert-Butyl-8-cyano-6-fluoro-7-phenyl-3,4-dihydropyrrolo[1,2-a]pyrazine-2(1H)-carboxamide

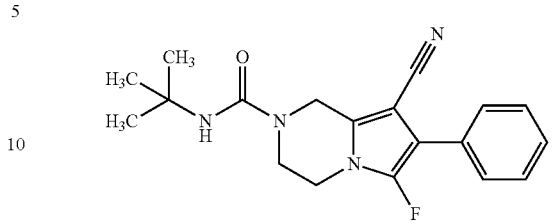

To a solution cooled to 0° C. of 0.75 g (3.1 mmol) of 6-fluoro-7-phenyl-1,2,3,4-tetrahydropyrrolo[1,2-a]pyrazine-8-carbonitrile in 50 ml of dichloromethane are added 1.4 ml (10 mmol) of triethylamine and then 0.37 g (3.7 mmol) of tert-butyl isocyanate (CAS1609-86-5) dropwise. After stirring for 2 hours at room temperature, the medium is poured into water, the organic phase is separated out and dried over sodium sulfate, and the solvent is evaporated off under reduced pressure to give a solid in the form of a green foam, which is purified by chromatography on a column of silica gel, eluting with a mixture of 20 to 50% ethyl acetate in cyclohexane, to give 0.36 g of N-tert-butyl-8-cyano-6-fluoro-7-phenyl-3,4-dihydropyrrolo[1,2-a]pyrazine-2(1H)-carboxamide in the form of an orange-coloured gummy solid.

$^1$H NMR (CDCl$_3$) δ: 7.65 (m, 2H); 7.45 (m, 2H); 7.35 (m, 1H); 4.65 (s, 2H); 4.5 (broad s, 1H); 3.95 (m, 2H); 1.4 (s, 9H) ppm.

Step 6.5. N$^2$-(tert-Butyl)-6-fluoro-7-phenyl-3,4-dihydropyrrolo[1,2-a]pyrazine-2,8(1H)-dicarboxamide

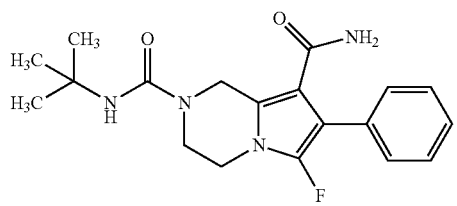 [SMILES: CC(C)(C)NC(=O)N1CCn2c(F)c(-c3ccccc3)c(C(N)=O)c2C1]

To a solution of 0.360 g (1.06 mmol) of N-tert-butyl-6-fluoro-8-cyano-7-phenyl-3,4-dihydropyrrolo[1,2-a]pyrazine-2(1H)-carboxamide in 4.2 ml of methanol is added 0.1 ml (1.1 mmol) of aqueous 35% sodium hydroxide solution and then 0.28 ml (3.2 mmol) of 35-volumes aqueous hydrogen peroxide solution. After stirring for 2 hours at 60° C., a further 0.05 ml (0.5 mmol) of 35-volumes aqueous hydrogen peroxide solution is added and the mixture is stirred for 16 hours at 60° C. After cooling, 0.25 g of sodium thiosulfate dissolved in 0.5 ml of water is added and the heterogeneous mixture is diluted with 75 ml of ethyl acetate. The organic phase is separated out, washed twice with 25 ml of water and then with 25 ml of saturated aqueous sodium chloride solution, after which it is dried over sodium sulfate. The solvent is evaporated off under reduced pressure to give a yellow oil, which is purified by chromatography on a column of silica gel, eluting with a mixture of 2 to 6% methanol in dichloromethane, to give 0.06 g of 6-fluoro-7-phenyl-N$^2$-(tert-butyl)-3,4-dihydropyrrolo[1,2-a]pyrazine-2,8(1H)-dicarboxamide in the form of a solid after triturating in diisopropyl ether, filtering off and drying.

m.p.: 213-215° C.

$^1$H NMR (CDCl$_3$) δ: 7.4 (m, 5H); 7.05 (bs, 1H); 6.15 (bs and s, 2H); 4.70 (s, 2H); 3.90 (m, 2H); 3.75 (m, 2H); 1.30 (s, 9H) ppm.

Example 7 (Compound 60)

N$^2$-tert-Butyl-6-chloro-7-phenyl-3,4-dihydropyrrolo[1,2-a]pyrazine-2,8(1H)-dicarboxamide

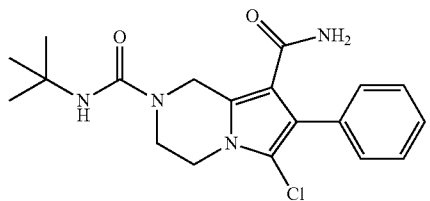 [SMILES: CC(C)(C)NC(=O)N1CCn2c(Cl)c(-c3ccccc3)c(C(N)=O)c2C1]

The synthesis of this compound is also described in Example 4.

Step 7.1.: tert-Butyl 8-cyano-3,4-dihydropyrrolo[1,2-a]pyrazine-2(1H)-carboxylate

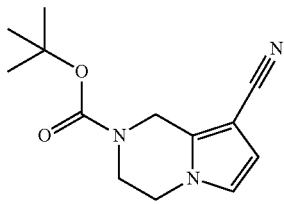 [SMILES: CC(C)(C)OC(=O)N1CCn2ccc(C#N)c2C1]

To a solution under nitrogen of 28.7 g (102 mmol) of sodium 4-(tert-butyloxycarbonyl)-1-formylpiperazine-2-carboxylate (CAS 1108698-36-7) in 1 l of dichloromethane are added 21.5 g (113 mmol) of p-toluenesulfonyl chloride. After stirring for 40 minutes, 8.2 ml (102 mmol) of 2-chloroacrylonitrile are added. After stirring for 40 minutes, 32.8 ml (235 mmol) of triethylamine are added dropwise and the mixture is stirred overnight at room temperature, and then refluxed for 1 hour. The solution is then cooled to room temperature. 150 ml of water are added. The organic phase is separated out by settling, washed twice with 100 ml of water, dried over sodium sulfate and filtered, and concentrated under reduced pressure. The residue obtained is chromatographed on a column of silica gel, eluting with a mixture of 0 to 10% ethyl acetate in dichloromethane, to give 17.5 g of tert-butyl 8-cyano-3,4-dihydropyrrolo[1,2-a]pyrazine-2(1H)-carboxylate in the form of a white solid after dissolving in a mixture of cyclohexane and dichloromethane and then precipitating by slow concentration and drying under reduced pressure.

m.p.: 97° C.

$^1$H NMR (CDCl$_3$) δ: 6.60 (d, 1H); 6.45 (d, 1H); 4.75 (s, 2H); 4.0 (m, 2H); 3.9 (m, 2H); 1.55 (s, 9H) ppm.

Step 7.2. tert-Butyl 8-carbamoyl-3,4-dihydropyrrolo[1,2-a]pyrazine-2(1H)-carboxylate

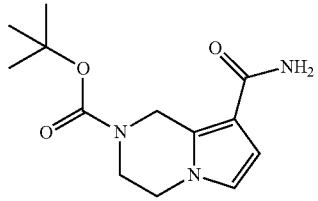 [SMILES: CC(C)(C)OC(=O)N1CCn2ccc(C(N)=O)c2C1]

To a solution of 26.7 g (108 mmol) of tert-butyl 8-cyano-3,4-dihydropyrrolo[1,2-a]pyrazine-2(1H)-carboxylate in 490 ml of methanol are added 80 ml (864 mmol) of concentrated aqueous 32% sodium hydroxide and 4.0 g (41 mmol) of aqueous 35% hydrogen peroxide solution. The reaction medium is heated at 55° C. for 2 hours. 4 times 4.0 g (41 mmol) of aqueous 35% hydrogen peroxide solution are then added every 2 hours and heating is then continued at 55° C. for 18 hours. The medium is then treated with an aqueous solution of 30 g (190 mmol) of sodium thiosulfate in 250 ml of water and the reaction mixture is stirred for 1 hour and then partially concentrated under reduced pressure. The product is extracted with 350 ml and then twice 100 ml of dichloromethane, and the organic phases are combined, dried over sodium sulfate, filtered and concentrated under reduced pressure. The residue is dissolved in a mixture of dichloromethane and ethyl acetate and then precipitated by slow concentration to give 21.1 g of tert-butyl 8-carbamoyl-3,4-dihydropyrrolo[1,2-a]pyrazine-2(1H)-carboxylate in the form of a white solid after drying in an oven at 60° C. under reduced pressure.

m.p.: 181° C.

$^1$H NMR (CDCl$_3$) δ: 6.55 (d, 1H); 6.30 (d, 1H); 5.5 (bs, 2H); 4.95 (s, 2H); 4.0 (m, 2H); 3.85 (m, 2H); 1.50 (s, 9H) ppm.

Step 7.3.: tert-Butyl 8-carbamoyl-6-chloro-3,4-dihydropyrrolo[1,2-a]pyrazine-2(1H)-carboxylate

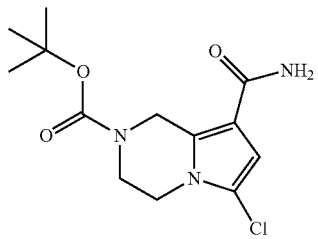 [SMILES: CC(C)(C)OC(=O)N1CCn2c(Cl)cc(C(N)=O)c2C1]

To a solution under nitrogen of 21.1 g (79.6 mmol) of tert-butyl 8-carbamoyl-3,4-dihydropyrrolo[1,2-a]pyrazine-2(1H)-carboxylate in 600 ml of dichloromethane, cooled to −40° C., is added dropwise a solution of 10.6 g (79.6 mmol) of N-chlorosuccinimide in 200 ml of dichloromethane over about 40 minutes. Stirring is continued for 6 hours at a temperature of −40° C., 150 ml of water are then added and the reaction medium is allowed to warm to room temperature. The product is isolated by filtration and is washed with water to give 17.5 g of tert-butyl 8-carbamoyl-6-chloro-3,4-dihydropyrrolo[1,2-a]pyrazine-2(1H)-carboxylate in the form of a whitish solid after drying under reduced pressure at 40° C. in the presence of phosphorus pentoxide.

m.p.=223-225° C.

¹H NMR (DMSO) δ: 7.35 (broad s, 1H); 6.85 (broad s, 1H); 6.75 (s, 1H); 4.75 (s, 2H); 3.85 (m, 2H); 3.75 (m, 2H); 1.45 (s, 9H) ppm.

Step 7.4. tert-Butyl 7-bromo-8-carbamoyl-6-chloro-3,4-dihydropyrrolo[1,2-a]pyrazine-2(1H)-carboxylate

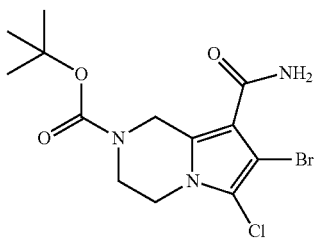 [SMILES: CC(C)(C)OC(=O)N1CCn2c(Cl)c(Br)c(C(N)=O)c2C1]

To a solution of 10.5 g (35.1 mmol) of tert-butyl 8-carbamoyl-6-chloro-3,4-dihydropyrrolo[1,2-a]pyrazine-2(1H)-carboxylate in 1 l of a mixture of 50% ethyl acetate in dichloromethane precooled to 0° C. is added slowly a solution of 6.90 g (38.6 mmol) of N-bromosuccinimide in 200 ml of dichloromethane. The reaction is stirred for 5 hours at 0° C. and then for 12 hours while allowing the temperature to return to room temperature. 300 ml of water are then added, the organic phase is separated out by settling and the aqueous phase is then washed with twice 200 ml of ethyl acetate. The organic phases are combined and partially concentrated under reduced pressure. The solution is taken up in 60 ml of water and the organic solvents are removed by evaporation under reduced pressure. The insoluble matter suspended in water is isolated by filtration, washed with water and then dried under reduced pressure in the presence of phosphorus pentoxide. The residue obtained is chromatographed on a column of silica gel, eluting with a mixture of 5 to 50% ethyl acetate in dichloromethane, to give 5.0 g of tert-butyl 7-bromo-8-carbamoyl-6-chloro-3,4-dihydropyrrolo[1,2-a]pyrazine-2(1H)-carboxylate in the form of a white solid after triturating in ethyl acetate and drying at 60° C. under reduced pressure.

m.p.: 214-216° C.

¹H NMR (CDCl₃) δ: 6.7 (broad s, 1H); 5.5 (broad s, 1H); 5.00 (s, 2H); 3.9 (m, 4H); 1.50 (s, 9H) ppm.

Step 7.5. tert-Butyl 8-carbamoyl-6-chloro-7-phenyl-3,4-dihydropyrrolo[1,2-a]pyrazine-2(1H)-carboxylate

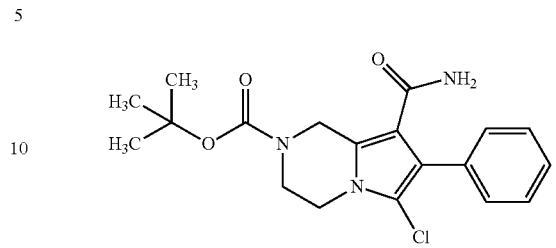

To a solution under nitrogen of 3.78 g (9.98 mmol) of tert-butyl 7-bromo-8-carbamoyl-6-chloro-3,4-dihydropyrrolo[1,2-a]pyrazine-2(1H)-carboxylate in 160 ml of tetrahydrofuran are added 1.34 g (11.0 mmol) of benzeneboronic acid (CAS 98-80-6), 8 ml of water, 9.76 g (30.0 mmol) of caesium carbonate and 0.98 g (1.20 mmol) of a complex of 1,1'-bis(diphenylphosphino)ferrocenedichloropalladium (II) and dichloromethane (PdCl₂(dppf).CH₂Cl₂—CAS 95464-05-4). The mixture is stirred for 6 hours at 100° C. and then for 15 hours at 80° C., then cooled to room temperature and filtered through Celite™. The Celite is rinsed with 100 ml of ethyl acetate and 30 ml of water are added to the combined filtrates. The organic phase is separated out by settling, dried over sodium sulfate, filtered and concentrated under reduced pressure. The residue obtained is chromatographed on a column of silica gel, eluting with a mixture of 5 to 50% ethyl acetate in dichloromethane, to give 1.50 g of tert-butyl 8-carbamoyl-6-chloro-7-phenyl-3,4-dihydropyrrolo[1,2-a]pyrazine-2(1H)-carboxylate in the form of a white solid after recrystallization from ethyl acetate and drying at 60° C. under reduced pressure.

m.p.: 178-180° C.

¹H NMR (CDCl₃) δ: 7.4-7.25 (m, 5H); 5.1 (broad s, 2H); 4.9 (s, 2H); 3.85 (m, 4H); 1.45 (s, 9H) ppm.

Step 7.6. 6Chloro-7-phenyl-1,2,3,4-tetrahydropyrrolo[1,2-a]pyrazine-8-carboxamide hydrochloride

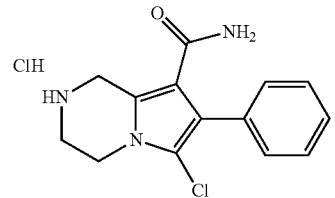 [SMILES: Cl ; NC(=O)c1c(-c2ccccc2)c(Cl)n2c1CNCC2]

To a solution cooled to about 0° C. of 5.99 g (15.9 mmol) of tert-butyl 8-carbamoyl-6-chloro-7-phenyl-3,4-dihydropyrrolo[1,2-a]pyrazine-2(1H)-carboxylate in 50 ml of dichloromethane and 200 ml of methanol are added portionwise 12.6 g (116 mmol) of chlorotrimethylsilane. The mixture is stirred for 16 hours at room temperature and the reaction medium is then concentrated under reduced pressure and co-evaporated twice with ethyl acetate. The residue is crystallized from ethyl acetate to give 4.88 g of 6-chloro-7-phenyl-1,2,3,4-tetrahydropyrrolo[1,2-a]pyrazine-8-carboxamide hydrochloride in the form of a white solid after drying at 60° C. under reduced pressure.

m.p.: 227-230° C. (decomposition)

¹H NMR (DMSO) δ: 9.5 (broad s, 2H); 7.55-7.30 (m, 5H); 7.20 (broad s, 1H); 4.55 (s, 2H); 4.15 (m, 2H); 3.65 (m, 2H) ppm.

Step 7.7. $N^2$-tert-Butyl-6-chloro-7-phenyl-3,4-dihydropyrrolo[1,2-a]pyrazine-2,8(1H)-dicarboxamide

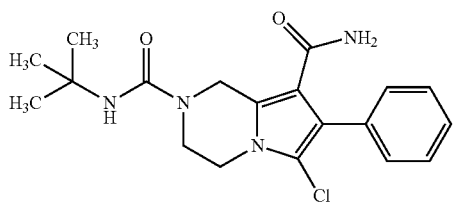

To a solution under nitrogen and cooled to about 0° C. of 2.06 g (6.6 mmol) of 8-carbamoyl-6-chloro-7-phenyl-1,2,3,4-dihydropyrrolo[1,2-a]pyrazine hydrochloride in 60 ml of dichloromethane are added 2.76 ml (19.8 mmol) of triethylamine, and then 0.90 ml (7.92 mmol) of tert-butyl isocyanate. The solution is stirred for 4 hours at room temperature and 20 ml of water are then added. The organic phase is separated out by settling, washed twice with 20 ml of water, dried over sodium sulfate and filtered, and concentrated under reduced pressure. The residue is chromatographed on a column of silica gel, eluting with a mixture of 5 to 50% ethyl acetate in dichloromethane, and the product obtained is recrystallized from ethyl acetate, to give 0.46 g of $N^2$-tert-butyl-6-chloro-7-phenyl-3,4-dihydropyrrolo[1,2-a]pyrazine-2,8(1H)-dicarboxamide in the form of a white solid after drying at 60° C. under reduced pressure.

m.p.: 192-195° C.

$^1$H NMR (DMSO) δ: 7.45 (m, 2H); 7.35 (m, 3H); 7.0 (broad s, 1H); 6.15 (s, 1H); 5.85 (broad s, 1H); 4.70 (s, 2H); 3.90 (m, 2H); 3.80 (m, 2H); 1.30 (s, 9H) ppm.

Example 8 (Compound 1)

$N^2$-tert-Butyl-7-phenyl-3,4-dihydropyrrolo[1,2-a]pyrazine-2,8(1H)-dicarboxamide

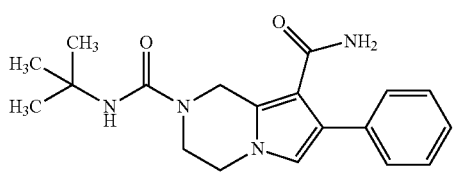 [SMILES: CC(C)(C)NC(=O)N1CCn2cc(-c3ccccc3)c(C(N)=O)c2C1]

A mixture of 0.866 g (2.31 mmol) of $N^2$-tert-butyl-6-chloro-7-phenyl-3,4-dihydropyrrolo[1,2-a]pyrazine-2,8(1H)-dicarboxamide, 6.0 g (95 mmol) of ammonium formate and 0.20 g (0.09 mmol) of 10% palladium-on-charcoal containing 50% water in 50 ml of methanol is refluxed for 6 hours. After cooling, the mixture is filtered through Celite and the Celite is rinsed with dichloromethane. The filtrate is then concentrated under reduced pressure and the residue is taken up in dichloromethane. The solution is washed with water, dried over sodium sulfate and then concentrated under reduced pressure. The product is then purified by chromatography on a column of 40 g of silica gel, eluting with a mixture of 95 to 50% ethyl acetate in dichloromethane, to give 0.31 g of $N^2$-tert-butyl-7-phenyl-3,4-dihydropyrrolo[1,2-a]pyrazine-2,8(1H)-dicarboxamide in the form of a white solid after crystallizing from diethyl ether and drying.

m.p.: 156-158° C.

$^1$H NMR (DMSO-d$_6$) δ: 7.4 (m, 4H); 7.25 (m, 1H); 6.9 (broad s, 1H); 6.55 (s, 1H); 6.2 (broad s, 1H); 6.05 (s, 1H); 4.70 (s, 2H); 3.95 (m, 2H); 3.70 (m, 2H); 1.33 (s, 9H) ppm.

Example 9 (Compound 65)

$N^2$-tert-Butyl-6-chloro-7-(3-cyanophenyl)-3,4-dihydropyrrolo[1,2-a]pyrazine-2,8(1H)-dicarboxamide

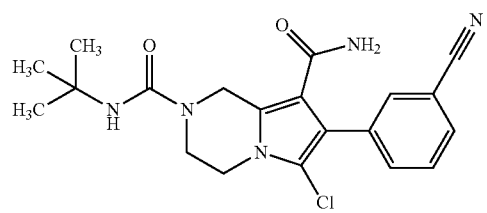 [SMILES: CC(C)(C)NC(=O)N1CCn2c(Cl)c(-c3cccc(C#N)c3)c(C(N)=O)c2C1]

Step 9.1. tert-Butyl 8-carbamoyl-6-chloro-7-(3-cyano-phenyl)-3,4-dihydropyrrolo[1,2-a]pyrazine-2(1H)-carboxylate

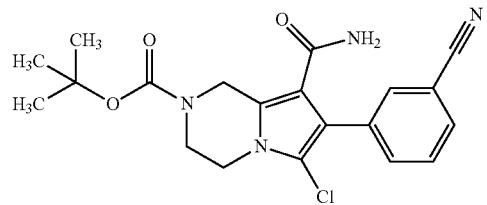 [SMILES: CC(C)(C)OC(=O)N1CCn2c(Cl)c(-c3cccc(C#N)c3)c(C(N)=O)c2C1]

To a solution under nitrogen of 6.50 g (17.2 mmol) of tert-butyl 7-bromo-8-carbamoyl-6-chloro-3,4-dihydropyrrolo[1,2-a]pyrazine-2(1H)-carboxylate in 200 ml of tetrahydrofuran are added 2.52 g (17.2 mmol) of 3-cyanophenylboronic acid (CAS 150255-96-2), 10 ml of water, 16.8 g (52.4 mmol) of caesium carbonate and 1.68 g (2.06 mmol) of a complex of 1,1'-bis(diphenylphosphino)ferrocenedichloropalladium (II) and dichloromethane (PdCl$_2$(dppf).CH$_2$Cl$_2$—CAS 95464-05-4). The mixture is stirred for 6 hours at 100° C. and then for 15 hours at 80° C., then cooled to room temperature and filtered through Celite™. The Celite is rinsed with 200 ml of ethyl acetate and 30 ml of water are added to the combined filtrates. The organic phase is separated out by settling, dried over sodium sulfate, filtered and concentrated under reduced pressure. The residue obtained is chromatographed on a column of silica gel, eluting with a mixture of 2 to 50% ethyl acetate in dichloromethane, to give 3.69 g of tert-butyl 8-carbamoyl-6-chloro-7-(3-cyanophenyl)-3,4-dihydropyrrolo[1,2-a]pyrazine-2(1H)-carboxylate in the form of a white solid after recrystallization from ethyl acetate and drying at 60° C. under reduced pressure.

m.p.: 209-210° C.

$^1$H NMR (CDCl$_3$) δ: 7.8-7.55 (m, 4H); 5.1 (broad s, 2H); 5.00 (s, 2H); 3.95 (m, 4H); 1.55 (s, 9H) ppm.

Step 9.2. 8-Carbamoyl-6-chloro-7-(3-cyanophenyl)-1,2,3,4-dihydropyrrolo[1,2-a]pyrazine hydrochloride

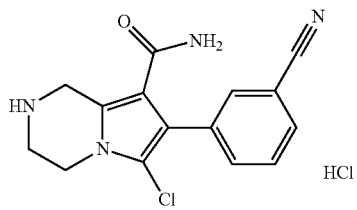 [SMILES: N#Cc1cccc(-c2c(C(N)=O)c3n(c2Cl)CCNC3)c1 ; Cl]

To a solution cooled to about 0° C. of 2.12 g (5.29 mmol) of tert-butyl 8-carbamoyl-6-chloro-7-(3-cyanophenyl)-3,4-dihydropyrrolo[1,2-a]pyrazine-2(1H)-carboxylate in a mixture of 50 ml of dichloromethane and 150 ml of methanol are added portionwise 2.75 g (31.7 mmol) of chlorotrimethylsilane. The mixture is stirred for 18 hours at room temperature and the reaction medium is then concentrated under reduced pressure and co-evaporated twice with ethyl acetate. The residue is isolated after concentration under reduced pressure by filtering off and rinsing with ether, to give 1.78 g of 8-carbamoyl-6-chloro-7-(3-cyanophenyl)-1,2,3,4-dihydropyrrolo-[1,2-a]pyrazine hydrochloride in the form of a white solid.

m.p.: 254-256° C.

$^1$H NMR (DMSO) δ: 9.9 (broad s, 2H); 7.80 (m, 1H); 7.70 (s, 1H); 7.60 (d, 2H); 7.20 (broad s, 1H); 6.5 (broad s, 1H); 4.45 (s, 2H); 4.15 (m, 2H); 3.50 (m, 2H) ppm.

Step 9.3. $N^2$-tert-Butyl-6-chloro-7-(3-cyanophenyl)-3,4-dihydropyrrolo[1,2-a]pyrazine-2,8(1H)-dicarboxamide

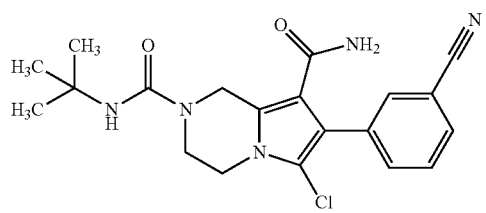 [SMILES: CC(C)(C)NC(=O)N1CCn2c(Cl)c(-c3cccc(C#N)c3)c(C(N)=O)c2C1]

To a solution, under nitrogen and cooled to about 0° C., of 1.11 g (3.29 mmol) of 8-carbamoyl-6-chloro-7-(3-cyanophenyl)-1,2,3,4-dihydropyrrolo[1,2-a]pyrazine hydrochloride and 1.15 ml (8.23 mmol) of triethylamine in 40 ml of dichloromethane is added 0.45 ml (3.95 mmol) of tert-butyl isocyanate. The solution is stirred for 3 hours at room temperature and 30 ml of water are then added. The organic phase is separated out by settling, washed with saturated aqueous 1N hydrochloric acid solution, dried over sodium sulfate and filtered, and concentrated under reduced pressure. The residue is chromatographed on a column of silica gel, eluting with a mixture of 10 to 50% methanol in dichloromethane, and the product obtained is recrystallized from ethyl acetate, to give 0.97 g of $N^2$-tert-butyl-6-chloro-7-(3-cyanophenyl)-3,4-dihydropyrrolo[1,2-a]pyrazine-2,8(1H)-dicarboxamide in the form of a white solid after drying.

m.p.: 192-195° C.

$^1$H NMR (DMSO) δ: 7.80 (d, 1H); 7.45 (s, 1H); 7.65 (m, 2H); 7.1 (broad s, 1H); 6.5 (s, 1H); 6.15 (broad s, 1H); 4.65 (s, 2H); 3.90 (m, 2H); 3.80 (m, 2H); 1.30 (s, 9H) ppm.

Example 10 (Compound 64)

$N^2$-tert-Butyl-6-chloro-7-(4-methoxyphenyl)-3,4-dihydropyrrolo[1,2-a]pyrazine-2,8(1H)-dicarboxamide

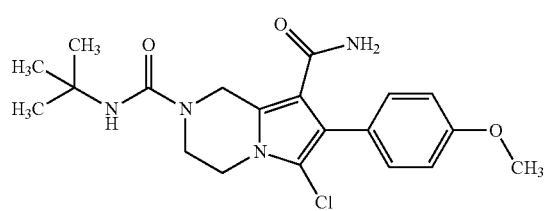 [SMILES: COc1ccc(-c2c(C(N)=O)c3n(c2Cl)CCN(C(=O)NC(C)(C)C)C3)cc1]

Step 10.1. tert-Butyl 8-carbamoyl-6-chloro-7-(4-methoxy-phenyl)-3,4-dihydropyrrolo[1,2-a]pyrazine-2(1H)-carboxylate

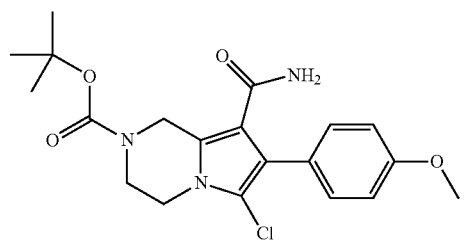 [SMILES: COc1ccc(-c2c(C(N)=O)c3n(c2Cl)CCN(C(=O)OC(C)(C)C)C3)cc1]

To a mixture under nitrogen of 4.00 g (10.6 mmol) of tert-butyl 7-bromo-8-carbamoyl-6-chloro-3,4-dihydropyrrolo[1,2-a]pyrazine-2(1H)-carboxylate under $N_2$ with the bromo derivative of pyrrolo[1,2-a]pyrazine, 1.77 g (11.6 mmol) of 4-methoxyphenylboronic acid and 10.3 g (31.7 mmol) of caesium carbonate in a mixture of 80 ml of tetrahydrofuran and 4 ml of water is added 0.863 g (1.06 mmol) of 1,1'-bis(diphenylphosphino)ferrocenedichloropalladium (II) (CAS 72287-26-4). The mixture is heated at 100° C. for 20 hours and, after cooling, the medium is then diluted with ethyl acetate and filtered through Celite. The filtrate is washed with water, the organic phase is dried over sodium sulfate and concentrated under reduced pressure, and the residue is chromatographed on a column of 40 g of silica gel, eluting with 5 to 100% ethyl acetate in dichloromethane, to give 3.35 g of tert-butyl 8-carbamoyl-6-chloro-7-(4-methoxy-phenyl)-3,4-dihydropyrrolo[1,2-a]pyrazine-2(1H)-carboxylate after crystallization from ethyl acetate and drying.

m.p.: 188.5° C.

$^1$H NMR (CDCl$_3$) δ: 7.35 (d, 2H); 7.05 (d, 2H); 5.3 (broad s, 1H); 5.2 (broad s, 1H); 5.00 (s, 2H); 3.95 (m, 4H); 3.90 (s, 3H); 1.55 (s, 9H) ppm.

Step 10.2. 8-Carbamoyl-6-chloro-7-(4-methoxyphenyl)-1,2,3,4-dihydropyrrolo[1,2-a]pyrazine hydrochloride

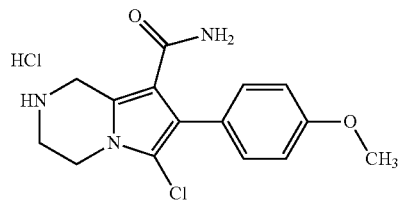 [SMILES: Cl ; COc1ccc(-c2c(C(N)=O)c3n(c2Cl)CCNC3)cc1]

To a solution of 3.35 g (8.25 mmol) of tert-butyl 8 carbamoyl-6-chloro-7-(4-methoxyphenyl)-3,4-dihydropyrrolo-[1,2-a]pyrazine-2(1H)-carboxylate in 100 ml of methanol are added 6.29 ml (5.38 mmol) of chlorotrimethylsilane. After stirring for 19 hours, the solvent is evaporated off under reduced pressure and the evaporation residue is co-evaporated several times with ethyl acetate to give 2.75 g of 8-carbamoyl-6-chloro-7-(4-methoxyphenyl)-1,2,3,4-dihydropyrrolo[1,2-a]pyrazine hydrochloride isolated by filtration, rinsing with ether and drying. The product is used as obtained in the rest of the synthesis.

Step 10.3. $N^2$-tert-Butyl-6-chloro-7-(4-methoxyphenyl)-3,4-dihydropyrrolo[1,2-a]pyrazine-2,8(1H)-dicarboxamide

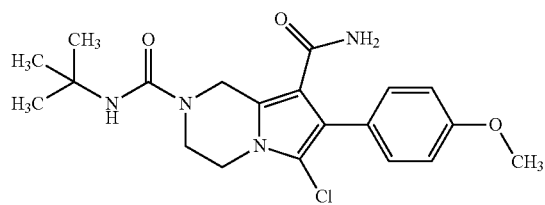 [SMILES: COc1ccc(-c2c(C(N)=O)c3n(c2Cl)CCN(C(=O)NC(C)(C)C)C3)cc1]

To a solution, under nitrogen and at 0° C., of 1.55 g (4.53 mmol) of 8-carbamoyl-6-chloro-7-(4-methoxyphenyl)-1,2,3,4-dihydropyrrolo[1,2-a]pyrazine hydrochloride in 70 ml of dichloromethane are added 1.89 ml (13.7 mmol) of triethylamine and 0.62 ml (5.44 mmol) of tert-butyl isocyanate. The mixture is stirred for three hours while allowing the temperature to return to room temperature, and water and 30 ml of dichloromethane are then added. The organic phase is separated out, washed with water, dried over sodium sulfate and concentrated under reduced pressure. The residue is purified by chromatography on 40 g of silica gel, eluting with a mixture of 20 to 50% ethyl acetate in dichloromethane, to give 0.48 g of $N^2$-tert-butyl-6-chloro-7-(4-methoxyphenyl)-3,4-dihydropyrrolo[1,2-a]pyrazine-2,8(1H)-dicarboxamide in the form of a pale yellow solid after crystallizing from ethyl acetate and drying.

m.p.: 168-170° C.

$^1$H NMR (DMSO-$d_6$) δ: 7.25 (d, 2H); 7.00 (d and broad s, 3H); 6.15 (s, 2H); 5.70 (broad s, 1H); 4.70 (s, 2H); 3.9 (m, 2H); 3.85 (s, 3H); 3.80 (m, 2H); 3.75 (m, 2H); 1.30 (s, 9H) ppm.

Example 11 (Compound 2)

$N^2$-tert-Butyl-7-(4-methoxyphenyl)-3,4-dihydropyrrolo[1,2-a]pyrazine-2,8(1H)-dicarboxamide

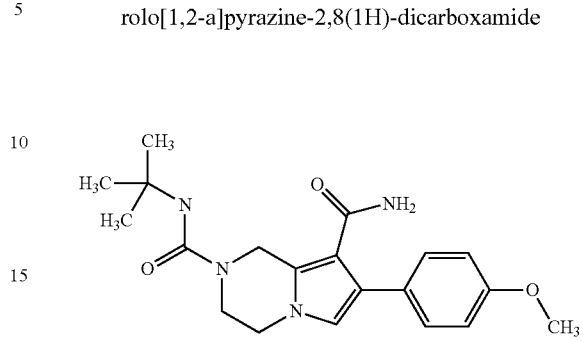

A mixture of 1.20 g (2.96 mmol) of $N^2$-tert-butyl-6-chloro-7-(4-methoxyphenyl)-3,4-dihydropyrrolo[1,2-a]pyrazine-2,8(1H)-dicarboxamide, 6.0 g (95 mmol) of ammonium formate and 0.22 g (0.10 mmol) of 10% palladium-on-charcoal containing 50% water in 80 ml of methanol is refluxed for 6 hours. After cooling, the mixture is filtered through Celite and the Celite is rinsed with methanol and dichloromethane. The filtrate is then concentrated under reduced pressure and the residue is taken up in dichloromethane. The solution is washed with water, dried over sodium sulfate and then concentrated under reduced pressure. The product is then purified by chromatography on a column of 70 g of silica gel, eluting with a mixture of 20 to 50% ethyl acetate in dichloromethane, to give 0.64 g of $N^2$-tert-butyl-7-(4-methoxyphenyl)-3,4-dihydropyrrolo[1,2-a]pyrazine-2,8(1H)-dicarboxamide in the form of a white solid after crystallizing from ethyl acetate and drying.

m.p.: 197-198° C.

$^1$H NMR (DMSO-$d_6$) δ: 7.30 (d, 2H); 6.95 (d, 2H); 6.85 (broad s, 1H); 6.15 (s, 2H); 6.70 (s, 1H); 5.95 (broad s, 1H); 4.70 (s, 2H); 3.95 (m, 2H); 3.80 (s, 3H); 3.70 (m, 2H); 1.30 (s, 9H) ppm.

Example 12 (Compound 36)

$N^2$-tert-Butyl-6-cyclopropyl-7-(4-methoxyphenyl)-3,4-dihydropyrrolo[1,2-a]pyrazine-2,8(1H)-dicarboxamide

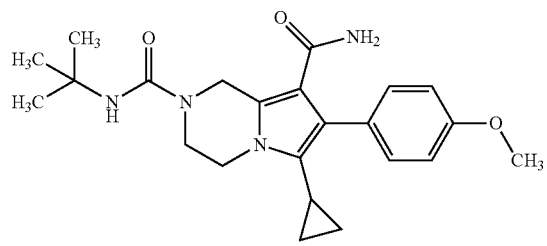 [SMILES: COc1ccc(-c2c(C(N)=O)c3n(c2C2CC2)CCN(C(=O)NC(C)(C)C)C3)cc1]

Step 12.1. 1-tert-Butyl 3-methyl 4-cyclopropanecarbonyl-piperazine-1,3-dicarboxylate

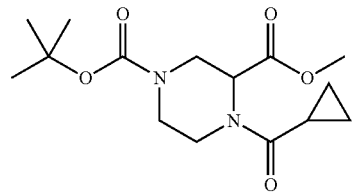 [SMILES: COC(=O)C1CN(C(=O)OC(C)(C)C)CCN1C(=O)C1CC1]

To a solution cooled to 0° C. of 10.0 g (35.6 mmol) of 1-tert-butyl 3-methyl piperazine-1,3-dicarboxylate hydrochloride (CAS 129799-08-2) in 350 ml of dichloromethane are added 11.0 ml (79.1 mmol) of triethylamine and then, over 35 minutes, 3.6 ml (40 mmol) of cyclopropylcarbonyl chloride dissolved in 50 ml of dichloromethane. The medium is stirred from 0° C. to room temperature over 4 hours 30 minutes and is then washed with twice 40 ml of water and dried over sodium sulfate. The solvent is evaporated off under reduced pressure and the residue is chromatographed on a column of 90 g of silica gel, eluting with a mixture of 5 to 50% ethyl acetate in dichloromethane, to give 11.5 g 1-tert-butyl 3-methyl 4-cyclopropanecarbonylpiperazine-1,3-dicarboxylate in the form of a viscous oil.

$^1$H NMR (DMSO-d$_6$—110° C.) δ: 5.6 (m, 1H); 4.95 (broad d, 1H); 4.70 (m, 1H); 4.45 (m, 1H); 4.30 (s, 3H); 4.05 (s, 1H); 3.85 (dd, 1H); 3.60 (broad t, 1H); 2.5 (m, 1H); 2.0 (s, 9H); 1.4 (m, 4H) ppm.

Step 12.2. Sodium 1-tert-Butyl 4-cyclopropanecarbonyl-piperazine-1,3-dicarboxylate

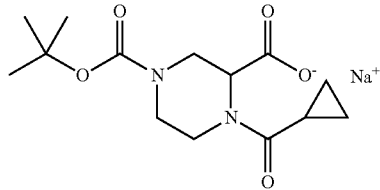 [SMILES: CC(C)(C)OC(=O)N1CCN(C(=O)C2CC2)C(C(=O)[O-])C1 ; [Na+]]

To a solution of 11.5 g (36.8 mmol) of 1-tert-butyl 3-methyl 4-cyclopropanecarbonylpiperazine-1,3-dicarboxylate in 127.5 ml of methanol are added 1.77 g of sodium hydroxide dissolved in 22.5 ml of water. The mixture is stirred for 24 hours and the reaction medium is then concentrated under reduced pressure and the residue co-evaporated with toluene, to give 12.6 g of sodium 1-tert-butyl 4-cyclopropane-carbonylpiperazine-1,3-dicarboxylate in the form of a white powder after drying, and is used as obtained in the rest of the synthesis.

$^1$H NMR (DMSO-d$_6$—110° C.) δ: 4.50 (m, 1H); 4.35 (dd, 1H); 3.95 (m, 1H); 3.70 (m, 1H); 3.35 (broad s, 1H); 3.10 (m, 1H); 2.95 (m, 1H); 1.80 (m, 1H); 1.40 (s, 9H); 0.85-0.55 (m, 4H) ppm.

Step 12.3. tert-Butyl 8-cyano-6-cyclopropyl-3,4-dihydro-1H-pyrrolo[1,2-a]pyrazine-2-carboxylate (CAS 502933-77-9; WO 2003/024 967)

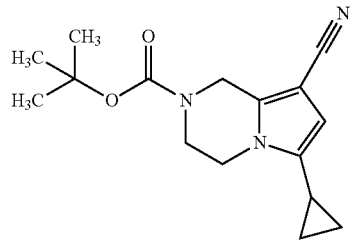 [SMILES: CC(C)(C)OC(=O)N1CCn2c(C3CC3)cc(C#N)c2C1]

To a solution of 57.4 g (179 mmol) of sodium 1-tert-butyl 4-cyclopropanecarbonylpiperazine-1,3-dicarboxylate in 900 ml of dichloromethane are added 35.9 g (188 mmol) of tosyl chloride. After stirring for 20 minutes, 14.3 ml of chloroacrylonitrile (CAS 920-37-6) are added. After a further 20 minutes, 52.7 ml of triethylamine are added, while evolution of gas is observed at the start of the addition. Stirring is continued for 18 hours, and the solution is then washed with water, dried over sodium sulfate and concentrated under reduced pressure. The residue is chromatographed on a column of 330 g of silica gel, eluting with a mixture of 80 to 0% cyclohexane, 20 to 95% dichloromethane and 0 to 5% ethyl acetate, to give 10 g of an oil predominantly containing tert-butyl 8-cyano-6-cyclo-propyl-3,4-dihydro-1H-pyrrolo[1,2-a]pyrazine-2-carboxylate (CAS 502933-77-9; WO 2003/024 967) and in minor amount tert-butyl 7-cyano-6-cyclopropyl-3,4-dihydro-1H-pyrrolo[1,2-a]pyrazine-2-carboxylate.

$^1$H NMR (CDCl$_3$) δ: 6.00 and 5.95 (s and s, 1H); 4.65 and 4.45 (s and s, 2H); 3.95 and 3.80 (m and m, 4H); 1.6 (m, 1H); 1.4 (s, 9H); 1.1-0.75 (m, 3H); 0.55 (m, 1H) ppm.

Step 12.4. tert-Butyl 8-carbamoyl-6-cyclopropyl-3,4-dihydro-1H-pyrrolo[1,2-a]pyrazine-2-carboxylate

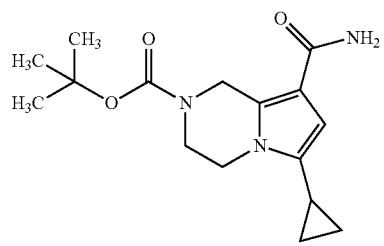 [SMILES: CC(C)(C)OC(=O)N1CCn2c(C3CC3)cc(C(N)=O)c2C1]

To a solution of 9.8 g (34.1 mmol) of tert-butyl 8-cyano-6-cyclopropyl-3,4-dihydro-1H-pyrrolo[1,2-a]pyrazine-2-carboxylate (CAS 502933-77-9; WO 2003/024 967) and tert-butyl 7-cyano-6-cyclopropyl-3,4-dihydro-1H-pyrrolo[1,2-a]pyrazine-2-carboxylate (502933-78-0; WO 2003/024 967) obtained during step 12.3. in 200 ml of methanol are added 8.6 ml (290 mmol) of aqueous 35 wt % sodium hydroxide and 8.0 ml (93 mmol) of 35% aqueous hydrogen peroxide solution four times every 2 hours, while the mixture is maintained at 45° C. After 18 hours at this same temperature, the mixture is cooled and treated with 10.7 g (68 mmol) of sodium thiosulfate and 50 ml of water and then stirred for 1 hour. The solvent is partially concentrated and the reaction product is extracted with ethyl acetate. The organic phases are dried over sodium sulfate and concentrated under reduced pressure, and the residue is chromatographed on a column of 80 g of silica gel, eluting with a mixture of 5 to 50% ethyl acetate in dichloromethane, to give 2.82 g of tert-butyl 7-carbamoyl-6-cyclopropyl-3,4-dihydro-1H-pyrrolo[1,2-a]pyrazine-2-carboxylate and 4.82 g of tert-butyl 8-carbamoyl-6-cyclopropyl-3,4-dihydro-1H-pyrrolo[1,2-a]pyrazine-2-carboxylate after crystallizing from ethyl acetate and drying.

¹H NMR (CDCl₃) δ: 5.95 (s, 1H); 5.45 (broad s, 2H); 4.95 (s, 2H); 4.05 (m, 2H); 3.90 (m, 2H); 1.7 (m, 1H); 1.50 (s, 9H); 0.90 (m, 2H); 0.60 (m, 2H) ppm.

Step 12.5. tert-Butyl 7-bromo-8-carbamoyl-6-cyclopropyl-3,4-dihydro-1H-pyrrolo[1,2-a]pyrazine-2-carboxylate

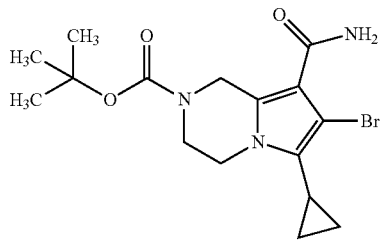

To a solution of 12.8 g (41.9 mmol) of tert-butyl 8-cyano-6-cyclopropyl-3,4-dihydro-1H-pyrrolo[1,2-a]pyrazine-2-carboxylate (CAS 502933-77-9; WO 2003/024 967) in 350 ml of dichloromethane cooled to between –30 and –35° C. are added portionwise 8.36 g (47.0 mmol) of N-bromosuccinimide (CAS 128-08-5). After stirring for 1 hour at this same temperature, water is added and the mixture is stirred until it has returned to room temperature. The organic phase is separated out and the solvent is evaporated off under reduced pressure. The solid residue is triturated in water, isolated by filtration, rinsed with water and dried in air. The solid is then purified by chromatography on a column of silica gel, eluting with a mixture of 10 to 50% ethyl acetate in dichloromethane, to give 11.8 g of tert-butyl 7-bromo-8-carbamoyl-6-cyclopropyl-3,4-dihydro-1H-pyrrolo[1,2-a]pyrazine-2-carboxylate in the form of a white solid after crystallizing from a minimum amount of ethyl acetate, rinsing with diethyl ether and drying.

m.p.: 162.1° C.

¹H NMR (CDCl₃) δ: 6.85 (broad s, 1H); 5.40 (broad s, 1H); 5.00 (s, 2H); 4.05 (m, 2H); 3.90 (m, 2H); 1.55 (m and s, 10H); 1.10 (m, 2H); 0.85 (m, 2H) ppm.

Step 12.6. tert-Butyl 8-carbamoyl-6-cyclopropyl-7-(4-methoxyphenyl)-3,4-dihydro-1H-pyrrolo[1,2-a]pyrazine-2-carboxylate

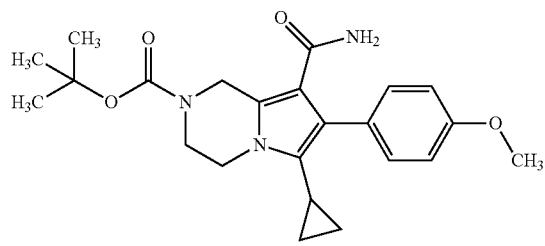

To a mixture of 3.00 g (7.81 mmol) of tert-butyl 7-bromo-8-cyano-6-cyclopropyl-3,4-dihydro-1H-pyrrolo[1,2-a]pyrazine-2-carboxylate, 1.54 g (10.2 mmol) of 4-methoxyphenylboronic acid (CAS 5720-07-0) and 7.63 g (23.4 mmol) of caesium carbonate in a mixture of 80 ml of tetrahydrofuran and 4 ml of water under argon is added 0.64 g (0.78 mmol) of 1,1'-bis(diphenylphosphino)ferrocenedichloropalladium (II) (CAS 72287-26-4), and the mixture is heated at 100° C. for 20 hours. After cooling, the mixture is diluted with ethyl acetate and filtered through Celite, the organic phase is washed with water, dried over sodium sulfate and filtered, and the solution is concentrated under reduced pressure. The residue is chromatographed on a column of 40 g of silica gel, eluting with a mixture of 20 to 50% ethyl acetate in dichloromethane, to give 1.51 g of tert-butyl 8-carbamoyl-6-cyclopropyl-7-(4-methoxyphenyl)-3,4-dihydro-1H-pyrrolo[1,2-a]pyrazine-2-carboxylate in the form of a white solid after crystallizing from a minimum amount of ethyl acetate, rinsing with diethyl ether and drying.

m.p.: 181-182° C.

¹H NMR (DMSO-d₆) δ: 7.20 (d, 1H); 7.00 (d, 2H); 6.75 (broad s, 1H); 5.25 (broad s, 1H); 4.80 (s, 2H); 4.00 (m, 2H); 3.80 (m and s, 5H); 1.65 (m, 1H); 1.5 (s, 9H); 0.60 (m, 2H); 0.15 (m, 2H) ppm.

Step 12.7. 8-Carbamoyl-6-cyclopropyl-7-(4-methoxy-phenyl)-1,2,3,4-dihydropyrrolo[1,2-a]pyrazine hydrochloride

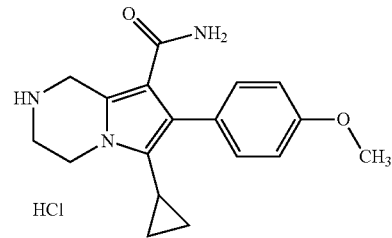 [SMILES: COc1ccc(-c2c(C(N)=O)c3n(c2C2CC2)CCNC3)cc1 ; Cl]

To a solution of 1.47 g (3.57 mmol) of tert-butyl 8-cyano-6-cyclopropyl-7-(4-methoxyphenyl)-3,4-dihydro-1H-pyrrolo[1,2-a]pyrazine-2-carboxylate in 60 ml of methanol are added 2.7 ml (21 mmol) of trimethylsilyl chloride. After stirring for 20 hours, the solvent is evaporated off under reduced pressure and the residue is co-evaporated several times with ethyl acetate, to give 1.1 g of 8-carbamoyl-6-cyclo-propyl-7-(4-methoxyphenyl)-1,2,3,4-dihydropyrrolo[1,2-a]pyrazine hydrochloride in the form of a white solid after crystallizing from a minimum amount of ethyl acetate and drying. It is then used as obtained in the rest of the synthesis.

m.p.: 267-271° C.

¹H NMR (DMSO-d₆) δ: 9.9 (broad s, 2H); 7.10 (d, 1H); 6.90 (d, 2H); 6.80 (broad s, 1H); 5.15 (broad s, 1H); 4.35 (s, 2H); 4.10 (m, 2H); 3.80 (s, 3H); 3.50 (m, 2H); 1.55 (m, 1H); 0.55 (m, 2H); 0.00 (m, 2H) ppm.

Step 12.8. N²-tert-Butyl-6-cyclopropyl-7-(4-methoxy-phenyl)-3,4-dihydropyrrolo[1,2-a]pyrazine-2,8(1H)-dicarboxamide

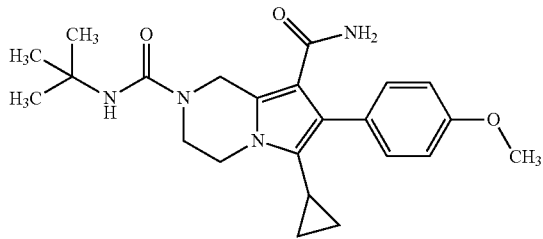 [SMILES: COc1ccc(-c2c(C(N)=O)c3n(c2C2CC2)CCN(C(=O)NC(C)(C)C)C3)cc1]

To a solution of 0.25 g (0.72 mmol) of 8-carbamoyl-6-cyclo-propyl-7-(4-methoxyphenyl)-1,2,3,4-dihydropyrrolo[1,2-a]pyrazine hydrochloride in 30 ml of dichloromethane is added 0.25 ml (1.8 mmol) of triethylamine and then, at 0° C., 0.10 ml (0.86 mmol) of tert-butyl isocyanate. After stirring for 3 hours at 0° C., dichloromethane and water are added and the organic phase is then separated out, washed with water, dried over sodium sulfate and concentrated under reduced pressure. The residue is chromatographed on a column of 12 g of silica gel, eluting with a mixture of 20 to 50% ethyl acetate in dichloromethane, to give 0.22 g of N²-tert-butyl-6-cyclopropyl-7-(4-methoxyphenyl)-3,4-dihydropyrrolo-[1,2-a]pyrazine-2,8(1H)-dicarboxamide in the form of a white solid after crystallization from a minimum amount of ethyl acetate, rinsing with diethyl ether and drying.

m.p.: 177-179° C.

¹H NMR (DMSO-d₆) δ: 7.10 (d, 2H); 6.90 (d, 2H); 6.60 (broad s, 1H); 5.95 (s, 1H); 5.20 (broad s, 1H); 4.60 (s, 2H); 3.85 (m, 2H); 3.70 (s, 3H); 3.65 (m, 2H); 1.55 (m, 1H); 1.20 (s, 9H); 0.55 (m, 2H); 0.05 (m, 2H) ppm.

Example 13 (Compound 36)

N²-tert-Butyl-6-cyclopropyl-7-(4-methoxyphenyl)-3,4-dihydropyrrolo[1,2-a]pyrazine-2,8(1H)-dicarboxamide

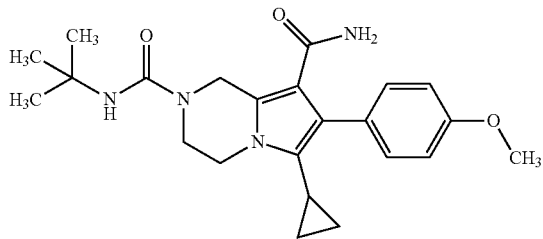 [SMILES: COc1ccc(-c2c(C(N)=O)c3n(c2C2CC2)CCN(C(=O)NC(C)(C)C)C3)cc1]

The synthesis of this compound has already been described in Example 12 via an alternative procedure.

Step 13.1. 8-Carboxamide-7-bromo-6-cyclopropyl-3,4-dihydropyrrolo[1,2-a]pyrazine hydrochloride

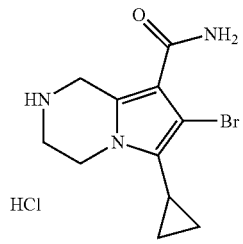

To a solution under nitrogen of 6.34 g (16.5 mmol) of tert-butyl 7-bromo-8-carbamoyl-6-cyclopropyl-3,4-dihydro-1H-pyrrolo[1,2-a]pyrazine-2-carboxylate in 120 ml of methanol are added 10.5 ml of trimethylsilyl chloride. After reaction for 18 hours, the medium is concentrated under reduced pressure, the residue is taken up in toluene and the solvent is evaporated off under reduced pressure. 5.4 g of 8-carboxamide-7-bromo-6-cyclopropyl-3,4-dihydropyrrolo[1,2-a]pyrazine hydrochloride are thus obtained in the form of a yellow powder.

m.p.: 240-241° C.

¹H NMR (DMSO-d₆) δ: 9.8 (broad s, 2H); 7.35 (broad s, 1H); 6.75 (broad s, 1H); 4.45 (s, 2H); 4.20 (m, 2H); 3.55 (m, 2H); 1.65 (m, 1H); 1.00 (m, 2H); 0.70 (m, 2H) ppm.

Step 13.2. N²-tert-Butyl-7-bromo-6-cyclopropyl-3,4-dihydropyrrolo[1,2-a]pyrazine-2,8(1H)-dicarboxamide

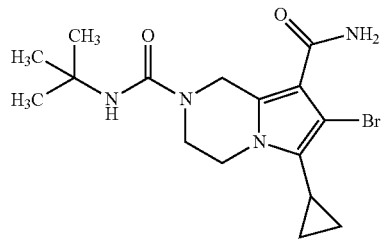 [SMILES: CC(C)(C)NC(=O)N1CCn2c(c(C(N)=O)c(Br)c2C2CC2)C1]

To a mixture of 5.2 g (16.5 mmol) of 8-carboxamide-7-bromo-6-cyclopropyl-3,4-dihydropyrrolo[1,2-a]pyrazine hydrochloride and 6.90 ml (49.5 ml) of triethylamine in 200 ml of dichloromethane at 0° C. are added 2.1 ml (18 mmol) of tert-butyl isocyanate. After stirring for 2 hours, 50 ml of water are added and the product is extracted with dichloromethane. The organic phase is separated out, washed with water, dried over sodium sulfate and concentrated under reduced pressure. The residue is chromatographed on a column of 70 g of silica gel, eluting with a mixture of 5 to 50% ethyl acetate in dichloromethane, to give 4.5 g of N²-tert-butyl-7-bromo-6-cyclopropyl-3,4-dihydropyrrolo[1,2-a]pyrazine-2,8(1H)-dicarboxamide in the form of a white solid after crystallizing from a minimum amount of ethyl acetate, rinsing with diethyl ether and drying.

m.p.: 204-208° C.

¹H NMR (DMSO-d₆) δ: 6.95 (broad s, 1H); 6.45 (broad s, 1H); 5.85 (s, 1H); 4.45 (s, 2H); 3.75 (m, 2H); 3.45 (m, 2H); 1.40 (m, 1H); 1.15 (s, 9H); 0.75 (m, 2H); 0.50 (m, 2H) ppm.

Step 13.3. N²-tert-Butyl-6-cyclopropyl-7-(4-methoxy-phenyl)-3,4-dihydropyrrolo[1,2-a]pyrazine-2,8(1H)-dicarboxamide

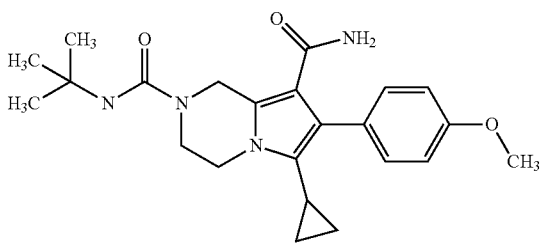 [SMILES: COc1ccc(-c2c(C(N)=O)c3n(c2C2CC2)CCN(C(=O)NC(C)(C)C)C3)cc1]

To a mixture under nitrogen of 0.750 g (1.96 mmol) of N²-tert-butyl-7-bromo-6-cyclopropyl-3,4-dihydropyrrolo[1, 2-a]pyrazine-2,8(1H)-dicarboxamide, 0.446 g (2.94 mmol) of 4-methoxyphenylboronic acid (CAS 5720-07-0) and 5.8 ml (12 mmol) of aqueous 2M caesium carbonate solution in a mixture of 15 ml of toluene and 15 ml of ethanol under argon is added 0.64 g (0.78 mmol) of tetrakis(triphenyl-phosphine) palladium (CAS 14221-01-3), and the mixture is heated at 100° C. for 17 hours. After cooling, the mixture is filtered through Celite and the filtrate concentrated under reduced pressure. The residue is then taken up in dichloromethane, the organic phase is washed with water, dried over sodium sulfate and filtered, and the solution is concentrated under reduced pressure. The residue is chromatographed on a column of 15 g of silica gel, eluting with a mixture of 10 to 100% ethyl acetate in dichloromethane, to give 0.19 g of $N^2$-tert-butyl-6-cyclo-propyl-7-(4-methoxyphenyl)-3,4-dihydropyrrolo[1,2-a]pyrazine-2,8(1H)-dicarboxamide in the form of a white solid after crystallizing from a minimum amount of ethyl acetate, rinsing with diethyl ether and drying, and is identical to the compound obtained according to the procedure of Example 12.

Example 14 (Compound 16)

$N^2$-tert-Butyl-6-cyclopropyl-7-(3-trifluoromethylphenyl)-3,4-dihydropyrrolo[1,2-a]pyrazine-2,8(1H)-dicarboxamide

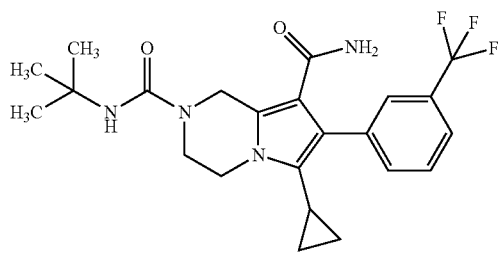 [SMILES: CC(C)(C)NC(=O)N1CCn2c(c(C(N)=O)c(-c3cccc(C(F)(F)F)c3)c2C2CC2)C1]

To a mixture of 57.0 mg (0.300 mmol) of (3-trifluoromethylphenyl)boronic acid and 76.7 mg (0.200 mmol) of $N^2$-tert-butyl-7-bromo-6-cyclopropyl-3,4-dihydropyrrolo-[1,2-a]pyrazine-2,8(1H)-dicarboxamide in a reaction tube are added 2 ml of tetrahydrofuran degassed beforehand under argon for 15 minutes and 63.6 mg (0.60 mmol) of disodium carbonate dissolved in 1 ml of water. The tube is then purged with argon, and about 16 mg (0.02 mmol) of a complex of 1,1'-bis(diphenylphosphino)ferrocenedichloropalladium (II) and dichloromethane ($PdCl_2(dppf).CH_2Cl_2$—CAS 95464-05-4) suspended in 2 ml of tetrahydrofuran degassed beforehand under argon are added. The tube is then stirred at 70° C. for 20 hours, the mixture is cooled and the solvent is evaporated off under reduced pressure. The residue is taken up in 5 ml of tetrahydrofuran and 100 mg of propanethiol-grafted silica (Si-Thiol, Biotage) are added. The mixture is stirred for 4 hours at room temperature and the grafted silica is separated out by filtration on a Celite cartridge, the Celite is washed twice with 1 ml of tetrahydrofuran and the filtrate is concentrated under reduced pressure. The residue is then purified by SFC purification, to give 0.017 g of $N^2$-tert-butyl-6-cyclopropyl-7-(3-trifluoromethyl-phenyl)-3,4-dihydropyrrolo[1,2-a]pyrazine-2,8(1H)-dicarboxamide.

$^1$H NMR (DMSO-$d_6$) δ: 7.60 (d, 3H); 6.90 (broad s, 1H); 6.20 (broad s, 1H); 6.10 (s, 1H); 4.65 (s, 2H); 3.95 (m, 2H); 3.70 (m, 2H); 1.80 (m, 1H); 1.30 (s, 9H); 0.7 (m, 2H); 0.00 (m, 2H) ppm.

Example 15 (Compound 83)

trans-6-Chloro-7-(3-fluorophenyl)-$N^2$-(4-hydroxycyclohexyl)-3,4-dihydropyrrolo[1,2-a]pyrazine-2,8 (1H)-dicarboxamide

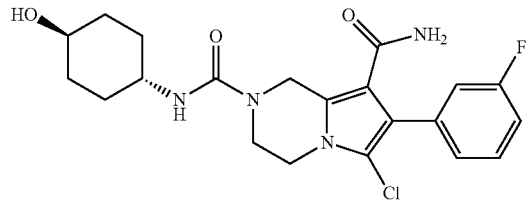 [SMILES: NC(=O)c1c(-c2cccc(F)c2)c(Cl)n2c1CN(C(=O)N[C@H]1CC[C@H](O)CC1)CC2]

To a solution of 0.480 g (4.17 mmol) of trans-4-aminocyclohexanol (CAS 27489-62-9) in 10 ml of dichloromethane is added 0.84 g (4.17 mmol) of 4-nitrophenyl chloroformate (CAS 7693-46-1), followed by addition of 1.36 g (2.52 mmol) of diisopropylethylamine. After 1 hour at room temperature, the solvent is stripped off by evaporation under reduced pressure and the residue is suspended in 21 ml of ethyl acetate. 1.00 g (3.42 mmol) of 6-chloro-7-(3-fluorophenyl)-1,2,3,4-tetrahydropyrrolo[1,2-a]pyrazine-8-carboxamide and 0.90 g (0.70 mmol) of diisopropylethylamine are then added and the mixture is stirred for 30 minutes at reflux, to give a homogeneous solution. After cooling, the solvent is stripped off by evaporation under reduced pressure, the residue is then taken up in ethyl acetate and the solution is washed with aqueous sodium hydrogen carbonate solution and then with saturated aqueous sodium chloride solution. The organic phase is dried over sodium sulfate and then concentrated under reduced pressure. The residue is purified by two successive chromatographies on a column of silica gel, eluting with a mixture of 2 to 10% methanol in dichloromethane, to give 0.37 g of trans-6-chloro-7-(3-fluoro-phenyl)-$N^2$-(4-hydroxycyclohexyl)-3,4-dihydropyrrolo[1,2-a]pyrazine-2,8 (1H)-dicarboxamide in the form of a solid after recrystallizing from a mixture of methanol and diisopropyl ether and drying.

m.p.: 251-253° C.

$^1$H NMR (DMSO-$d_6$) δ: 7.45 (m, 1H); 7.15 (m, 3H); 7.05 (bs, 1H); 6.50 (d, 1H); 6.2 (broad s, 1H); 4.80 (s, 2H); 4.45 (d, 1H); 3.85 (m, 2H); 3.80 (m, 2H); 3.5 (m, 2H); 1.8 (m, 4H); 1.2 (m, 4H) ppm.

Example 16 (Compound 104)

6-Bromo-$N^2$-tert-butyl-7-(3-fluorophenyl)-3,4-dihydropyrrolo[1,2-a]pyrazine-2,8(1H)-dicarboxamide

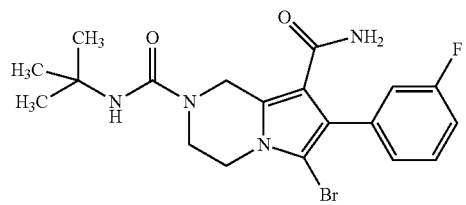 [SMILES: CC(C)(C)NC(=O)N1CCn2c(Br)c(-c3cccc(F)c3)c(C(N)=O)c2C1]

Step 16.1. Ethyl 4-(3-fluorophenyl)-1H-pyrrole-3-carboxylate

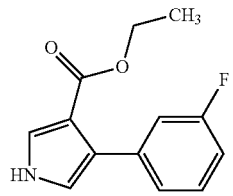 [SMILES: CCOC(=O)c1c[nH]cc1-c1cccc(F)c1]

To a suspension of 38.3 g (341 mmol) of potassium tert-butoxide at 60% in oil in 500 ml of anhydrous tetrahydrofuran is added dropwise a mixture of 55.2 g (284 mmol) of ethyl (E)-3-(3-fluorophenyl)acrylate (CAS 166250-00-6) and 55.5 g (284 mmol) of tosylmethyl isocyanide (CAS 36635-61-7) dissolved in 500 ml of tetrahydrofuran, while maintaining the temperature of the reaction medium at about 25° C. The mixture is then stirred for 1 hour 30 minutes at room temperature. The mixture is then poured into saturated aqueous solution and the reaction product is extracted with ethyl acetate. The organic phase is dried over sodium sulfate and the solvent is evaporated off under reduced pressure, to give a brown solid, which is chromatographed on a column of silica gel, eluting with dichloromethane, to give 40.7 g of ethyl 4-(3-fluorophenyl)-1H-pyrrole-3-carboxylate, in the form of a white powder after triturating in diisopropyl ether, filtering off and drying.

m.p.: 120-122° C.

$^1$H NMR (CDCl$_3$) δ: 8.55 (broad s, 1H); 7.50 (d, 1H); 7.3 (m, 3H); 7.00 (m, 1H); 6.80 (d, 1H); 4.25 (q, 2H); 1.30 (t, 3H) ppm.

Step 16.2. Ethyl 5-bromo-4-(3-fluorophenyl)-1H-pyrrole-3-carboxylate

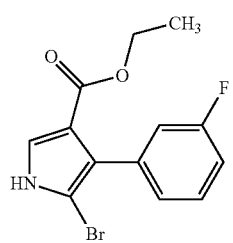 [SMILES: CCOC(=O)c1c[nH]c(Br)c1-c1cccc(F)c1]

To a solution of 38.3 g (164 mmol) of ethyl 4-(3-fluorophenyl)-1H-pyrrole-3-carboxylate in 380 ml of tetrahydrofuran are added, over 30 minutes, 32.1 g (181 mmol) of N-bromosuccinimide (CAS 128-08-5), and the mixture is then stirred for 3 hours at reflux. After cooling, 200 ml of aqueous 5% sodium thiosulfate solution are added and the reaction product is extracted with ethyl acetate. The organic phase is dried over sodium sulfate and the solvent is evaporated off under reduced pressure, to give 17.1 g of ethyl 5-bromo-4-(3-fluorophenyl)-1H-pyrrole-3-carboxylate in the form of a white powder after recrystallizing from diisopropyl ether, filtering off and drying.

m.p.: 114-117° C.

$^1$H NMR (CDCl$_3$) δ: 8.55 (broad s, 1H); 7.50 (s, 1H); 7.35 (m, 1H); 7.20 (m, 1H); 7.05 (m, 1H); 4.20 (q, 2H); 1.20 (t, 3H) ppm.

Step 16.3. Ethyl 1-(2-tert-butoxycarbonylaminoethyl)-5-bromo-4-(3-fluorophenyl)-1H-pyrrole-3-carboxylate

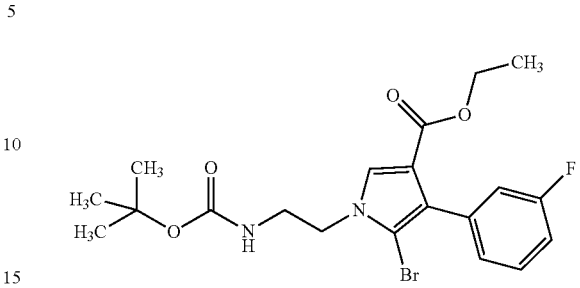

To a solution of 39.6 g (127 mmol) of ethyl 5-bromo-4-(3-fluorophenyl)-1H-pyrrole-3-carboxylate in 275 ml of acetonitrile are added 10.1 g (253 mmol) of powdered sodium hydroxide and 1.7 g (5.1 mmol) of tetrabutylammonium hydrogen sulfate, and the mixture is stirred vigorously for a few minutes, followed by adding 34.1 g (152 mmol) of tert-butyl(2-bromoethyl)carbamate (CAS 39684-80-5), and the mixture is then stirred for 17 hours at reflux. After cooling, the solvent is evaporated off under reduced pressure and the residue is taken up in ethyl acetate. The solution is washed with saturated aqueous sodium chloride solution, the organic phase is then dried over sodium sulfate and the solvent is evaporated off under reduced pressure, to give a brown oil, which is crystallized from diisopropyl ether, to give 43 g of ethyl 1-(2-tert-butoxycarbonylaminoethyl)-5-bromo-4-(3-fluorophenyl)-1H-pyrrole-3-carboxylate in the form of a beige-coloured powder after filtering off and drying.

m.p.: 108-110° C.

$^1$H NMR (CDCl$_3$) δ: 7.50 (s, 1H); 7.35 (m, 1H); 7.15 (m, 1H); 7.10 (m, 1H); 7.05 (m, 1H); 4.70 (broad s, 2H); 4.15 (m, 4H); 3.50 (m, 2H); 1.50 (s, 9H); 1.2 (t, 3H) ppm.

Step 16.4. Ethyl 6-chloro-7-(3-fluorophenyl)-1,2,3,4-tetrahydropyrrolo[1,2-a]pyrazine-8-carboxylate

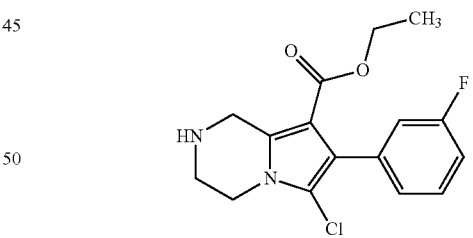

To a solution of 38.4 g (84.3 mmol) of ethyl 1-(2-tert-butoxycarbonylaminoethyl)-5-bromo-4-(3-fluorophenyl)-1H-pyrrole-3-carboxylate in 80 ml of ethanol are added slowly 271 ml (949 mmol) of aqueous 3.5N hydrochloric acid solution. The formation of a white precipitate is rapidly observed and then, after 45 minutes, the medium becomes clear, while the mixture is heated to 70° C., and 3.00 g (31.2 mmol) of paraformaldehyde are added. Heating is continued at 70° C. for 1 hour. After cooling, the reaction medium is poured into a mixture of ice and aqueous 4N sodium hydroxide solution. The product is extracted with dichloromethane, the organic phase is dried over sodium sulfate and the solvent is evaporated off under reduced pressure, to give a brown oil, which is chromatographed on a column of 330 g of silica gel, eluting with a mixture of 3% methanol in dichloromethane, to give 14.3 g of ethyl 6-chloro-7-(3-fluorophenyl)-1,2,3,4-tetrahydropyrrolo[1,2-a]pyrazine-8-carboxylate after crystallizing from 50 ml of diisopropyl ether.

m.p.: 96-98° C.

$^1$H NMR (DMSO-d$_6$) δ: 7.40 (m, 1H); 7.1 (m, 3H); 4.10 (s, 2H); 4.05 (q, 2H); 3.80 (t, 2H); 3.15 (t, 2H); 2.8 (broad s, 1H); 1.1 (t, 3H) ppm.

Step 16.5. 2-tert-Butyl 8-ethyl 6-chloro-7-(3-fluorophenyl)-3,4-dihydropyrrolo[1,2-a]pyrazine-2,8(1H)-dicarboxylate

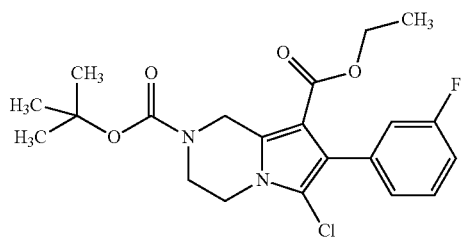 [SMILES: CCOC(=O)c1c(-c2cccc(F)c2)c(Cl)n2c1CN(C(=O)OC(C)(C)C)CC2]

To a solution of 12.7 g (34.7 mmol) of ethyl 6-chloro-7-(3-fluorophenyl)-1,2,3,4-tetrahydropyrrolo[1,2-a]pyrazine-8-carboxylate in 150 ml of dichloromethane are added slowly 7.95 g (36.4 mmol) of di-tert-butyl dicarbonate (CAS 24424-99-5) dissolved in dichloromethane. After stirring for 30 minutes at room temperature, the solvent is evaporated off under reduced pressure, to give an orange-coloured oil, which is purified by chromatography on a column of 220 g of silica gel, eluting with a mixture of 15% ethyl acetate in cyclohexane, to give 17.0 g of 2-tert-butyl 8-ethyl 6-chloro-7-(3-fluorophenyl)-3,4-dihydropyrrolo[1,2-a]pyrazine-2,8(1H)-dicarboxylate in the form of a pale yellow oil, which is crystallized from 60 ml of hexane, to give 14.2 g of a beige-coloured powder.

m.p.: 84-86° C.

$^1$H NMR (DMSO-d$_6$) δ: 7.45 (m, 1H); 7.15 (m, 3H); 4.80 (s, 2H); 4.05 (q, 2H); 3.95 (m, 2H); 3.80 (m, 2H); 1.50 (s, 9H); 1.10 (t, 3H) ppm.

Step 16.6. 2-tert-Butyl 8-ethyl 7-(3-fluorophenyl)-3,4-dihydropyrrolo[1,2-a]pyrazine-2,8(1H)-dicarboxylate

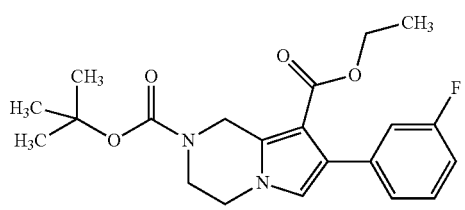 [SMILES: CCOC(=O)c1c(-c2cccc(F)c2)cn2c1CN(C(=O)OC(C)(C)C)CC2]

A mixture of 6.00 g (14.2 mmol) of 2-tert-butyl 8-ethyl 6-chloro-7-(3-fluorophenyl)-3,4-dihydropyrrolo[1,2-a]pyrazine-2,8(1H)-dicarboxylate, 13.4 g (212 mmol) of ammonium formate (CAS 540-69-2) and 0.6 g of 10% palladium-on-charcoal containing 50% water in 50 ml of methanol is stirred at reflux for 45 minutes. After cooling, the mixture is filtered through a Buchner funnel and the filtrate is concentrated under reduced pressure. The residue is taken up in ethyl acetate, the solution is washed with aqueous 2N sodium hydroxide solution and then dried over sodium sulfate, and the solvent is evaporated off under reduced pressure, to give 5.5 g of 2-tert-butyl 8-ethyl 7-(3-fluorophenyl)-3,4-dihydropyrrolo[1,2-a]pyrazine-2,8(1H)-dicarboxylate in the form of a yellow oil.

$^1$H NMR (DMSO-d$_6$) δ: 7.35 (m, 1H); 7.20 (m, 2H); 7.05 (m, 1H); 7.00 (s, 1H); 4.80 (s, 2H); 4.05 (q, 2H); 4.00 (m, 2H); 3.85 (m, 2H); 1.45 (s, 9H); 1.20 (t, 3H) ppm.

Step 16.7. 2-tert-Butyl 8-ethyl 6-bromo-7-(3-fluorophenyl)-3,4-dihydropyrrolo[1,2-a]pyrazine-2,8(1H)-dicarboxylate

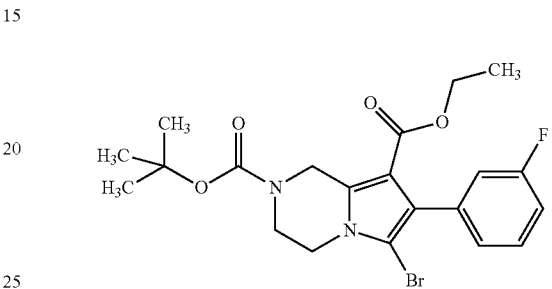

To a solution of 2.00 g (5.15 mmol) of tert-butyl-8-ethyl 7-(3-fluorophenyl)-1,2,3,4-tetrahydropyrrolo[1,2-a]pyrazine-2,8-dicarboxylate in 12 ml of tetrahydrofuran are added portionwise 1.01 g (5.66 mmol) of N-bromosuccinimide (CAS 128-08-5) over 30 minutes. After stirring for 1 hour at room temperature, the mixture is poured into water and the product is extracted with ethyl acetate. The solution is dried over sodium sulfate and the solvent is evaporated off under reduced pressure, to give 2.4 g of 2-tert-butyl 8-ethyl 6-bromo-7-(3-fluorophenyl)-3,4-dihydropyrrolo[1,2-a]pyrazine-2,8(1H)-dicarboxylate in the form of a yellow oil.

$^1$H NMR (DMSO-d$_6$) δ: 7.50 (m, 1H); 7.15 (m, 1H); 7.05 (m, 2H); 4.80 (s, 2H); 4.05 (m, 2H); 3.95 (m, 2H); 3.80 (m, 2H); 1.45 (s, 9H); 1.05 (t, 3H) ppm.

Step 16.9. 2-(tert-Butoxycarbonyl)-6-bromo-7-(3-fluoro-phenyl)-1,2,3,4-tetrahydropyrrolo[1,2-a]pyrazine-8-carboxylic acid

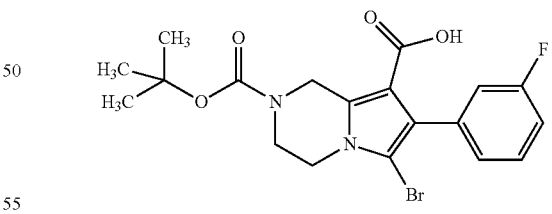

To a suspension of 2.41 g (5.16 mmol) of 2-tert-butyl 8-ethyl 6-bromo-7-(3-fluorophenyl)-3,4-dihydropyrrolo[1,2-a]pyrazine-2,8(1H)-dicarboxylate in 18 ml of ethanol are added 10.3 ml (10.3 mmol) of 1N sodium hydroxide solution and the mixture is heated at 70° C. for 2 days. The mixture is then taken up in dichloromethane and acidified by addition of 25 ml of aqueous 1N sulfuric acid. The organic phase is separated out and dried over sodium sulfate, and the solvent is evaporated off under reduced pressure, to give a yellow solid, which is purified by chromatography on a column of 40 g of silica gel, eluting with a mixture of 4% methanol in dichloromethane, to give 1.65 g of 2-(tert-butyloxy-carbonyl)-6-bromo-7-(3-fluorophenyl)-1,2,3,4-tetrahydropyrrolo[1,2-a]pyrazine-8-carboxylic acid in the form of a pale yellow powder.

m.p.: 199-201° C.

$^1$H NMR (DMSO-d$_6$) δ: 12.0 (broad s, 1H); 7.4 (m, 1H) 7.1 (m, 3H); 4.80 (s, 2H); 3.95 (m, 2H); 3.80 (m, 2H); 1.45 (s, 9H) ppm.

Step 16.10. tert-Butyl 6-bromo-7-(3-fluorophenyl)-8-(1H-imidazol-1-ylcarbonyl)-3,4-dihydropyrrolo[1,2-a]pyrazine-2(1H)-carboxylate

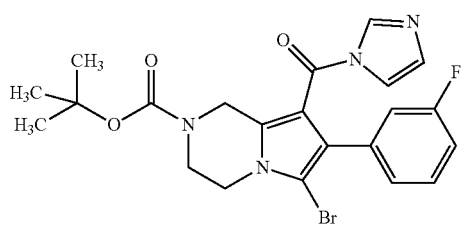 [SMILES: CC(C)(C)OC(=O)N1CCn2c(Br)c(-c3cccc(F)c3)c(C(=O)n3ccnc3)c2C1]

To a solution of 1.87 g (4.27 mmol) of 2-(tert-butyloxycarbonyl)-6-bromo-7-(3-fluorophenyl)-1,2,3,4-tetrahydropyrrolo[1,2-a]pyrazine-8-carboxylic acid in 10 ml of tetrahydrofuran is added 0.831 g (5.12 mmol) of carbonyldiimidazole (CAS 530-62-1). After reaction for 1 hour at 50° C., the mixture is cooled and taken up in water, and the product is extracted with ethyl acetate. The organic phase is dried over sodium sulfate and the solvent is evaporated off under reduced pressure, to give a yellow oil, which crystallizes from 25 ml of diisopropyl ether, to give 1.82 g tert-butyl 6-bromo-7-(3-fluorophenyl)-8-(1H-imidazol-1-ylcarbonyl)-3,4-dihydropyrrolo[1,2-a]pyrazine-2(1H)-carboxylate in the form of a beige-coloured powder.

m.p.: 168-169° C.

$^1$H NMR (DMSO-d$_6$) δ: 7.75 (s, 1H); 7.35 (s, 1H); 7.25 (m, 1H); 7.0 (m, 3H); 6.75 (s, 1H); 4.70 (s, 2H); 4.05 (m, 2H); 3.85 (m, 2H); 1.45 (s, 9H) ppm.

Step 16.11. tert-Butyl 8-carbamoyl-6-bromo-7-(3-fluoro-phenyl)-3,4-dihydropyrrolo[1,2-a]pyrazine-2(1H)-carboxylate

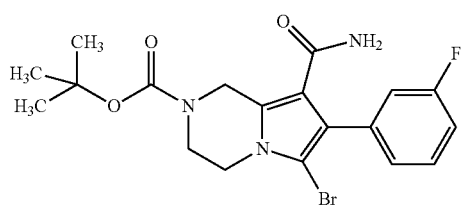 [SMILES: CC(C)(C)OC(=O)N1CCn2c(Br)c(-c3cccc(F)c3)c(C(N)=O)c2C1]

To 1.79 g (3.66 mmol) of tert-butyl 6-bromo-7-(3-fluorophenyl)-8-(1H-imidazol-1-ylcarbonyl)-3,4-dihydropyrrolo[1,2-a]pyrazine-2(1H)-carboxylate in an autoclave are added 30 ml of 33% aqueous ammonia. The mixture is stirred for 5 hours 30 minutes at 90° C. and, after cooling, is then poured into water, to give 1.26 g of tert-butyl 8-carbamoyl-6-bromo-7-(3-fluorophenyl)-3,4-dihydropyrrolo[1,2-a]pyrazine-2(1H)-carboxylate after drying over potassium hydroxide.

m.p.: 168-174° C.

$^1$H NMR (DMSO-d$_6$) δ: 7.50 (m, 1H); 7.20 (m, 3H); 7.05 (broad s, 1H); 6.00 (broad s, 1H); 4.75 (s, 2H); 3.95 (m, 2H); 3.80 (m, 2H); 1.45 (s, 9H) ppm.

Step 16.12. 6-Bromo-7-(3-fluorophenyl)-1,2,3,4-tetrahydropyrrolo[1,2-a]pyrazine-8-carboxamide

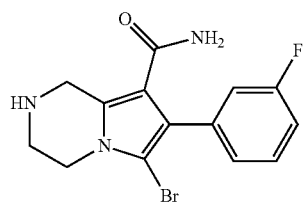 [SMILES: NC(=O)c1c(-c2cccc(F)c2)c(Br)n2c1CNCC2]

To a solution of 1.24 g (2.83 mmol) of tert-butyl 8-carbamoyl-6-bromo-7-(3-fluorophenyl)-3,4-dihydropyrrolo[1,2-a]pyrazine-2(1H)-carboxylate in 10 ml of dichloromethane are added slowly 2.8 ml (28 mmol) of trifluoroacetic acid. After stirring for 1 hour at room temperature, the solvent is evaporated off under reduced pressure, the residue is taken up in water and the aqueous phase is basified by addition of aqueous ammonia. The solid formed is separated out by filtration and rinsed with water, to give 0.92 g of 6-bromo-7-(3-fluorophenyl)-1,2,3,4-tetrahydropyrrolo[1,2-a]pyrazine-8-carboxamide in the form of a beige-coloured powder after drying under reduced pressure in the presence of potassium hydroxide.

m.p.: 216-218° C.

$^1$H NMR (DMSO-d$_6$) δ: 7.35 (m, 1H); 7.05 (m, 3H); 6.80 (broad s, 1H); 6.00 (broad s, 1H); 3.95 (s, 2H); 3.65 (t, 2H); 3.00 (t, 2H) ppm.

Step 16.13. 6-Bromo-1\7$^2$-(tert-butyl)-7-(3-fluorophenyl)-3,4-dihydropyrrolo[1,2-a]pyrazine-2,8 (1H)-dicarboxamide

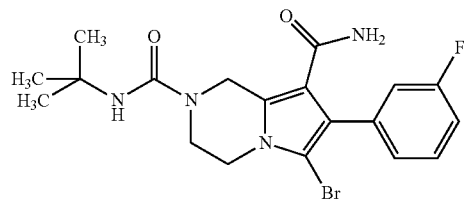 [SMILES: CC(C)(C)NC(=O)N1CCn2c(Br)c(-c3cccc(F)c3)c(C(N)=O)c2C1]

To a suspension of 0.24 g (0.71 mmol) of 6-bromo-7-(3-fluorophenyl)-1,2,3,4-tetrahydropyrrolo[1,2-a]pyrazine-8-carboxamide is added 0.30 ml (2.13 mmol) of triethylamine and then, at 0° C., 0.10 ml (0.85 mmol) of tert-butyl isocyanate. After reaction for 1 hour at room temperature, the mixture is treated with aqueous 1N sodium hydroxide solution and the product is extracted with dichloromethane. The organic phase is dried over sodium sulfate and filtered, and the solvent is evaporated off under reduced pressure. The residue is purified by chromatography on a column of 40 g of silica gel, eluting with a mixture of 4% methanol in dichloromethane, to give 0.16 g of 6-bromo-7-(3-fluorophenyl)-N$^2$-(tert-butyl)-3,4-dihydropyrrolo[1,2-a]pyrazine-2,8(1H)-dicarboxamide in the form of a powder after recrystallization from 10 ml of acetonitrile, filtering and drying under reduced pressure.

m.p.: 184-189° C.

$^{1}$H NMR (DMSO-d$_{6}$) δ: 7.45 (m, 1H); 7.15 (m, 3H); 7.00 (broad s, 1H); 6.15 (broad s and s, 2H); 4.80 (s, 2H); 3.90 (m, 2H); 3.75 (m, 2H); 1.30 (m, 9H) ppm.

Example 17 (Compound 105)

N$^{2}$-(tert-Butyl)-6-cyano-7-(3-fluorophenyl)-3,4-dihydropyrrolo[1,2-a]pyrazine-2,8(1H)-dicarboxamide

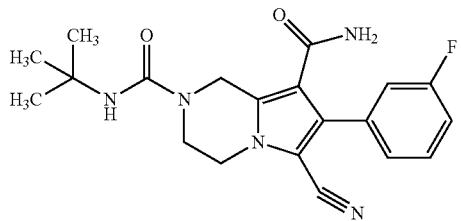 [SMILES: CC(C)(C)NC(=O)N1CCn2c(C#N)c(-c3cccc(F)c3)c(C(N)=O)c2C1]

Step 17.1. 2-tert-Butyl 8-ethyl 6-cyano-7-(3-fluorophenyl)-3,4-dihydropyrrolo[1,2-a]pyrazine-2,8(1H)-dicarboxylate

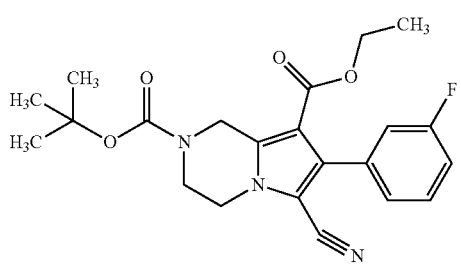 [SMILES: CCOC(=O)c1c(-c2cccc(F)c2)c(C#N)n2c1CN(C(=O)OC(C)(C)C)CC2]

To a solution, under argon and cooled to 10° C., of 2.52 g (6.49 mmol) of 2-tert-butyl 8-ethyl 7-(3-fluorophenyl)-3,4-dihydropyrrolo[1,2-a]pyrazine-2,8(1H)-dicarboxylate in 20 ml of dichloromethane is added dropwise 0.62 ml (7.14 mmol) of chlorosulfonyl isocyanate (CAS 1189-71-5) and the mixture is left stirring at 0° C. for 1 hour. 3.3 ml (65 mmol) of dimethylformamide are then added dropwise to the mixture, cooled to −10° C. After stirring for 5 hours at room temperature, the mixture is poured into 60 ml of aqueous 1N sodium hydroxide solution and the product is extracted with dichloromethane. The solution is dried over sodium sulfate and the solvent is evaporated off under reduced pressure, to give a yellow oil, which is chromatographed on a column of g of silica gel, eluting with a mixture of 20% ethyl acetate in cyclohexane, to give 1.24 g of 2-tert-butyl 8-ethyl 6-cyano-7-(3-fluorophenyl)-3,4-dihydropyrrolo[1,2-a]pyrazine-2,8(1H)-dicarboxylate in the form of a white powder after crystallizing from diisopropyl ether, filtering off and drying.

m.p.: 129-131° C.

$^{1}$H NMR (DMSO-d$_{6}$) δ: 7.6-7.2 (m, 4H); 4.84 (s, 2H); 4.2 (m, 2H); 4.10 (q, 2H); 3.83 (m, 2H); 1.45 (s, 9H); 1.10 (t, 3H) ppm.

Step 17.2. 2-(tert-Butoxycarbonyl)-6-cyano-7-(3-fluorophenyl)-1,2,3,4-tetrahydropyrrolo[1,2-a]pyrazine-8-carboxylic acid

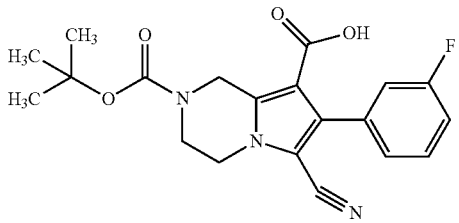 [SMILES: CC(C)(C)OC(=O)N1CCn2c(C#N)c(-c3cccc(F)c3)c(C(=O)O)c2C1]

To a suspension of 1.24 g (3.00 mmol) of 2-tert-butyl 8-ethyl 6-cyano-7-(3-fluorophenyl)-3,4-dihydropyrrolo[1,2-a]pyrazine-2,8(1H)-dicarboxylate in 15 ml of a mixture of ethanol, water and tetrahydrofuran (1:1:1) is added 0.086 g (3.6 mmol) of lithium hydroxide, and the mixture is heated at 60° C. for 1 day. The mixture is then taken up in 60 ml of dichloromethane and is acidified by addition of aqueous 1N sulfuric acid. The organic phase is separated out and dried over sodium sulfate, and the solvent is evaporated off under reduced pressure to give a solid, which is triturated in acetonitrile to give 1.07 g of 2-(tert-butyloxycarbonyl)-6-cyano-7-(3-fluorophenyl)-1,2,3,4-tetrahydropyrrolo[1,2-a]pyrazine-8-carboxylic acid in the form of a white powder.

m.p.: >210° C.

$^{1}$H NMR (DMSO-d$_{6}$) δ: 12.5 (broad s, 1H); 7.45 (m, 1H) 7.25 (m, 3H); 4.83 (s, 2H); 4.12 (m, 2H); 3.82 (m, 2H); 1.45 (s, 9H) ppm.

Step 17.3. tert-Butyl 6-cyano-7-(3-fluorophenyl)-8-(1H-imidazol-1-ylcarbonyl)-3,4-dihydropyrrolo[1,2-a]pyrazine-2 (1H)-carboxylate

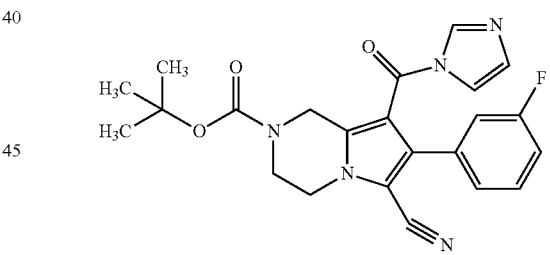

To a solution of 1.21 g (3.14 mmol) of 2-(tert-butyloxycarbonyl)-6-cyano-7-(3-fluorophenyl)-1,2,3,4-tetrahydropyrrolo[1,2-a]pyrazine-8-carboxylic acid in 10 ml of tetrahydrofuran is added 0.560 g (3.45 mmol) of carbonyl-diimidazole (CAS 530-62-1). After reaction for 1 hour 30 minutes at 60° C., the mixture is cooled and taken up in water, and the product is extracted with dichloromethane. The organic phase is dried over sodium sulfate and the solvent is evaporated off under reduced pressure, to give a yellow oil, which is chromatographed on a column of 24 g of silica gel, eluting with a mixture of 3% methanol in dichloromethane, to give 1.35 g of tert-butyl 6-cyano-7-(3-fluorophenyl)-8-(1H-imidazol-1-ylcarbonyl)-3,4-dihydropyrrolo[1,2-a]pyrazine-2(1H)-carboxylate in the form of a white foam.

$^{1}$H NMR (DMSO-d$_{6}$) δ: 7.64 (s, 1H); 7.3-6.9 (m, 5H); 6.84 (m, 1H); 4.90 (s, 2H); 4.23 (m, 2H); 4.00 (m, 2H); 1.51 (s, 9H) ppm. rmal Step 17.4. tert-Butyl 8-carbamoyl-6-cyano-7-(3-fluorophenyl)-3,4-dihydropyrrolo[1,2-a]pyrazine-2(1H)-carboxylate

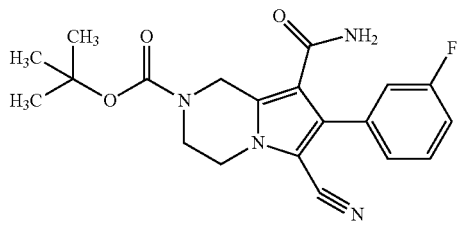

To 1.35 g (3.10 mmol) of tert-butyl 6-cyano-7-(3-fluorophenyl)-8-(1H-imidazol-1-ylcarbonyl)-3,4-dihydropyrrolo[1,2-a]pyrazine-2(1H)-carboxylate in an autoclave are added 10 ml of 30% aqueous ammonia. The mixture is stirred for 1 hour at 50° C. and, after cooling, is poured into 60 ml of water, to give 1.05 g of tert-butyl 8-carbamoyl-6-cyano-7-(3-fluorophenyl)-3,4-dihydropyrrolo[1,2-a]pyrazine-2(1H)-carboxylate after drying over potassium hydroxide.

m.p.: 208-210° C.

$^1$H NMR (CDCl$_3$) δ: 7.6-7.1 (m, 4H); 5.20 (broad s, 2H); 5.00 (s, 2H); 4.14 (m, 2H); 3.93 (m, 2H); 1.52 (s, 9H) ppm.

Step 17.5. 6-Cyano-7-(3-fluorophenyl)-1,2,3,4-tetrahydropyrrolo[1,2-a]pyrazine-8-carboxamide

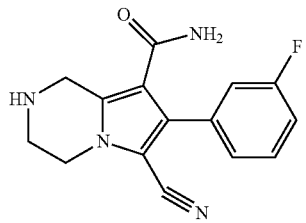 [SMILES: N#Cc1c(-c2cccc(F)c2)c(C(N)=O)c2n1CCNC2]

To a solution of 1.05 g (2.73 mmol) of tert-butyl 8-carbamoyl-6-cyano-7-(3-fluorophenyl)-3,4-dihydropyrrolo[1,2-a]pyrazine-2(1H)-carboxylate in 10 ml of dichloromethane are added slowly 2.7 ml (27 mmol) of trifluoroacetic acid. After stirring for 1 hour at room temperature, the solvent is evaporated off under reduced pressure, the residue is taken up in water and the aqueous phase is basified by addition of aqueous ammonia. The solid formed is separated out by filtration and rinsed with water, to give 0.71 g of 6-cyano-7-(3-fluorophenyl)-1,2,3,4-tetrahydropyrrolo[1,2-a]pyrazine-8-carboxamide in the form of a white powder after drying under reduced pressure.

m.p.: 195° C. (decomposition)

$^1$H NMR (DMSO-d$_6$) δ: 7.5 (m, 1H); 7.25 (m, 3H); 6.80 (broad s, 1H); 4.02 (s, 2H); 3.96 (t, 2H); 3.10 (t, 2H) ppm.

Step 17.6. N$^2$-(tert-Butyl)-6-cyano-7-(3-fluorophenyl)-3,4-dihydropyrrolo[1,2-a]pyrazine-2,8(1H)-dicarboxamide

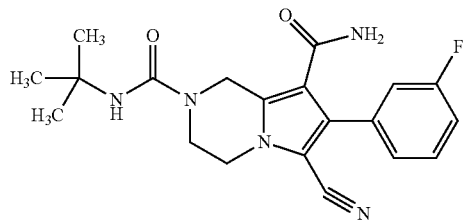 [SMILES: CC(C)(C)NC(=O)N1CCn2c(C#N)c(-c3cccc(F)c3)c(C(N)=O)c2C1]

To a suspension of 0.50 g (0.53 mmol) of 6-cyano-7-(3-fluorophenyl)-1,2,3,4-tetrahydropyrrolo[1,2-a]pyrazine-8-carboxamide is added 0.07 ml (0.6 mmol) of tert-butyl isocyanate. After reaction for 2 hours at room temperature, the solvent is evaporated off under reduced pressure and the solid residue is recrystallized from acetonitrile, to give 0.16 g of 6-cyano-7-(3-fluorophenyl)-N$^2$-(tert-butyl)-3,4-dihydropyrrolo[1,2-a]pyrazine-2,8(1H)-dicarboxamide in the form of a white powder after filtering off and drying under reduced pressure.

m.p.: >217° C.

$^1$H NMR (DMSO-d$_6$) δ: 7.6 and 7.3 (m and m, 4H); 6.95 (broad s, 1H); 6.25 (s, 1H); 4.75 (s, 2H); 4.10 (m, 2H); 3.85 (m, 2H); 1.33 (m, 9H) ppm.

Example 18 (Compound 87)

6-Chloro-7-(3-fluorophenyl)-N$^2$-[4-[(1,1-dimethylethoxy)imino]cyclohexyl]-3,4-dihydropyrrolo[1,2-a]pyrazine-2,8(1H)-dicarboxamide Step 18.1. 4-Nitrophenyl[4-[(1,1-dimethylethoxy)imino]-cyclohexyl]carbamate

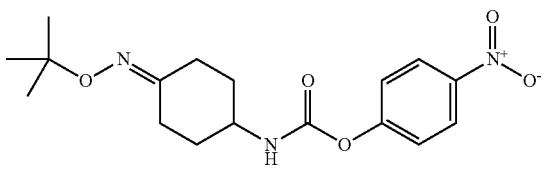 [SMILES: CC(C)(C)ON=C1CCC(NC(=O)Oc2ccc([N+](=O)[O-])cc2)CC1]

To a suspension of 1.15 g (5.16 mmol) of [4-[(1,1-dimethylethoxy)imino]cyclohexyl]amine hydrochloride (CAS 701249-71-0) in 30 ml of dichloromethane cooled to about 0° C. are added 1.15 g (5.68 mmol) of 4-nitrophenyl chloroformate (CAS 7693-46-1). 1.58 ml (11.4 mmol) of diisopropylethylamine are then added portionwise. Stirring is continued at 0° C. for 2 hours and the mixture is then allowed to warm to room temperature and is stirred for a further 2 hours. The solvent is then partially evaporated off under reduced pressure to a volume of about 8 ml. This solution is chromatographed on a column of 40 g of silica gel, eluting with a dichloromethane/ethyl acetate mixture (100/0 to 50/50), to give 1.19 g of 4-nitrophenyl[4-[(1,1-dimethylethoxy)imino]cyclohexyl]carbamate in the form of a white solid.

m.p.: 132.4° C.

$^1$H NMR (CDCl$_3$) δ: 8.20 (d, 2H); 7.25 (d, 2H); 4.95 (broad s, 1H); 3.75 (broad s, 1H); 3.15 (m, 1H); 2.45 (m, 1H); 2.25-1.90 (m, 4H); 1.55-1.30 (m, 4H); 1.20 (s, 9H) ppm.

Step 18.2. 6-Chloro-7-(3-fluorophenyl)-N$^2$-[4-[(1,1-dimethylethoxy)imino]cyclohexyl]-3,4-dihydropyrrolo[1,2-a]pyrazine-2,8(1H)-dicarboxamide

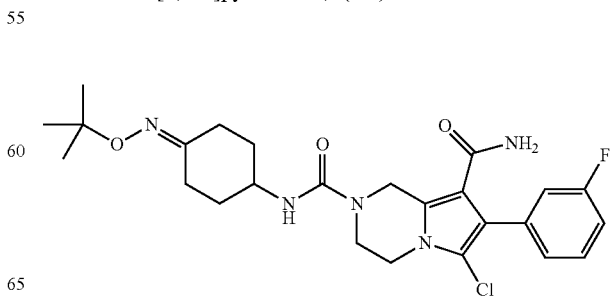

A suspension of 0.27 (0.82 mmol) of 6-chloro-7-(3-fluorophenyl)-1,2,3,4-tetrahydropyrrolo[1,2-a]pyrazine-8-carboxamide hydrochloride, 0.37 g (1.06 mmol) of 4-nitrophenyl[4-[(1,1-dimethylethoxy)imino]cyclohexyl]-carbamate and 0.33 g (2.45 mmol) of sodium carbonate in 30 ml of acetonitrile is heated at 60° C. for 3 hours. After cooling, the mixture is poured into water and the product is extracted with dichloromethane. After drying over sodium sulfate and filtration, the solvent is evaporated off under reduced pressure and the residue is purified by chromatography on a column of 40 g of silica gel, eluting with a mixture of dichloromethane/ethyl acetate (60/40 to 20/80), to give 0.18 g of 6-chloro-7-(3-fluorophenyl)-$N^2$-[4-[(1,1-dimethylethoxy)imino]cyclohexyl]-3,4-dihydropyrrolo-[1,2-a]pyrazine-2,8(1H)-dicarboxamide in the form of a yellowish powder, after evaporating the fractions down to a small volume of solvent, filtering off the crystallized product, washing with ethyl acetate and drying under reduced pressure.

m.p.: 195-198° C.

$^1$H NMR (DMSO-$d_6$) δ: 7.45 (m, 1H); 7.2 (m, 3H); 7.05 (broad s, 1H); 6.55 (d, 1H); 6.20 (broad s, 1H); 4.70 (s, 2H); 3.90 (m, 2H); 3.75 (m, 2H+1H); 3.00 (m, 1H); 2.30 (m, 1H); 2.15 (m, 1H); 2.00-1.80 (m, 3H); 1.50-1.25 (m, 2H); 1.20 (s, 9H) ppm.

Table 1 below illustrates the chemical structures and the physical properties of a number of compounds according to the invention.

In this table:

- the "m.p. ° C." column gives the melting points of the products in degrees Celsius. "N.D" means that the melting point is not determined,
- the "m/z" column gives the molecular ion (M+H$^+$) or (M−H$^-$) observed on analysis of the products by LC-MS.

TABLE 1

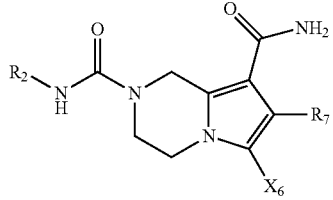

(I)

| No | $R_2$ | $X_6$ | $R_7$ | RT min | MW | m/z | m.p. ° C. |
|---|---|---|---|---|---|---|---|
| 1 | tert-butyl | hydrogen | phenyl | | 340.425 | 339 (M + H$^-$) | 156-158 |
| 2 | tert-butyl | hydrogen | 4-methoxy-phenyl | | 370.45 | 371 (M + H$^+$) | 197-198 |
| 3 | tert-butyl | methyl | phenyl | | 354.451 | 355 (M + H$^+$) | 187-189 |
| 4 | tert-butyl | methyl | 4-methoxy-phenyl | | 384.477 | 385 (M + H$^+$) | 164-166 |
| 5 | tert-butyl | methyl | 4-phenoxy-phenyl | | 446.548 | 447 (M + H$^+$) | 207-210 |
| 6 | cyclo-propyl | cyclo-propyl | 4-methoxy-phenyl | | 394.472 | 395 (M + H$^+$) | 231-234 |
| 7 | iso-propyl | cyclo-propyl | phenyl | 2.99 (C) | 366.462 | 367 (M + H$^+$) | |
| 8 | iso-propyl | cyclo-propyl | 4-methoxy-phenyl | | 396.488 | 397 (M + H$^+$) | 212-215 |
| 9 | iso-butyl | cyclo-propyl | phenyl | | 380.489 | 381 (M + H$^+$) | 173-175 |
| 10 | tert-butyl | cyclo-propyl | phenyl | | 380.489 | 381 (M + H$^+$) | 223-225 |
| 11 | tert-butyl | cyclo-propyl | 3-methyl-phenyl | 1.15 (A) | 394.516 | 395 (M + H$^+$) | |
| 12 | tert-butyl | cyclo-propyl | 4-methyl-phenyl | 1.22 (A) | 394.516 | 395 (M + H$^+$) | |
| 13 | tert-butyl | cyclo-propyl | 4-isopropyl-phenyl | 1.12 (A) | 422.57 | 423 (M + H$^+$) | |
| 14 | tert-butyl | cyclo-propyl | 4-cyclo-hexyl-phenyl | 1.29 (A) | 462.634 | 463 (M + H$^+$) | |
| 15 | tert-butyl | cyclo-propyl | biphenyl-4-yl | 1.09 (A) | 456.587 | 457 (M + H$^+$) | |
| 16 | tert-butyl | cyclo-propyl | 3-trifluoro-methyl-phenyl | 1.23 (A) | 448.486 | 449 (M + H$^+$) | |
| 17 | tert-butyl | cyclo-propyl | 3-dimethyl-carbamoyl-phenyl | 1.24 (A) | 451.568 | 452 (M + H$^+$) | |
| 18 | tert-butyl | cyclo-propyl | 4-cyclo-propylcar-bamoyl-phenyl | 1.14 (A) | 463.579 | 464 (M + H$^+$) | |
| 19 | tert-butyl | cyclo-propyl | 4-(pyrrolidine-1-carbonyl)-phenyl | 1.25 (A) | 477.606 | 478 (M + H$^+$) | |

TABLE 1-continued (I)

| No | R₂ | X₆ | R₇ | RT min | MW | m/z | m.p. ° C. |
|----|----|----|----|--------|----|-----|-----------|
| 20 | tert-butyl | cyclo-propyl | 4-(methoxy-methyl-carbamoyl)-phenyl | 1.20 (A) | 467.567 | 468 (M + H⁺) | |
| 21 | tert-butyl | cyclo-propyl | 3-cyano-phenyl | 1.25 (A) | 405.499 | 406 (M + H⁺) | |
| 22 | tert-butyl | cyclo-propyl | 4-cyano-phenyl | 1.28 (A) | 405.499 | 406 (M + H⁺) | |
| 23 | tert-butyl | cyclo-propyl | 4-(5-methyl-[1.3.4]oxa-diazol-2-yl)-phenyl | 0.95 (A) | 462.551 | 463 (M + H⁺) | |
| 24 | tert-butyl | cyclo-propyl | 4-trifluoro-methyl-phenyl | 1.77 (B) | 448.486 | 449 (M + H⁺) | |
| 25 | tert-butyl | cyclo-propyl | naphthalen-2-yl | 1.24 (A) | 430.549 | 431 (M + H⁺) | |
| 26 | tert-butyl | cyclo-propyl | 3-[(dimethyl-sulfamoyl)-amino]phenyl | 1.27 (A) | 502.637 | 503 (M + H⁺) | |
| 27 | tert-butyl | cyclo-propyl | 3-pyrazol-1-yl-phenyl | 1.23 (A) | 446.552 | 447 (M + H⁺) | |
| 28 | tert-butyl | cyclo-propyl | 4-dimethyl-amino-phenyl | 1.10 (A) | 423.558 | 424 (M + H⁺) | |
| 29 | tert-butyl | cyclo-propyl | 4-methanesul-fonylamino-phenyl | 1.16 (A) | 473.595 | 474 (M + H⁺) | |
| 30 | tert-butyl | cyclo-propyl | 4-morpholin-4-yl-phenyl | 1.12 (A) | 465.594 | 466 (M + H⁺) | |
| 31 | tert-butyl | cyclo-propyl | 4-pyrazol-1-yl-phenyl | 1.18 (A) | 446.552 | 447 (M + H⁺) | |
| 32 | tert-butyl | cyclo-propyl | 3-methoxy-phenyl | 1.97 (B) | 410.515 | 411 (M + H⁺) | |
| 33 | tert-butyl | cyclo-propyl | 3-cyclo-propylmethoxy-phenyl | 1.15 (A) | 450.58 | 451 (M + H⁺) | |
| 34 | tert-butyl | cyclo-propyl | 3-benzyloxy-phenyl | | 486.613 | 487 (M + H⁺) | 156-158 |
| 35 | tert-butyl | cyclo-propyl | 3-trifluoro-methoxy-phenyl | 1.17 (A) | 464.485 | 465 (M + H⁺) | |
| 36 | tert-butyl | cyclo-propyl | 4-methoxy-phenyl | 1.19 (A) | 410.515 | 411 (M + H⁺) | 177-179 |
| 37 | tert-butyl | cyclo-propyl | 4-cyclo-propylmethoxy-phenyl | 1.17 (A) | 450.58 | 451 (M + H⁺) | |
| 38 | tert-butyl | cyclo-propyl | 4-butoxy-phenyl | 1.14 (A) | 452.595 | 453 (M + H⁺) | |
| 39 | tert-butyl | cyclo-propyl | 4-phenoxy-phenyl | 1.11 (A) | 472.586 | 473 (M + H⁺) | 157-159 |
| 40 | tert-butyl | cyclo-propyl | 4-benzyloxy-phenyl | | 486.613 | 487 (M + H⁺) | 203-206 |
| 41 | tert-butyl | cyclo-propyl | 4-(4-fluoro-benzyloxy)-phenyl | 1.49 (B) | 504.603 | 505 (M + H⁺) | |
| 42 | tert-butyl | cyclo-propyl | 3-chloro-4-(4-fluoro-benzyloxy)-phenyl | 1.69 (B) | 539.048 | 539 (M + H⁺) | |
| 43 | tert-butyl | cyclo-propyl | 4-cyanometh-oxy-phenyl | 1.23 (A) | 435.525 | 436 (M + H⁺) | |
| 44 | tert-butyl | cyclo-propyl | 4-trifluoro-methoxy-phenyl | 1.10 (A) | 464.485 | 465 (M + H⁺) | |
| 45 | tert-butyl | cyclo-propyl | 2-fluoro-phenyl | 1.21 (A) | 398.479 | 399 (M + H⁺) | |

TABLE 1-continued (I)

| No | R₂ | X₆ | R₇ | RT min | MW | m/z | m.p. °C |
|---|---|---|---|---|---|---|---|
| 46 | tert-butyl | cyclo-propyl | 3-fluoro-phenyl | 1.22 (A) | 398.479 | 399 (M + H⁺) | |
| 47 | tert-butyl | cyclo-propyl | 4-fluoro-phenyl | | 398.479 | 399 (M + H⁺) | 220-223 |
| 48 | tert-butyl | cyclo-propyl | 4-methylsulfanyl-phenyl | 1.17 (A) | 426.582 | 427 (M + H⁺) | |
| 49 | cyclo-hexyl | cyclo-propyl | phenyl | 3.34 (C) | 406.527 | 407 (M + H⁺) | |
| 50 | cyclo-hexylmethyl | cyclo-propyl | phenyl | 3.54 (C) | 420.554 | 421 (M + H⁺) | |
| 51 | 1,1'-bi(cyclo-propyl)-1-yl | cyclo-propyl | 4-methoxy-phenyl | | 434.537 | 435 (M + H⁺) | 175-177 |
| 52 | 2,4,4-trimethylpentan-2-yl | cyclo-propyl | phenyl | 3.74 (C) | 436.596 | 437 (M + H⁺) | |
| 53 | hexahydro-2,5-methanopentalen-3a(1H)-yl | cyclo-propyl | 4-methoxy-phenyl | | 474.602 | 475 (M + H⁺) | 216-219 |
| 54 | adamantan-1-yl | cyclo-propyl | phenyl | 2.53 (D) | 458.603 | 459 (M + H⁺) | |
| 55 | adamantan-1-yl | cyclo-propyl | 4-methoxy-phenyl | | 488.628 | 489 (M + H⁺) | 224-226 |
| 56 | tetrahydro-2H-pyran-4-yl | cyclo-propyl | 4-methoxy-phenyl | | 438.525 | 439 (M + H⁺) | 176-177 |
| 57 | 1-methoxy-2-methylpropan-2-yl | cyclo-propyl | 4-methoxy-phenyl | | 440.541 | 441 (M + H⁺) | 168-170 |
| 58 | tert-butyl | fluoro | phenyl | | 358.415 | 359 (M + H⁺) | 213-215 |
| 59 | iso-butyl | chloro | phenyl | | 374.87 | 373 (M + H⁺) | 211-213 |
| 60 | tert-butyl | chloro | phenyl | | 374.87 | 375 (M + H⁺) | 197-199* 192-195** |
| 61 | tert-butyl | chloro | 3-methyl-phenyl | | 388.896 | 389 (M + H⁺) | 196-197 |
| 62 | tert-butyl | chloro | 3-methoxy-phenyl | | 404.896 | 405 (M + H⁺) | 206-209 |
| 63 | tert-butyl | chloro | 3-trifluoro-methoxy-phenyl | | 458.866 | 457 (M − H⁻) | 186-188 |
| 64 | tert-butyl | chloro | 4-methoxy-phenyl | | 404.896 | 405 (M + H⁺) | 168-170 |
| 65 | tert-butyl | chloro | 3-cyano-phenyl | | 399.88 | 400 (M + H⁺) | 192-195 |
| 66 | tert-butyl | chloro | 3-trifluoro-methyl-phenyl | | 442.867 | 441 (M − H⁻) | 196-198 |
| 67 | tert-butyl | chloro | 3-fluoro-phenyl | | 392.86 | 393 (M + H⁺) | 196-198 |
| 68 | cyclo-propylmethyl | chloro | phenyl | | 372.854 | 371 (M − H⁻) | 205-207 |
| 69 | 3-methyl-butyl | chloro | phenyl | | 388.896 | 389 (M + H⁺) | 154-155 |
| 70 | 2,2-dimethyl-propyl | chloro | phenyl | | 388.896 | 387 (M − H⁻) | 224-226 |
| 71 | 2-ethyl-butyl | chloro | phenyl | | 402.923 | 401 (M − H⁻) | 171-173 |
| 72 | 3,3-dimethyl-butyl | chloro | phenyl | | 402.923 | 401 (M − H⁻) | 182-184 |
| 73 | 3-hydroxy-2,2-dimethyl-propyl | chloro | 3-fluoro-phenyl | | 422.886 | 423 (M + H⁺) | 205-207 |
| 74 | 3-hydroxy-2,2-dimethyl-propyl | chloro | 3-trifluoro-methyl-phenyl | | 472.893 | 473 | 185-187 |
| 75 | [1-(hydroxymethyl)-cyclo-propyl]methyl | chloro | 3-fluoro-phenyl | | 420.87 | 421 (M + H⁺) | 204-206 |
| 76 | 2,2,2-trifluoro-ethyl | chloro | phenyl | | 400.786 | 401 (M + H⁺) | 210-213 |

TABLE 1-continued (I)

| No | R₂ | X₆ | R₇ | RT min | MW | m/z | m.p. ° C. |
|---|---|---|---|---|---|---|---|
| 77 | 2,2,2-trifluoro-ethyl | chloro | 3-fluoro-phenyl | | 418.776 | 419 (M + H⁺) | 208-213 |
| 78 | (2S)-1,1,1-trifluoropropan-2-yl | chloro | 3-fluoro-phenyl | | 432.803 | 433 (M + H⁺) | 190-193 |
| 79 | 1,1,1-trifluoro-2-methylpropan-2-yl | chloro | 3-fluoro-phenyl | | 446.83 | 447 (M + H⁺) | 183-187 |
| 80 | 3,3,3-trifluoro-propyl | chloro | 3-fluoro-phenyl | | 432.803 | 433 (M + H⁺) | 119-124 |
| 81 | 4,4,4-trifluoro-butyl | chloro | 3-fluoro-phenyl | | 446.83 | 447 (M + H⁺) | 100-117 |
| 82 | cyclo-hexyl | chloro | phenyl | | 400.908 | 401 (M + H⁺) | 208-209 |
| 83 | 4-hydroxy-cyclo-hexyl | chloro | 3-fluoro-phenyl | | 434.897 | 435 (M + H⁺) | 251-253 |
| 84 | trans-4-hydroxy-4-methyl-cyclohexyl | chloro | 3-fluoro-phenyl | | 448.923 | 449 (M + H⁺) | 228-232 |
| 85 | trans-4-hydroxy-4-trifluoromethyl-cyclohexyl | chloro | 3-fluoro-phenyl | | 502.894 | 503 (M + H⁺) | 153-168 |
| 86 | (4-methyl-oxyimino-cyclohexyl) | chloro | 3-fluoro-phenyl | | 461.922 | 462 (M + H⁺) | 180-182 |
| 87 | (4-cert-butyl-oxyimino-cyclohexyl) | chloro | 3-fluoro-phenyl | | 504.003 | 504 (M + H⁺) | 195-198 |
| 88 | bicyclo[2.2.1]hept-2-yl | chloro | phenyl | | 412.918 | 414 (M + H⁺) | 231-233 |
| 89 | 4,4-difluoro-cyclohexyl | chloro | 3-fluoro-phenyl | | 454.878 | 455 (M + H⁺) | 212-214 |
| 90 | 2-oxetan-3-yl | chloro | 3-fluoro-phenyl | | 392.816 | 393 (M + H⁺) | 184-186 |
| 91 | 3-methyl-oxetan-3-yl-methyl | chloro | 3-fluoro-phenyl | | 420.870 | 421 (M + H⁺) | 249-253 |
| 92 | tetrahydro-furan-3-yl | chloro | phenyl | | 388.853 | 389 (M + H⁺) | 181-185 |
| 93 | tetrahydro-2H-pyran-4-yl | chloro | phenyl | | 402.88 | 403 (M + H⁺) | 227-229 |
| 94 | tetrahydro-2H-pyran-4-yl | chloro | 3-methyl-phenyl | | 416.906 | 417 (M + H⁺) | 231-234 |
| 95 | tetrahydro-2H-pyran-4-yl | chloro | 3-cyano-phenyl | | 427.89 | 428 (M + H⁺) | 236-238 |
| 96 | tetrahydro-2H-pyran-4-yl | chloro | 3-trifluoro-methyl-phenyl | | 470.877 | 471 (M + H⁺) | 220-222 |
| 97 | tetrahydro-2H-pyran-4-yl | chloro | 3-trifluoro-methoxy-phenyl] | | 486.876 | 487 (M + H⁺) | 203-205 |
| 98 | tetrahydro-2H-pyran-4-yl | chloro | 3-fluoro-phenyl | | 420.87 | 421 (M + H⁺) | 223-225 |
| 99 | 2,2-dimethyl-tetrahydro-2H-pyran-4-yl | chloro | 3-fluoro-phenyl | | 448.923 | 449 (M + H⁺) | 141-143 |
| 100 | cis-2,6-dimethyl-tetrahydro-2H-pyran-4-yl | chloro | 3-fluoro-phenyl | | 448.923 | 449 (M + H⁺) | 124-127 |
| 101 | 1,1-dioxydotetra-hydrothiophen-3-yl | chloro | phenyl | | 436.918 | 437 (M + H⁺) | 206-207 |
| 102 | 1,1-dioxydotetra-hydrothiophen-3-yl | chloro | 3-fluoro-phenyl | | 454.908 | 455 (M + H⁺) | 224-226 |
| 103 | 1,1-dioxydotetra-hydro-2H-thiopyran-4-yl | chloro | 3-fluoro-phenyl | | 468.935 | 469 (M + H⁺) | 238-239 |
| 104 | tert-butyl | bromo | 3-fluoro-phenyl | | 437.31 | 437 (M + H⁺) | 184-189 |
| 105 | tert-butyl | cyano | 3-fluoro-phenyl | | 383.425 | 384 (M + H⁺) | >217*** |

TABLE 1-continued

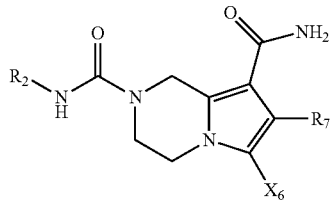

(I)

| No | R₂ | X₆ | R₇ | RT min | MW | m/z | m.p. ° C. |
|---|---|---|---|---|---|---|---|
| 106 | (2S)-1,1,1-tri-fluoropropan-2-yl | cyano | 3-fluoro-phenyl | | 423.368 | 424 | 176-178 |
| 107 | 1,1,1-trifluoro-2-methylpropan-2-yl | cyano | 3-fluoro-phenyl | | 437.395 | 438 | 202-204 |
| 108 | 4,4,4-trifluoro-butyl | cyano | 3-fluoro-phenyl | | 437.395 | 438 | 169-171 |
| 109 | tetrahydro-2H-pyran-4-yl | cyano | 3-fluoro-phenyl | | 411.435 | 412 | 232-234 |
| 110 | 4,4-difluoro-cyclohexyl | cyano | 3-fluoro-phenyl | | 445.443 | 446 | 237-240 |

Example 78 -6-chloro-7-(3-fluorophenyl)-N²-[(2S)-1,1,1-trifluoropropan-2-yl]-3,4-dihydropyrrolo[1,2-a]pyrazine-2,8(1H)-dicarboxamide $\alpha_D$ + 9.1 (c = 0.345, methanol)

*acetonitrile
**ethyl acetate
***decomposition (A): The LC/MS spectra were recorded using a BEH C18 (2.1 × 50 mm; 1.7 μm) reverse-phase column using a gradient of water containing 0.1% formic acid and acetonitrile containing 0.08% formic acid from 95:5 to 5:95 (1.1 minutes); from 5:95 to 5:95 (1.7 minutes); from 5:95 to 95:5 (1.8 minutes); from 95:5 to 95:5 (2 minutes)
The detection by mass spectrometry was performed using a Waters SQQ Single Quadrupole system with ES+ electrospray ionization.
(B): The LC/MS spectra were recorded using a Merck Chromolith FastGrad. RP-18e, (50 × 2 mm) reverse-phase column using a gradient of water containing 0.05% trifluoroacetic acid and acetonitrile containing 0.05% trifluoroacetic acid from 98:2 to 98:2 (0.2 minute); from 98:2 to 2:98 (2.4 minutes); from 2:98 to 2:98 (3.2 minutes); from 2:98 to 98:2 (3.3 minutes); from 98:2 to 98:2 (4 minutes) at a flow rate of 2.0 ml/min.
The detection by mass spectrometry was performed using a Waters LCT classic TOF-MS system.
(C) The LC/MS spectra were recorded using a YMC-Pack Jsphere H80 2.4 × 33 mm; 4 μm) reverse-phase column, using a gradient of water containing 0.05% trifluoroacetic acid and acetonitrile containing 0.05% trifluoroacetic acid from 98:2 to 98:2 (1 minute); from 98:2 to 5:95 (5 minutes); from 5:95 to 2:98 (5:95 minutes) at a flow rate of 2.0 ml/min.
The detection by mass spectrometry was performed using a Waters LCT classic TOF-MS system.
(D) The LC/MS spectra were recorded using a WatersXBridgeC18 (4.6 × 50 mm; 2.5 μm) reverse-phase column, using a gradient of water containing 0.05% trifluoroacetic acid and acetonitrile containing 0.05% trifluoroacetic acid from 95:5 to 98:2 (0.2 minute); from 95:5 to 5:95 (2.4 minutes); from 5:95 to 5:95 (5:3.6 minutes) at a flow rate of 1.7 ml/min and at 50° C.

BIOLOGICAL EXAMPLES

The capacity of the compounds of the invention to inhibit the phosphorylation of casein by casein kinase 1 epsilon and/or delta may be evaluated according to the procedures described in document US 2005/0 131 012.

Test A: Inhibitory Activity on CK1 Epsilon Measured by Assay on an ATP-³³P Filter Plate The effect of the compounds on inhibition of the phosphorylation of casein by the enzyme casein kinase 1 epsilon (CK1 epsilon) is measured, using a casein assay via filtration of ATP-³³P in vitro.

Casein kinase 1 epsilon (0.58 mg/ml) is obtained via fermentation and purification processes performed according to methods that are well known to those skilled in the art, or may also be obtained from Invitrogen Corporation™ (human CK1 epsilon).

The compounds are tested at five different concentrations so as to generate $IC_{50}$ values, i.e. the concentration at which a compound is capable of inhibiting the enzymatic activity by 50%, or alternatively the percentage of inhibition at a concentration of 10 micromolar.

"U"-bottomed Falcon plates are prepared by placing 5 μL of solutions of the compounds according to the invention at concentrations of 10, 1, 0.1, 0.01 or 0.001 μM in different wells. The solutions of the compounds according to the invention at these various concentrations are prepared by diluting in a test buffer (Tris 50 mM pH 7.5, $MgCl_2$ 10 M, DTT 2 mM and EGTA 1 mM) a stock solution in DMSO at a concentration of 10 mM. Next, 5 μL of dephosphorylated casein are added to a final concentration of 0.2 μg/μL, 20 μL of CK1 epsilon to a final concentration of 3 ng/μL, and 20 μL of ATP-³³P to a final concentration of 0.02 μCi/μL mixed with cold ATP (10 μM final—approximately 2×10⁶ CPM per well). The final total test volume per well is equal to 50 μL.

The "U"-bottomed Falcon® test plate mentioned above is vortexed, and then incubated at room temperature for 2 hours. After 2 hours the reaction is stopped by adding an ice-cold solution of 65 μL of cold ATP (2 mM) prepared in test buffer.

100 μL of the reaction mixture are then transferred from the "U"-bottomed Falcon® plate into Millipore® MAPH filter plates, preimpregnated with 25 μL of ice-cold 100% TCA.

The Millipore MAPH filter plates are agitated gently and are left to stand at room temperature for at least 30 minutes to precipitate the proteins.

After 30 minutes, the filter plates are sequentially washed and filtered with 2×150 μL of 20% TCA, 2×150 μL of 10% TCA and 2×150 μL of 5% TCA (6 washes in total per plate/900 μL per well).

The plates are left to dry overnight at room temperature. Next, 40 μL of Microscint-20 Packard® scintillation liquid are added per well and the plates are closed in a leaktight manner. The radiation emitted by each well is then measured for 2 minutes in a TopCount NXT Packard® scintillation counter, in which the values of CPM/well are measured.

The percentage inhibition of the capacity of the enzyme to phosphorylate the substrate (casein) is determined for each concentration of test compound. These inhibition data expressed as percentages are used to calculate the $IC_{50}$ value for each compound compared with the controls.

The kinetic studies determined the $K_M$ value for ATP as being 21 µM in this test system.

Table 2 below gives the $IC_{50}$ values or the $IC_{50}$ inhibition ranges (result of several experiments) for the phosphorylation of Casein Kinase 1 Epsilon for a number of compounds according to the invention.

TABLE 2

| No. | CK1 epsilon $IC_{50}$ (nM) |
|---|---|
| 1 | 12-35 |
| 2 | <1 |
| 3 | 5-104 |
| 4 | 1-3 |
| 5 | 34-78 |
| 6 | 28-57 |
| 7 | 42 |
| 8 | 221-273 |
| 9 | 49 |
| 10 | 15-77 |
| 11 | 3-6 |
| 12 | 12-12 |
| 13 | 450-1000 |
| 14 | 136-1090 |
| 15 | 2-4 |
| 16 | 19-57 |
| 17 | 958 |
| 18 | 963 |
| 19 | 587 |
| 20 | 620 |
| 21 | 26-46 |
| 22 | 25 |
| 23 | 65 |
| 24 | 84 |
| 25 | 33 |
| 26 | 521 |
| 27 | 23 |
| 28 | 4 |
| 29 | 532 |
| 30 | 331 |
| 31 | 5-29 |
| 32 | 1-7 |
| 33 | 847 |
| 34 | 315 |
| 35 | 25 |
| 36 | 46-75 |
| 37 | 62 |
| 38 | 152 |
| 39 | 4-36 |
| 40 | 38 |
| 41 | 42 |
| 42 | 16 |
| 43 | 24 |
| 44 | 33 |
| 45 | 12 |
| 46 | 5-11 |
| 47 | 45-146 |
| 48 | 1-2 |
| 49 | 17-28 |
| 50 | 25 |
| 51 | 40 |
| 52 | 45 |
| 53 | 7 |
| 54 | 6-6 |
| 55 | 3-5 |
| 56 | 26-38 |
| 57 | 36 |
| 58 | 5-28 |
| 59 | 8-13 |
| 60 | 1-12 |
| 61 | 1-8 |
| 62 | 1-4 |
| 63 | 29 |
| 64 | 1-5 |
| 65 | 1-2 |
| 66 | 3-6 |
| 67 | 1-5 |
| 68 | 10 |
| 69 | 5 |
| 70 | 4 |
| 71 | 4 |
| 72 | 1-17 |
| 73 | 1-11 |
| 74 | 6 |
| 75 | 4-5 |
| 76 | 10-27 |
| 77 | 2-8 |
| 78 | 3-3 |
| 79 | 1-4 |
| 80 | 2-16 |
| 81 | 2-16 |
| 82 | 1-7 |
| 83 | 2-4 |
| 84 | 1 |
| 85 | 2 |
| 86 | <1 |
| 87 | <1 |
| 88 | 3-5 |
| 89 | 1-3 |
| 90 | 6-7 |
| 91 | 4 |
| 92 | 11-13 |
| 93 | 21-28 |
| 94 | 2-18 |
| 95 | 6 |
| 96 | 19 |
| 97 | 122 |
| 98 | 2-16 |
| 99 | 4 |
| 100 | >1 |
| 101 | 9-24 |
| 102 | 4-11 |
| 103 | 7-14 |
| 104 | <1 |
| 105 | <1-1 |
| 106 | 2 |
| 107 | <1 |
| 108 | 4 |
| 109 | 9 |
| 110 | <1 |

Under these conditions, the compounds of the invention that are the most active have $IC_{50}$ values (concentrations that inhibit 50% of the enzymatic activity of casein kinase 1 epsilon) of between 1 nM and 1 µM, and more particularly between 1 nM and 100 nM.

Test B: Inhibitory Activity on CK1 Delta Measured by FRET

The capacity of the compounds of the invention to inhibit the phosphorylation of casein by the casein kinases 1 epsilon and delta may be evaluated using an FRET (Fluorescence Resonance Energy Transfer) fluorescence test with the aid of the "Z'Lyte™ kinase assay kit" (reference PV3670; Invitrogen Corporation™) according to the manufacturer's instructions.

The casein kinases 1 used are obtained from Invitrogen Corporation (human CK1 epsilon PV3500 and human CK1 delta PV3665).

A peptide substrate labelled at both ends with a fluorophore-donating group (coumarin) and a fluorophore-accepting group (fluorescein) constituting an FRET system is dephosphorylated in the presence of ATP by casein kinase 1 epsilon or delta in the presence of increasing concentrations of compounds of the invention.

The mixture is treated with a site-specific protease that specifically cleaves the substrate peptide to form two fluorescent fragments having a large fluorescence emission ratio.

The fluorescence observed is thus related to the capacity of the products of the invention to inhibit the phosphorylation of the substrate peptide by casein kinase 1 epsilon or casein kinase 1 delta.

The compounds of the invention are dissolved at different concentrations starting with a 10 mM stock solution in DMSO diluted in a buffer containing 50 mM HEPS, pH 7.5, 1 mM EGTA, 0.01% Brij-35, 10 mM $MgCl_2$ for casein kinase 1 epsilon and supplemented with Trizma Base (50 mM), pH 8.0 and $NaN_3$ (0.01% final) for casein kinase 1 delta.

The phosphorylation of the substrate peptide SER/THR 11 obtained from Invitrogen Corporation™ is performed at a final concentration of 2 μM. The ATP concentration is 4 times the $K_M$, this value being 2 μM for casein kinase 1 epsilon and 4 μM for casein kinase 1 delta.

The emitted fluorescence is measured at wavelengths of 445 and 520 nm (excitation at 400 nm).

Table 3 below gives the $IC_{50}$ values for the inhibition of phosphorylation of casein kinase 1 delta for a number of compounds according to the invention.

TABLE 3

| Compound | CK1 delta $IC_{50}$ (nM) |
| --- | --- |
| 10 | 31 |

Under these conditions, the compounds of the invention that are the most active have $IC_{50}$ values (concentration that inhibits 50% of the enzymatic activity of casein kinase 1 delta) of between 1 nM and 1 μM, and more particularly between 1 nM and 100 nM.

It is thus seen that the compounds according to the invention have inhibitory activity on the enzyme casein kinase 1 epsilon or casein kinase 1 delta.

Test C: Experimental Protocol for Circadian Cell Assay

Mper1-luc Rat-1 (P2C4) fibroblast cultures were prepared by dividing the cultures every 3-4 days (about 10-20% of confluence) on 150 cm² degassed polystyrene tissue culture flasks (Falcon® #35-5001) and maintained in growth medium [EMEM (Cellgro #10-010-CV); 10% foetal bovine serum (FBS; Gibco #16000-044); and 50 I.U./mL of penicillin-streptomycin (Cellgro #30-001-Cl)] at 37° C. and under 5% $CO_2$.

Cells obtained from Rat-1 fibroblast cultures at 30-50% of confluence as described above were co-transfected with vectors containing the selection marker for resistance to zeocin for a stable transfection and a luciferase reporter gene directed by the promoter mPer-1. After 24 to 48 hours, the cultures were divided on 96-well plates and maintained in growth medium supplemented with 50-100 μg/mL of zeocin (Invitrogen® #45-0430) for 10-14 days. The zeocin-resistant stable transfectants were evaluated for expression of the reporter by adding to the growth medium luciferin 100 μM (Promega® #E1603®) and by assaying the luciferase activity on a TopCount® scintillation counter (Packard model #C384V00). The Rat-1 cell clones expressing both zeocin resistance and luciferase activity directed by mPer1 were serum-shock-synchronized with 50% horse serum [HS (Gibco® #16050-122)] and the activity of the circadian reporter was evaluated. The P2C4 clone of fibroblasts Mper1-luc Rat-1 was selected to test the compound.

The Mper1-luc Rat-1 (P2C4) fibroblasts at 40-50% of confluence obtained according to the protocol described above were plated out onto 96-well opaque tissue culture plates (Perkin Elmer® #6005680). The cultures are maintained in growth medium supplemented with 100 μg/mL of zeocin (Invitrogen #45-0430) until they reached 100% of confluence (48-72 hours). The cultures were then synchronized with 100 μL of synchronization medium [EMEM (Cellgro #10-010-CV); 100 I.U./mL of penicillin-streptomycin (Cellgro #30-001-C1); 50% HS (Gibco #16050-122)] for 2 hours at 37° C. and under 5% $CO_2$. After synchronization, the cultures were rinsed with 100 μL of EMEM (Cellgro #10-010-CV) for 10 minutes at room temperature. After rinsing, the medium was replaced with 300 μL of $CO_2$-independent medium [$CO_2$I (Gibco #18045-088); L-glutamine 2 mM (Cellgro #25-005-C1); 100 U.I./mL of penicillin-streptomycin (Cellgro #30-001-C1); luciferin 100 μM (Promega #E 1603)]. The compounds of the invention tested for the circadian effects were added to $CO_2$-independent medium in DMSO at 0.3% (final concentration). The cultures were immediately closed in a leaktight manner with TopSeal-A® film (Packard #6005185) and transferred for the luciferase activity measurement.

After synchronization, the test plates were maintained at 37° C. in a tissue culture oven (Forma Scientific Model #3914). The in vivo luciferase activity was estimated by measuring the relative light emission on a TopCount scintillation counter (Packard model #C384V00).

The period analysis was performed either by determining the interval between the relative light emission minima over several days or by Fourier transform. The two methods produced a virtually identical period estimation on a range of circadian periods. The power is given in EC Delta (t+1 h), which is presented as the effective micromolar concentration that induce a 1-hour prolongation of the period. The data were analysed by adjusting a hyperbolic curve to the data expressed as change of period (y-axis) as a function of the concentration of the test compound (x-axis) in the XLfit™ software and the EC Delta (t+1 h) was interpolated from this curve.

Table 4 below gives the EC Delta (t+1 h) or the EC Delta (t+1 h) ranges (results from several experiments) for a number of compounds according to the invention.

TABLE 4

| Compound | CE Delta (t + 1 h) (nM) |
| --- | --- |
| 3 | 8 |
| 25 | 26 |
| 54 | 15 |
| 60 | 3-20 |

Under these conditions, the compounds of the invention that are the most active have EC Delta (t+1 h) values (effective micromolar concentration that induced a 1-hour prolongation of the period) of between 1 nM and 2 μM, and more particularly between 1 nM and 500 nM.

By inhibiting the enzymes CK1epsilon and/or CK1delta, the compounds that are the subject of the invention modulate the circadian periodicity, and may be useful for treating circadian rhythm disorders.

The compounds according to the invention may especially be used for the preparation of a medicament for preventing or treating sleep disorders; circadian rhythm disorders, especially such as those caused by jetlag, shift work, delayed sleep-phase syndrome and advanced sleep-phase syndrome.

According to one of its aspects, the invention relates to a compound of formula (I) in base form or in the form of an addition salt with a pharmaceutically acceptable acid, for preventing or treating sleeping disorders; circadian rhythm disorders, especially such as those caused by jetlag, shift work, delayed sleep-phase syndrome and advanced sleep-phase syndrome.

Among the sleep disorders that are especially distinguished are primary sleep disorders such as dyssomnia (for example primary insomnia), parasomnia, hypersomnia (for example excessive somnolence), narcolepsy, sleep disorders related to sleep apnoea, sleep disorders related to the circadian rhythm and other unspecified dyssomnias, sleep disorders associated with medical/psychiatric disorders, for instance Alzheimer's disease.

The compounds that are the subject of the invention also cause a circadian phase shift and such a property may be useful in the context of a potential monotherapy or combination therapy that is clinically effective in the case of mood disorders and/or in age- and/or ageing-related circadian-phase movement disorders.

According to one of its aspects, the invention relates to a compound of formula (I) in base form or in the form of an addition salt with a pharmaceutically acceptable acid, in the context of a potential monotherapy or combination therapy that is clinically effective in the case of mood disorders and/or in age- and/or ageing-related circadian-phase movement disorders.

Among the mood disorders that are especially distinguished are depressive disorders (unipolar depression), bipolar disorders, mood disorders caused by a general medical complaint and also mood disorders induced by pharmacological substances.

Among the bipolar disorders that are especially distinguished are bipolar I disorders and bipolar II disorders, especially including seasonal affective disorders.

The compounds that are the subject of the invention, which modulate the circadian periodicity, may be useful in the treatment of anxiety and depressive disorders caused in particular by an impairment in the secretion of CRF.

Among the depressive disorders that are especially distinguished are major depressive disorders, dysthymic disorders and other unspecified depressive disorders.

According to one of its aspects, the invention relates to a compound of formula (I) in base form or in the form of an addition salt with a pharmaceutically acceptable acid, for treating anxiety and depressive disorders due in particular to impairment of CRF secretion.

The compounds that are the subject of the invention, which modulate the circadian periodicity, may be useful for preparing a medicament for treating diseases related to dependency on abuse substances such as cocaine, morphine, nicotine, ethanol and cannabis.

According to one of its aspects, the invention relates to a compound of formula (I) in base form or in the form of an addition salt with a pharmaceutically acceptable acid, for treating diseases related to dependency on abuse substances such as cocaine, morphine, nicotine, ethanol and cannabis.

By inhibiting casein kinase 1 epsilon and/or casein kinase 1 delta, the compounds according to the invention may be used for preparing medicaments, especially for preparing a medicament for preventing or treating diseases related to hyperphosphorylation of the tau protein, especially Alzheimer's disease.

According to one of its aspects, the invention relates to a compound of formula (I) in base form or in the form of an addition salt with a pharmaceutically acceptable acid, for preventing or treating diseases related to hyperphosphorylation of the tau protein, especially Alzheimer's disease.

By inhibiting casein kinase 1 epsilon and/or casein kinase 1 delta, the compounds according to the invention may also be used for preparing medicaments, especially for preparing a medicament for preventing or treating neuropathic pain.

According to one of its aspects, the invention relates to a compound of formula (I) in base form or in the form of an addition salt with a pharmaceutically acceptable acid, for preventing or treating neuropathic pain.

The compounds according to the invention may also be used for the preparation of medicaments, especially for the preparation of a medicament for preventing or treating inflammatory diseases, especially such as inflammatory diseases of the central nervous system, for instance multiple sclerosis, encephalitis, myelitis and encephalomyelitis, and other inflammatory diseases, for instance vascular pathologies, atherosclerosis, joint inflammation, arthrosis and rheumatoid arthritis.

According to one of its aspects, the invention relates to a compound of formula (I) in base form or in the form of an addition salt with a pharmaceutically acceptable acid, for preventing and/or treating inflammatory diseases, especially those indicated above.

The compounds according to the invention in base form or in the form of an addition salt with a pharmaceutically acceptable acid may thus be used for the preparation of medicaments, in particular medicaments that are useful for treating or preventing diseases related to casein kinase 1 epsilon and/or casein kinase 1 delta.

According to one of its aspects, the invention relates to a compound of formula (I) in base form or in the form of an addition salt with a pharmaceutically acceptable acid, for preventing for treating diseases related to casein kinase 1 epsilon and/or casein kinase 1 delta.

According to one of its aspects, the invention relates to a compound of formula (I) in base form or in the form of an addition salt with a pharmaceutically acceptable acid, for its use as a medicament.

According to one of its aspects, the invention relates to a medicament comprising a compound of formula (I) in base form or in the form of an addition salt with a pharmaceutically acceptable acid.

Thus, according to another of its aspects, a subject of the invention is medicaments comprising a compound of formula (I), or an addition salt thereof with a pharmaceutically acceptable acid, or alternatively a hydrate or solvate of the compound of formula (I).

According to another of its aspects, the present invention relates to pharmaceutical compositions comprising, as active principle, a compound according to the invention in base form or in the form of an addition salt with a pharmaceutically acceptable acid, and optionally one or more pharmaceutically acceptable excipients. These pharmaceutical compositions thus contain an effective dose of at least one compound according to the invention or a pharmaceutically acceptable salt, a hydrate or solvate of the said compound, and also optionally at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical administration, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may range from 0.1 to 20 mg/kg, in one or more dosage intakes.

There may be particular cases in which higher or lower dosages are appropriate; such dosages are not outside the context of the invention. According to the usual practice, the dosage that is appropriate to each patient is determined by the practitioner according to the mode of administration and the weight and response of the said patient.

According to another of its aspects, the present invention also relates to a method for preventing and/or treating the pathologies indicated above, which comprises the administration to a patient of an effective dose of a compound according to the invention, or a pharmaceutically acceptable salt or hydrate or solvate thereof.

What is claimed is:

1. A compound of formula (I):

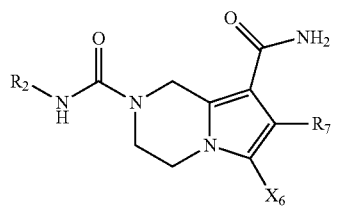

wherein $R_2$ represents:
- a group $C_{1-10}$-alkyl, $C_{3-7}$-cycloalkyl-$C_{1-6}$-alkyl, $C_{1-6}$-alkylthio-$C_{1-10}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, $C_{1-10}$-fluoroalkyl, or $C_{1-10}$-alkoxyimino-$C_{1-10}$-alkyl;
- a group $C_{8-10}$-cycloalkyl, $C_{3-10}$-fluorocycloalkyl, or hydroxy-$C_{8-10}$-cycloalkyl;
- a group $C_{3-7}$-cycloalkyl which may be substituted with one or two groups independently chosen from $C_{1-6}$-alkyl, $C_{3-7}$-cycloalkyl, hydroxy, $C_{1-10}$-fluoroalkyl and $C_{1-10}$-alkyoxyimino;
- a heterocyclic group comprising from 3 to 8 carbon atoms and at least one heteroatom chosen from nitrogen, oxygen, sulfur and the oxide or dioxide form of sulfur, this heterocyclic group possibly being substituted with one or more groups selected from among hydroxy, $C_{1-6}$-alkyl, hydroxy-$C_{1-6}$-alkyl, and $C_{1-6}$-fluoroalkyl; or
- a group $C_{1-10}$-alkyl substituted with a heterocyclic group comprising from 3 to 8 carbon atoms and at least one heteroatom chosen from nitrogen, oxygen, sulfur and the oxide or dioxide form of sulfur, this heterocyclic group optionally being substituted with one or more groups chosen from among hydroxy, $C_{1-6}$-alkyl, hydroxy-$C_{1-6}$-alkyl, and $C_{1-6}$-fluoroalkyl;

$X_6$ represents a hydrogen, fluorine, chlorine or bromine atom or a group $C_{1-6}$-alkyl, $C_{3-7}$-cycloalkyl, $C_{3-7}$-cycloalkyl-$C_{1-6}$-alkyl, $C_{1-6}$-fluoroalkyl or cyano;

$R_7$ represents a phenyl group or a naphthyl group, optionally substituted with one or more substituents $X_7$, which may be identical or different;

$X_7$ represents:
- a halogen atom chosen from fluorine, chlorine and bromine atoms, or a group chosen from:
- hydroxy,
- $C_{1-6}$-alkyl, $C_{3-7}$-cycloalkyl, $C_{3-7}$-cycloalkyl-$C_{1-6}$-alkyl, hydroxy-$C_{1-6}$-alkyl, hydroxy-$C_{3-7}$-cycloalkyl, hydroxy-$C_{3-7}$-cycloalkyl-$C_{1-6}$-alkyl,
- $C_{1-6}$-alkoxy, $C_{3-7}$-cycloalkoxy, $C_{3-7}$-cycloalkyl-$C_{1-6}$-alkoxy,
- $C_{1-6}$-alkylthio, $C_{3-7}$-cycloalkylthio, $C_{3-7}$-cycloalkyl-$C_{1-6}$-alkylthio,
- aryl, aryl-$C_{1-6}$-alkyl,
- aryloxy, aryl-$C_{1-6}$-alkoxy,
- $C_{1-6}$-fluoroalkyl, $C_{3-7}$-fluorocycloalkyl, $C_{3-7}$-fluorocycloalkyl-$C_{1-6}$-alkyl,
- $C_{1-6}$-fluoroalkoxy, $C_{3-7}$-fluorocycloalkoxy, $C_{3-7}$-fluorocycloalkyl-$C_{1-6}$-alkoxy,
- cyano, cyano-$C_{1-6}$-alkyl, cyano-$C_{1-6}$-alkoxy,
- $NR_aR_b$, $NR_cCOR_d$, $NR_cSO_2R_d$, $NR_cSO_2NR_aR_b$, $CONR_aR_b$, $CON(OR_c)R_d$, and
- a heteroaryl group,
the aryl or heteroaryl groups being optionally substituted with one or more substituents chosen from fluorine, chlorine and bromine atoms or a group $C_{1-6}$-alkyl, $C_{3-7}$-cycloalkyl, $C_{1-6}$-alkoxy, $C_{1-6}$-fluoroalkyl, $C_{1-6}$-fluoroalkoxy or cyano;

$R_a$ and $R_b$ represent, independently of each other, a hydrogen atom or a group $C_{1-6}$-alkyl, $C_{3-7}$-cycloalkyl or $C_{3-7}$-cycloalkyl-$C_{1-6}$-alkyl, or alternatively they form with the atom that bears them a ring chosen from azetidine, pyrrolidine, piperidine, morpholine, thiomorpholine, azepine and piperazine, this ring being optionally substituted with one or more groups $C_{1-6}$-alkyl; and $R_c$ and $R_d$ represent, independently of each other, a hydrogen atom or a group $C_{1-6}$-alkyl, $C_{3-7}$-cycloalkyl or $C_{3-7}$-cycloalkyl-$C_{1-6}$-alkyl;

in the form of the base or of an acid-addition salt.

2. The compound of formula (I) according to claim 1, wherein $R_2$ represents:
- a group $C_{1-10}$-alkyl, $C_{3-7}$-cycloalkyl-$C_{1-6}$-alkyl, $C_{1-6}$-alkoxy-$C_{1-10}$-alkyl, hydroxy-$C_{1-10}$-alkyl, hydroxy-$C_{1-6}$-alkyl-$C_{3-7}$-cycloalkyl-$C_{1-6}$-alkyl, or $C_{1-10}$-fluoroalkyl;
- a group $C_{8-10}$-cycloalkyl, $C_{3-10}$-fluorocycloalkyl, or hydroxy-$C_{8-10}$-cycloalkyl;

a group $C_{3-7}$-cycloalkyl which may be substituted with one or two groups independently chosen from $C_{1-6}$-alkyl, $C_{3-7}$-cycloalkyl, hydroxy, $C_{1-10}$-fluoroalkyl and $C_{1-10}$-alkoxyimino;

a heterocyclic group comprising from 3 to 8 carbon atoms and at least one heteroatom chosen from oxygen or a sulfur atom in dioxide form, this heterocyclic group possibly being substituted with one or more groups $C_{1-6}$-alkyl; or a group $C_{1-10}$-alkyl substituted with a heterocyclic group comprising from 3 to 8 carbon atoms and at least one oxygen heteroatom, this heterocyclic group possibly being substituted with one or more groups $C_{1-6}$-alkyl;

$R_7$ represents a phenyl group optionally substituted with one or more substituents $X_7$, which may be identical or different, chosen from:

a fluorine or chlorine atom, or a group chosen from $C_{1-6}$-alkyl, $C_{3-7}$-cycloalkyl, $C_{1-6}$-alkoxy, $C_{3-7}$-cycloalkyl-$C_{1-6}$-alkoxy, $C_{1-6}$-alkylthio, aryl, aryloxy, aryl-$C_{1-6}$-alkoxy, $C_{1-6}$ fluoroalkyl, $C_{1-6}$ fluoroalkoxy, cyano, cyano-$C_{1-6}$-alkoxy, $NR_aR_b$, $NR_cSO_2R_d$, $NR_cSO_2NR_aR_b$, $CONR_aR_b$, $CON(OR_c)R_d$, and heteroaryl chosen from an oxadiazolyl and pyrazolyl group, optionally substituted with a group $C_{1-6}$-alkyl, the aryl group being optionally substituted with a fluorine atom;

$R_a$ and $R_b$ represent, independently of each other, a hydrogen atom or a group $C_{1-6}$-alkyl, $C_{3-7}$-cycloalkyl, or alternatively they form with the atom that bears them a ring chosen from pyrrolidine and morpholine; and $R_c$ and $R_d$ represent, independently of each other, a hydrogen atom or a group $C_{1-6}$-alkyl;

in the form of the base or of an acid-addition salt.

3. The compound according to claim 1, which is $N^2$-tert-butyl-6-chloro-7-phenyl-3,4-dihydropyrrolo[1,2-a]pyrazine-2,8(1H)-dicarboxamide, in the form of the base or of an acid-addition salt.

4. A pharmaceutical composition comprising at least one compound of formula (I) according to claim 1, in the form of the base or of an addition salt with a pharmaceutically acceptable acid, and optionally one or more pharmaceutically acceptable excipients.

5. A pharmaceutical composition comprising at least one compound of formula (I) according to claim 2, in the form of the base or of an addition salt with a pharmaceutically acceptable acid, and optionally one or more pharmaceutically acceptable excipients.

6. A process for preparing a compound of formula (I) according to claim 1, comprising a step that comprises reacting a compound of formula (II):

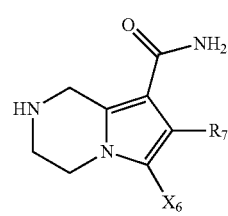

wherein $R_7$ and $X_6$ are as defined in formula (I) according to claim 1, with a compound of formula (IIb):

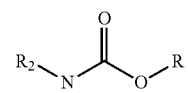

wherein $R_2$ is as defined in formula (I) according to claim 1 and R represents a group selected from phenyl, pentafluorophenyl and 4-nitrophenyl, in an aprotic solvent and in the presence of a mineral base, or alternatively with a compound of formula (IIa):

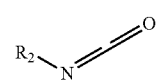

wherein $R_2$ is as defined in formula (I) according to claim 1, in an aprotic solvent and optionally in the presence of an organic amine.

7. A compound of formula (I), selected from the group consisting of:

$N^2$-tert-butyl-7-phenyl-3,4-dihydropyrrolo[1,2-a]pyrazine-2,8(1H)-dicarboxamide;

$N^2$-tert-butyl-7-(4-methoxyphenyl)-3,4-dihydropyrrolo[1,2-a]pyrazine-2,8(1H)-dicarboxamide;

$N^2$-tert-butyl-6-methyl-7-phenyl-3,4-dihydropyrrolo[1,2-a]pyrazine-2,8(1H)-dicarboxamide;

$N^2$-tert-butyl-7-(4-methoxyphenyl)-6-methyl-3,4-dihydropyrrolo[1,2-a]pyrazine-2,8(1H)-dicarboxamide;

$N^2$-tert-butyl-6-methyl-7-(4-phenoxyphenyl)-3,4-dihydropyrrolo[1,2-a]pyrazine-2,8(1H)-dicarboxamide;

$N^2$-6-di-cyclo-propyl-7-(4-methoxyphenyl)-3,4-dihydropyrrolo[1,2-a]pyrazine-2,8(1H)-dicarboxamide;

6-cyclo-propyl-7-phenyl-$N^2$-(iso-propyl)-3,4-dihydropyrrolo[1,2-a]pyrazine-2,8(1H)-dicarboxamide;

6-cyclo-propyl-7-(4-methoxyphenyl)-$N^2$-(iso-propyl)-3,4-dihydropyrrolo[1,2-a]pyrazine-2,8(1H)-dicarboxamide;

6-cyclo-propyl-7-phenyl-$N^2$-(iso-butyl)-3,4-dihydropyrrolo[1,2-a]pyrazine-2,8(1H)-dicarboxamide;

$N^2$-tert-butyl-6-cyclo-propyl-7-phenyl-3,4-dihydropyrrolo[1,2-a]pyrazine-2,8(1H)-dicarboxamide;

$N^2$-tert-butyl-6-cyclo-propyl-7-(3-methylphenyl)-3,4-dihydropyrrolo[1,2-a]pyrazine-2,8(1H)-dicarboxamide;

$N^2$-tert-butyl-6-cyclo-propyl-7-(4-methylphenyl)-3,4-dihydropyrrolo[1,2-a]pyrazine-2,8(1H)-dicarboxamide;

$N^2$-tert-butyl-6-cyclo-propyl-7-[4-(iso-propyl)phenyl]-3,4-dihydropyrrolo[1,2-a]pyrazine-2,8(1H)-dicarboxamide;

$N^2$-tert-butyl-7-(4-cyclo-hexylphenyl)-6-cyclo-propyl-3, 4-dihydropyrrolo[1,2-a]pyrazine-2,8(1H)-dicarboxamide;

7-(biphenyl-4-yl)-$N^2$-tert-butyl-6-cyclo-propyl-3,4-dihydropyrrolo[1,2-a]pyrazine-2,8(1H)-dicarboxamide;

$N^2$-tert-butyl-6-cyclo-propyl-7-[3-(trifluoromethyl)phenyl]-3,4-dihydropyrrolo[1,2-a]pyrazine-2,8(1H)-dicarboxamide;

$N^2$-tert-butyl-6-cyclo-propyl-7-[3-(dimethylcarbamoyl)phenyl]-3,4-dihydropyrrolo[1,2-a]pyrazine-2,8(1H)-dicarboxamide;

$N^2$-tert-butyl-6-cyclo-propyl-7-[4-(cyclo-propylcarbamoyl)phenyl]-3,4-dihydropyrrolo[1,2-a]pyrazine-2,8(1H)-dicarboxamide;

$N^2$-tert-butyl-6-cyclo-propyl-7-[4-(pyrrolidin-1-ylcarbonyl)phenyl]-3,4-dihydropyrrolo[1,2-a]pyrazine-2,8(1H)-dicarboxamide;

$N^2$-tert-butyl-6-cyclo-propyl-7-{4-[methoxy(methyl)carbamoyl]phenyl}-3,4-dihydropyrrolo[1,2-a]pyrazine-2,8(1H)-dicarboxamide;

$N^2$-tert-butyl-7-(3-cyanophenyl)-6-cyclo-propyl-3,4-dihydropyrrolo[1,2-a]pyrazine-2,8(1H)-dicarboxamide;

$N^2$-tert-butyl-7-(4-cyanophenyl)-6-cyclo-propyl-3,4-dihydropyrrolo[1,2-a]pyrazine-2,8(1H)-dicarboxamide;

$N^2$-tert-butyl-6-cyclo-propyl-7-[4-(5-methyl-1.3,4-oxadiazol-2-yl)phenyl]-3,4-dihydropyrrolo[1,2-a]pyrazine-2,8(1H)-dicarboxamide;

$N^2$-tert-butyl-6-cyclo-propyl-7-[4-(trifluoromethyl)phenyl]-3,4-dihydropyrrolo[1,2-a]pyrazine-2,8(1H)-dicarboxamide;

$N^2$-tert-butyl-6-cyclo-propyl-7-(naphthalen-2-yl)-3,4-dihydropyrrolo[1,2-a]pyrazine-2,8(1H)-dicarboxamide;

$N^2$-tert-butyl-6-cyclo-propyl-7-{3-[(dimethylsulfamoyl)amino]phenyl}-3,4-dihydropyrrolo[1,2-a]pyrazine-2,8(1H)-dicarboxamide;

$N^2$-tert-butyl-6-cyclo-propyl-7-[3-(1H-pyrazol-1-yl)phenyl]-3,4-dihydropyrrolo[1,2-a]pyrazine-2,8(1H)-dicarboxamide;

$N^2$-tert-butyl-6-cyclo-propyl-7-[4-(dimethylamino)phenyl]-3,4-dihydropyrrolo[1,2-a]pyrazine-2,8(1H)-dicarboxamide;

$N^2$-tert-butyl-6-cyclo-propyl-7-{4-[(methylsulfonyl)amino]phenyl}-3,4-dihydropyrrolo[1,2-a]pyrazine-2,8(1H)-dicarboxamide;

$N^2$-tert-butyl-6-cyclo-propyl-7-[4-(morpholin-4-yl)phenyl]-3,4-dihydropyrrolo[1,2-a]pyrazine-2,8(1H)-dicarboxamide;

$N^2$-tert-butyl-6-cyclo-propyl-7-[4-(1H-pyrazol-1-yl)phenyl]-3,4-dihydropyrrolo[1,2-a]pyrazine-2,8(1H)-dicarboxamide;

$N^2$-tert-butyl-6-cyclo-propyl-7-(3-methoxyphenyl)-3,4-dihydropyrrolo[1,2-a]pyrazine-2,8(1H)-dicarboxamide;

$N^2$-tert-butyl-6-cyclo-propyl-7-[3-(cyclo-propyl methoxy)phenyl]-3,4-dihydropyrrolo[1,2-a]pyrazine-2,8(1H)-dicarboxamide;

7-[3-(benzyloxy)phenyl]-$N^2$-tert-butyl-6-cyclo-propyl-3,4-dihydropyrrolo[1,2-a]pyrazine-2,8(1H)-dicarboxamide;

$N^2$-tert-butyl-6-cyclo-propyl-7-[3-(trifluoromethoxy)phenyl]-3,4-dihydropyrrolo[1,2-a]pyrazine-2,8(1H)-dicarboxamide;

$N^2$-tert-butyl-6-cyclo-propyl-7-[4-(methoxy)phenyl]-3,4-dihydropyrrolo[1,2-a]pyrazine-2,8(1H)-dicarboxamide;

$N^2$-tert-butyl-6-cyclo-propyl-7-[4-(cyclo-propyl methoxy)phenyl]-3,4-dihydropyrrolo[1,2-a]pyrazine-2,8(1H)-dicarboxamide;

7-(4-butoxyphenyl)-$N^2$-tert-butyl-6-cyclo-propyl-3,4-dihydropyrrolo[1,2-a]pyrazine-2,8(1H)-dicarboxamide;

$N^2$-tert-butyl-6-cyclo-propyl-7-(4-phenoxyphenyl)-3,4-dihydropyrrolo[1,2-a]pyrazine-2,8(1H)-dicarboxamide;

7-[4-(benzyloxy)phenyl]-$N^2$-tert-butyl-6-cyclo-propyl-3,4-dihydropyrrolo[1,2-a]pyrazine-2,8(1H)-dicarboxamide;

$N^2$-tert-butyl-6-cyclo-propyl-7-{4-[(4-fluorobenzyl)oxy]phenyl}-3,4-dihydropyrrolo[1,2-a]pyrazine-2,8(1H)-dicarboxamide;

$N^2$-tert-butyl-7-{3-chloro-4-[(4-fluorobenzyl)oxy]phenyl}-6-cyclo-propyl-3,4-dihydropyrrolo[1,2-a]pyrazine-2,8(1H)-dicarboxamide;

$N^2$-tert-butyl-7-[4-(cyanomethoxy)phenyl]-6-cyclo-propyl-3,4-dihydropyrrolo[1,2-a]pyrazine-2,8(1H)-dicarboxamide;

$N^2$-tert-butyl-6-cyclo-propyl-7-[4-(trifluoromethoxy)phenyl]-3,4-dihydropyrrolo[1,2-a]pyrazine-2,8(1H)-dicarboxamide;

$N^2$-tert-butyl-6-cyclo-propyl-7-(2-fluorophenyl)-3,4-dihydropyrrolo[1,2-a]pyrazine-2,8(1H)-dicarboxamide;

$N^2$-tert-butyl-6-cyclo-propyl-7-(3-fluorophenyl)-3,4-dihydropyrrolo[1,2-a]pyrazine-2,8(1H)-dicarboxamide;

$N^2$-tert-butyl-6-cyclo-propyl-7-(4-fluorophenyl)-3,4-dihydropyrrolo[1,2-a]pyrazine-2,8(1H)-dicarboxamide;

$N^2$-tert-butyl-6-cyclo-propyl-7-[4-(methylsulfanyl)phenyl]-3,4-dihydropyrrolo[1,2-a]pyrazine-2,8(1H)-dicarboxamide;

$N^2$-cyclo-hexyl-6-cyclo-propyl-7-phenyl-3,4-dihydropyrrolo[1,2-a]pyrazine-2,8(1H)-dicarboxamide;

$N^2$-(cyclo-hexylmethyl)-6-cyclo-propyl-7-phenyl-3,4-dihydropyrrolo[1,2-a]pyrazine-2,8(1H)-dicarboxamide;

$N^2$-[1,1-bi(cyclo-propyl)-1-yl]-6-cyclo-propyl-7-(4-methoxyphenyl)-3,4-dihydropyrrolo[1,2-a]pyrazine-2,8(1H)-dicarboxamide;

6-cyclo-propyl-7-phenyl-$N^2$-(2,4,4-trimethylpentan-2-yl)-3,4-dihydropyrrolo[1,2-a]pyrazine-2,8(1H)-dicarboxamide;

6-cyclo-propyl-$N^2$-(hexahydro-2,5-methanopentalen-3a(1H)-yl)-7-(4-methoxyphenyl)-3,4-dihydropyrrolo[1,2-a]pyrazine-2,8(1H)-dicarboxamide;

$N^2$-(adamantan-1-yl)-6-cyclo-propyl-7-phenyl-3,4-dihydropyrrolo[1,2-a]pyrazine-2,8(1H)-dicarboxamide;

$N^2$-(adamantan-1-yl)-6-cyclo-propyl-7-(4-methoxyphenyl)-3,4-dihydropyrrolo[1,2-a]pyrazine-2,8(1H)-dicarboxamide;

6-cyclo-propyl-7-(4-methoxyphenyl)-$N^2$-(tetrahydro-2H-pyran-4-yl)-3,4-dihydropyrrolo[1,2-a]pyrazine-2,8(1H)-dicarboxamide;

6-cyclo-propyl-$N^2$-(1-methoxy-2-methylpropan-2-yl)-7-(4-methoxyphenyl)-3,4-dihydropyrrolo[1,2-a]pyrazine-2,8(1H)-dicarboxamide;

$N^2$-tert-butyl-6-fluoro-7-phenyl-3,4-dihydropyrrolo[1,2-a]pyrazine-2,8(1H)-dicarboxamide;

6-chloro-$N^2$-iso-butyl-7-phenyl-3,4-dihydropyrrolo[1,2-a]pyrazine-2,8(1H)-dicarboxamide;

$N^2$-tert-butyl-6-chloro-7-phenyl-3,4-dihydropyrrolo[1,2-a]pyrazine-2,8(1H)-dicarboxamide;

$N^2$-tert-butyl-6-chloro-7-(3-methylphenyl)-3,4-dihydropyrrolo[1,2-a]pyrazine-2,8(1H)-dicarboxamide;

$N^2$-tert-butyl-6-chloro-7-(3-methoxyphenyl)-3,4-dihydropyrrolo[1,2-a]pyrazine-2,8(1H)-dicarboxamide;

$N^2$-tert-butyl-6-chloro-7-[3-(trifluoromethoxy)phenyl]-3,4-dihydropyrrolo[1,2-a]pyrazine-2,8(1H)-dicarboxamide;

$N^2$-tert-butyl-6-chloro-7-(4-methoxyphenyl)-3,4-dihydropyrrolo[1,2-a]pyrazine-2,8(1H)-dicarboxamide;

$N^2$-tert-butyl-6-chloro-7-(3-cyanophenyl)-3,4-dihydropyrrolo[1,2-a]pyrazine-2,8(1H)-dicarboxamide;

$N^2$-tert-butyl-6-chloro-7-[3-(trifluoromethyl)phenyl]-3,4-dihydropyrrolo[1,2-a]pyrazine-2,8(1H)-dicarboxamide;

$N^2$-tert-butyl-6-chloro-7-(3-fluorophenyl)-3,4-dihydropyrrolo[1,2-a]pyrazine-2,8(1H)-dicarboxamide;

6-chloro-$N^2$-(cyclo-propylmethyl)-7-phenyl-3,4-dihydropyrrolo[1,2-a]pyrazine-2,8(1H)-dicarboxamide;

6-chloro-$N^2$-(3-methylbutyl)-7-phenyl-3,4-dihydropyrrolo[1,2-a]pyrazine-2,8(1H)-dicarboxamide;

6-chloro-$N^2$-(2,2-dimethylpropyl)-7-phenyl-3,4-dihydropyrrolo[1,2-a]pyrazine-2,8(1H)-dicarboxamide;

6-chloro-$N^2$-(2-ethylbutyl)-7-phenyl-3,4-dihydropyrrolo[1,2-a]pyrazine-2,8(1H)-dicarboxamide;

6-chloro-$N^2$-(3.3-dimethylbutyl)-7-phenyl-3,4-dihydropyrrolo[1,2-a]pyrazine-2,8(1H)-dicarboxamide;

6-chloro-7-(3-fluorophenyl)-$N^2$-(3-hydroxy-2,2-dimethylpropyl)-3,4-dihydropyrrolo[1,2-a]pyrazine-2,8(1H)-dicarboxamide;

6-chloro-$N^2$-(3-hydroxy-2,2-dimethylpropyl)-7-(3-trifluoromethyl-phenyl)-3,4-dihydropyrrolo[1,2-a]pyrazine-2,8(1H)-dicarboxamide;

6-chloro-7-(3-fluorophenyl)-$N^2$-{[1-(hydroxymethyl)cyclo-propyl]methyl}-3,4-dihydropyrrolo[1,2-a]pyrazine-2,8(1H)-dicarboxamide;

6-chloro-7-phenyl-$N^2$-(2,2,2-trifluoroethyl)-3,4-dihydropyrrolo[1,2-a]pyrazine-2,8(1H)-dicarboxamide;

6-chloro-7-(3-fluorophenyl)-$N^2$-(2,2,2-trifluoroethyl)-3,4-dihydropyrrolo[1,2-a]pyrazine-2,8(1H)-dicarboxamide;

6-chloro-7-(3-fluorophenyl)-$N^2$-[(2S)-1,1,1-trifluoropropan-2-yl]-3,4-dihydropyrrolo[1,2-a]pyrazine-2,8(1H)-dicarboxamide;

6-chloro-7-(3-fluorophenyl)-$N^2$-(1,1,1-trifluoro-2-methylpropan-2-yl)-3,4-dihydropyrrolo[1,2-a]pyrazine-2,8(1H)-dicarboxamide;

6-chloro-7-(3-fluorophenyl)-$N^2$-(3,3,3-trifluoropropyl)-3,4-dihydropyrrolo[1,2-a]pyrazine-2,8(1H)-dicarboxamide;

6-chloro-7-(3-fluorophenyl)-$N^2$-(4,4,4-trifluorobutyl)-3,4-dihydropyrrolo[1,2-a]pyrazine-2,8(1H)-dicarboxamide;

6-chloro-$N^2$-cyclo-hexyl-7-phenyl-3,4-dihydropyrrolo[1,2-a]pyrazine-2,8(1H)-dicarboxamide;

trans-6-chloro-7-(3-fluorophenyl)-$N^2$-(4-hydroxy-cyclohexyl)-3,4-dihydropyrrolo[1,2-a]pyrazine-2,8(1H)-dicarboxamide;

trans-6-chloro-7-(3-fluorophenyl)-$N^2$-(4-hydroxy-4-methyl-cyclo-hexyl)-3,4-dihydropyrrolo[1,2-a]pyrazine-2,8(1H)-dicarboxamide;

trans-6-chloro-7-(3-fluorophenyl)-$N^2$-(4-hydroxy-4-trifluoromethyl-cyclo-hexyl)-3,4-dihydropyrrolo[1,2-a]pyrazine-2,8(1H)-dicarboxamide;

trans-6-chloro-7-(3-fluorophenyl)-$N^2$-(4-methoxyimino-cyclohexyl)-3,4-dihydropyrrolo[1,2-a]pyrazine-2,8(1H)-dicarboxamide;

trans-6-chloro-7-(3-fluorophenyl)-$N^2$-(4-tert-butyloxyimino-cyclohexyl)-3,4-dihydropyrrolo[1,2-a]pyrazine-2,8(1H)-dicarboxamide;

$N^2$-(bicyclo[2.2.1]hept-2-yl)-6-chloro-7-phenyl-3,4-dihydropyrrolo[1,2-a]pyrazine-2,8(1H)-dicarboxamide;

6-chloro-$N^2$-(4,4-difluoro-cyclo-hexyl)-7-(3-fluorophenyl)-3,4-dihydropyrrolo[1,2-a]pyrazine-2,8(1H)-dicarboxamide;

6-chloro-7-(3-fluorophenyl)-$N^2$-(oxetan-3-yl)-3,4-dihydropyrrolo[1,2-a]pyrazine-2,8(1H)-dicarboxamide;

6-chloro-7-(3-fluorophenyl)-$N^2$-(3-methyl-oxetan-3-ylmethyl)-3,4-dihydropyrrolo[1,2-a]pyrazine-2,8(1H)-dicarboxamide;

6-chloro-7-phenyl-$N^2$-(tetrahydrofuran-3-yl)-3,4-dihydropyrrolo[1,2-a]pyrazine-2,8(1H)-dicarboxamide;

6-chloro-7-phenyl-$N^2$-(tetrahydro-2H-pyran-4-yl)-3,4-dihydropyrrolo[1,2-a]pyrazine-2,8(1H)-dicarboxamide;

6-chloro-7-(3-methylphenyl)-$N^2$-(tetrahydro-2H-pyran-4-yl)-3,4-dihydropyrrolo[1,2-a]pyrazine-2,8(1H)-dicarboxamide;

6-chloro-7-(3-cyanophenyl)-$N^2$-(tetrahydro-2H-pyran-4-yl)-3,4-dihydropyrrolo[1,2-a]pyrazine-2,8(1H)-dicarboxamide;

6-chloro-$N^2$-(tetrahydro-2H-pyran-4-yl)-7-[3-(trifluoromethyl)phenyl]-3,4-dihydropyrrolo[1,2-a]pyrazine-2,8(1H)-dicarboxamide;

6-chloro-$N^2$-(tetrahydro-2H-pyran-4-yl)-7-[3-(trifluoromethoxy)phenyl]-3,4-dihydropyrrolo[1,2-a]pyrazine-2,8(1H)-dicarboxamide;

6-chloro-7-(3-fluorophenyl)-$N^2$-(tetrahydro-2H-pyran-4-yl)-3,4-dihydropyrrolo[1,2-a]pyrazine-2,8(1H)-dicarboxamide;

6-chloro-7-(3-fluorophenyl)-$N^2$-(2,2-dimethyl-tetrahydro-2H-pyran-4-yl)-3,4-dihydropyrrolo[1,2-a]pyrazine-2,8(1H)-dicarboxamide;

cis-6-chloro-$N^2$-(2.6-dimethyl-tetrahydro-2H-pyran-4-yl)-7-(3-fluorophenyl)-3,4-dihydropyrrolo[1,2-a]pyrazine-2,8(1H)-dicarboxamide;

6-chloro-$N^2$-(1,1-dioxydotetrahydrothiophen-3-yl)-7-phenyl-3,4-dihydropyrrolo[1,2-a]pyrazine-2,8(1H)-dicarboxamide;

6-chloro-$N^2$-(1,1-dioxydotetrahydrothiophen-3-yl)-7-(3-fluorophenyl)-3,4-dihydropyrrolo[1,2-a]pyrazine-2,8(1H)-dicarboxamide;

6-chloro-$N^2$-(1,1-dioxydotetrahydro-2H-thiopyran-4-yl)-7-(3-fluorophenyl)-3,4-dihydropyrrolo[1,2-a]pyrazine-2,8(1H)-dicarboxamide;

6-bromo-7-(3-fluorophenyl)-$N^2$-tert-butyl-3,4-dihydropyrrolo[1,2-a]pyrazine-2,8(1H)-dicarboxamide;

6-cyano-7-(3-fluorophenyl)-$N^2$-(tert-butyl)-3,4-dihydropyrrolo[1,2-a]pyrazine-2,8(1H)-dicarboxamide;

6-cyano-7-(3-fluorophenyl)-$N^2$-((2S)-1,1,1-trifluoropropan-2-yl)-3,4-dihydropyrrolo[1,2-a]pyrazine-2,8(1H)-dicarboxamide;

6-cyano-7-(3-fluorophenyl)-$N^2$-(1,1,1-trifluoro-2-methylpropan-2-yl)-3,4-dihydropyrrolo[1,2-a]pyrazine-2,8(1H)-dicarboxamide;

6-cyano-7-(3-fluorophenyl)-$N^2$-(4,4,4-trifluoro-butyl)-3,4-dihydropyrrolo[1,2-a]pyrazine-2,8(1H)-dicarboxamide;

6-cyano-7-(3-fluorophenyl)-$N^2$-(tetrahydro-2H-pyran-4-yl)-3,4-dihydropyrrolo[1,2-a]pyrazine-2,8(1H)-dicarboxamide; and 6-cyano-$N^2$-(4,4-difluoro-cyclohexyl)-7-(3-fluorophenyl)-3,4-dihydropyrrolo[1,2-a]pyrazine-2,8(1H)-dicarboxamide;

in the form of the base or of an acid-addition salt.

8. A pharmaceutical composition comprising at least one compound according to claim 7, in the form of the base or of an addition salt with a pharmaceutically acceptable acid, and optionally one or more pharmaceutically acceptable excipients.

* * * * *